(12) United States Patent
Kilburn et al.

(10) Patent No.: US 9,108,938 B2
(45) Date of Patent: Aug. 18, 2015

(54) CYCLIC AMINES

(71) Applicant: H. Lundbeck A/S, Valby (DK)

(72) Inventors: John Paul Kilburn, Haslev (DK); Lars Kyhn Rasmussen, Brønshøj (DK); Mikkel Jessing, København NV (DK); Eman Mohammed Eldemenky, Wayne, NJ (US); Bin Chen, East Windsor, NJ (US); Yu Jiang, East Windsor, NJ (US)

(73) Assignee: H. Lundbeck A/S, Valby (DK)

( * ) Notice: Subject to any disclaimer, the term of this patent is extended or adjusted under 35 U.S.C. 154(b) by 0 days.

(21) Appl. No.: 14/050,466

(22) Filed: Oct. 10, 2013

(65) Prior Publication Data

US 2014/0107335 A1 Apr. 17, 2014

Related U.S. Application Data

(60) Provisional application No. 61/713,099, filed on Oct. 12, 2012.

(51) Int. Cl.

| | | |
|---|---|---|
| *C07D 413/06* | (2006.01) | |
| *C07D 295/13* | (2006.01) | |
| *C07D 401/06* | (2006.01) | |
| *C07D 403/06* | (2006.01) | |
| *C07D 211/38* | (2006.01) | |
| *C07D 213/40* | (2006.01) | |
| *C07D 239/26* | (2006.01) | |
| *C07D 267/10* | (2006.01) | |
| *C07D 209/52* | (2006.01) | |

(52) U.S. Cl.
CPC ............ *C07D 295/13* (2013.01); *C07D 209/52* (2013.01); *C07D 211/38* (2013.01); *C07D 213/40* (2013.01); *C07D 239/26* (2013.01); *C07D 267/10* (2013.01); *C07D 401/06* (2013.01); *C07D 403/06* (2013.01); *C07D 413/06* (2013.01)

(58) Field of Classification Search
CPC .. C07D 211/38; C07D 401/06; C07D 209/52; C07D 213/40; C07D 267/10; C07D 403/06; C07D 295/13; C07D 239/26; C07D 413/06
See application file for complete search history.

(56) References Cited

FOREIGN PATENT DOCUMENTS

| WO | 01/46200 A1 | 6/2001 |
|---|---|---|
| WO | 2006/134341 A1 | 12/2006 |
| WO | 20091086303 A2 | 7/2009 |
| WO | 2009/013200 A1 | 10/2009 |
| WO | 20131064460 A1 | 5/2012 |

OTHER PUBLICATIONS

CAS Registry No. 1216844-88-0; Apr. 5, 2010.*
International Search Report and Written Opinion issued Nov. 27, 2013 in International Application No. PCT/EP2013/071253.
Kelly J McClure et al., 2011, "Discovery of a novel series of selective HCN1 blockers", Bioorganic & Medicinal Chemistry Letters, Pergamon, GB, vol. 21, No. 18, pp. 5197-5201.
K. Nagarajan et al., 1992, "Synthesis of trans-N-2-aryl (heteryl) ethenamidines", Proc. Indian Acad. Sci., pp. 383-397.
CAS Registry No. 1332092-81-5; Sep. 14, 2011.
CAS Registry No. 1216806-56-2; Apr. 5, 2010.
CAS Registry No. 1216441-98-3; 1216422-89-7; 1216386-06-09, 1216376-74-7; Apr. 4, 2010.
CAS Registry No. 1215760-45-4; 1215735-65-1; Apr. 2, 2010.
CAS Registry No. 1215381-82-0; Apr. 1, 2010.
CAS Registry No. 862827-12-1; Sep. 9, 2005.
CAS Registry No. 1244856-29-8; Oct. 3, 2010.

* cited by examiner

*Primary Examiner* — Rebecca Anderson
(74) *Attorney, Agent, or Firm* — Mary Catherine Di Nunzio

(57) ABSTRACT

The present invention is directed to novel cyclic amines which inhibit the P2X$_7$ receptor.

24 Claims, No Drawings

CYCLIC AMINES

FIELD OF THE INVENTION

The present invention is directed to novel compounds which inhibit the P2X₇ receptor. Separate aspects of the invention are directed to pharmaceutical compositions comprising said compounds and uses of the compounds to treat pain, inflammation, neurological disorders, or neuropsychiatric disorders.

BACKGROUND ART

The purinergic 2X₇ (P2X₇) receptor is a ligand-gated ion channel which is activated by extracellular ATP and is present on a variety of cell types, including microglia in the central nervous system and other cells involved in inflammation and immune system function. The P2X₇ receptor has been shown to have a role in cytolysis in the immune system (Surprenant, et al. Science, 272, 735-41, 1996), and is involved in activation of lymphocytes and monocyte/macrophages leading to the increased release of pro-inflammatory cytokines (e.g., TNFα and IL1β) from these cells (Ferrari, et al. Neuropharmacol, 36, 1295-301, 1997).

Studies have shown that inhibiting P2X₇ receptor activation in situations of inflammation (e.g., rheumatoid arthritis and other autoimmune diseases, osteoarthritis, asthma, chronic obstructive pulmonary disease and inflammatory bowel disease) or interstitial fibrosis results in a therapeutic effect (DiVirgilio, et al. Drug Dev Res, 45, 207-13, 1998). These and other studies indicate that P2X₇ receptor antagonists may find use in the treatment and prophylaxis of pain, including acute, chronic and neuropathic pain (Chessel, et al, Pain, 114, 386-96, 2005).

Inhibiting P2X₇ activation may also diminish or reduce cell death caused by prolongation of activated P2X₇ receptors, indicating a potential therapeutic intervention for said antagonists in nervous system injury or degeneration (Sperlagh, et al., Progress in Neurobiology, 7, 327-346, 2006). Vianna, et al. (Epilepsia, 43, 27-229, 2002) also revealed a potential role for P2X₇ receptors in the pathogenesis of epilepsy. Interestingly, because of the P2X₇ receptor's role in microglia activation and proliferation in the central nervous system (CNS), a self-propagating cycle of neuroinflammation and neurodegeneration results from P2X₇ receptor activation in areas of the brain (Monif, et al, J Neurosci, 29, 3781-91, 2009).

Thus, P2X₇ receptor antagonists, particularly small molecules with sufficient brain-penetrable properties, are desirable as useful agents for therapeutic intervention in the central nervous system for treating pain, inflammation, neurological and neurodegenerative disorders, neuropsychiatric disorders, or other disorders for which the reduction or otherwise stabilization of pro-inflammatory cytokines is beneficial. The present invention fulfills this need, and provides further related advantages.

SUMMARY OF THE INVENTION

An objective of the present invention is to provide compounds that inhibit P2X₇ receptors. Accordingly, the present invention relates to compounds of Formula I.

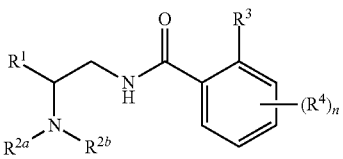

Formula I wherein $R^1$ is phenyl, pyridyl, pyrazinyl, pyridazinyl, pyrimidyl or 5 membered heteroaryl, each of which is optionally substituted with one or more $C_{1-6}$ alkyl, halogen, hydroxy, $C_{1-4}$ fluoroalkyl, $C_{3-6}$ cycloalkyl, $C_{1-6}$ alkoxy, $C_{1-6}$ fluoroalkoxy, cyano or $-SO_2R^7$;

wherein $R^{2a}$ and $R^{2b}$ combine with the nitrogen to which they are attached to form piperazinyl, piperidinyl, morpholinyl, pyrrolidinyl, pyrrolo, imidazo, azetidinyl, 6 to 10 membered spiro(heterocyclyl), homomorpholinyl, homopiperidinyl or homopiperazinyl each of which is optionally substituted with one or more $C_{1-6}$ alkyl, $C_{1-6}$ alkenyl, $C_{3-6}$-cycloalkyl, $C_{1-6}$ alkoxy, oxo, $-NR^5R^6$ or fluorine;

wherein $R^3$ is halogen, $C_{1-4}$-fluoroalkyl, cyano, cyclopropyl, $C_{1-4}$alkyloxy, $C_{1-4}$fluoroalkyloxy, $-SO_2R^7$, $-NR^5R^6$ or $C_{1-6}$alkyl;

wherein $R^4$ is halogen, $C_{1-6}$ alkyl, $C_{1-4}$ fluoroalkyl, cyano, $-SO_2R^8$, $-NR^5R^6$, $C_{1-6}$ alkoxy, $C_{1-4}$ fluoroalkoxy or $C_{3-6}$-cycloalkyl;

wherein $R^5$ and $R^6$ independently of each other are hydrogen or $C_{1-6}$ alkyl;

wherein $R^7$ is $C_{1-6}$ alkyl, $C_{3-6}$cycloalkyl, $C_{1-4}$ fluoroalkyl; and wherein n is 0-3; or a pharmaceutically acceptable salt thereof.

The invention also provides a pharmaceutical composition comprising a compound of the invention or a pharmaceutically acceptable salt thereof, and optionally a pharmaceutically acceptable carrier, excipient or diluent.

The compounds of Formula I may contain one or more stereogenic or asymmetric centers, such as one or more asymmetric carbon atoms. The compounds of Formula I may thus be present as mixtures of stereoisomers or preferably as pure stereoisomers. Mixtures of stereoisomers can be separated in a manner known to a person skilled in the art.

The present invention further provides methods for treating pain or inflammation in a subject, comprising administering to a subject suffering from pain or inflammation a therapeutically effective amount of a compound of Formula I.

The present invention further provides methods for treating an affective disorder in a subject comprising administering to a subject suffering from an affective disorder a therapeutically effective amount of at least one compound of Formula I.

The present invention further provides methods for treating a neurological disorder or neurodegenerative disorder in a subject comprising administering to a subject suffering from a neurological disorder or neurodegenerative disorder a therapeutically effective amount of at least one compound of Formula I.

The present invention further provides methods for treating depression, major depressive disorder, treatment resistant depression, anxiety, obsessive-compulsive disorder, post-traumatic stress disorder (PTSD), neuropathic pain, osteoarthritis, rheumatoid arthritis, psoriatic arthritis, inflammatory bowel disease, multiple sclerosis, epilepsy, Parkinson's Disease, Huntington's Disease and Alzheimer's disease, which involves administering a compound of Formula I.

The present invention also provides the use a compound of Formula I for the manufacture of a medicament for the treatment of affective disorders.

The present invention also provides a compound of Formula I for use in treating an affective disorder in a subject.

These and other aspects of the invention will become apparent upon reference to the following detailed description.

DETAILED DESCRIPTION OF THE INVENTION

As previously indicated, the present invention is based on the discovery of the compounds of Formula I, which are inhibitors of the $P2X_7$ receptor, and as such, are useful for the treatment of related disorders. Additionally, certain aspects of the invention are explained in greater detail below but this description is not intended to be a detailed catalog of all the different ways in which the invention may be implemented, or all the features that may be added to the instant invention. Hence, the following specification is intended to illustrate some embodiments of the invention, and not to exhaustively specify all permutations, combinations and variations thereof.

In one embodiment, $R^1$ is optionally substituted phenyl.

In one embodiment, $R^1$ is optionally substituted pyridyl.

In another embodiment, $R^1$ is optionally substituted pyrazinyl.

In one embodiment, $R^1$ is optionally substituted pyrimidyl.

In one embodiment, $R^1$ is optionally substituted 5 membered heteroaryl.

In one embodiment, $R^{2a}$ and $R^{2b}$ combine with the nitrogen to which they are attached to form optionally substituted piperazinyl.

In yet embodiment, $R^{2a}$ and $R^{2b}$ combine with the nitrogen to which they are attached to form optionally substituted piperidinyl.

In one embodiment, $R^{2a}$ and $R^{2b}$ combine with the nitrogen to which they are attached to form optionally substituted morpholinyl.

In one embodiment, $R^{2a}$ and $R^{2b}$ combine with the nitrogen to which they are attached to form optionally substituted pyrrolidinyl.

In one embodiment, $R^{2a}$ and $R^{2b}$ combine with the nitrogen to which they are attached to form optionally substituted pyrrolo.

In one embodiment, $R^{2a}$ and $R^{2b}$ combine with the nitrogen to which they are attached to form optionally substituted imidazo.

In one embodiment, $R^{2a}$ and $R^{2b}$ combine with the nitrogen to which they are attached to form optionally substituted 6 to 10 membered spiro(heterocyclyl).

In one embodiment, $R^{2a}$ and $R^{2b}$ combine with the nitrogen to which they are attached to form optionally substituted homomorpholinyl In one embodiment, $R^{2a}$ and $R^{2b}$ combine with the nitrogen to which they are attached to form optionally substituted homopiperidinyl In one embodiment, $R^{2a}$ and $R^{2b}$ combine with the nitrogen to which they are attached to form optionally substituted homopiperazinyl In one embodiment, $R^{2a}$ and $R^{2b}$ combine with the nitrogen to which they are attached to form optionally substituted azetidinyl.

In one embodiment, $R^3$ is chlorine, methyl or trifluoromethyl.

In one embodiment, n is 0.

In one embodiment, n is 1.

In one embodiment, n is 2.

In one embodiment, $R^4$ is fluorine, chlorine, $C_{1-3}$ alkyl, $C_{1-4}$ fluoroalkyl, cyano, $C_{1-3}$ alkoxy or $C_{1-4}$ fluoroalkoxy.

As used herein, the term "$C_1$-$C_6$ alkyl" refers to a straight chained or branched saturated hydrocarbon having from one to six carbon atoms inclusive. Examples of such substituents include, but are not limited to, methyl, ethyl, 1-propyl, 2-propyl, 1-butyl, 2-butyl, 2-methyl-2-propyl, 2-methyl-1-propyl, n-pentyl and n-hexyl. Similarly, the term "straight chained or branched $C_1$-$C_3$ alkyl" refers to a saturated hydrocarbon having from one to three carbon atoms inclusive. Examples of such substituents include, but are not limited to, methyl, ethyl and n-propyl.

Likewise, the term "$C_1$-$C_6$ alkoxy" refers to a straight chained or branched saturated alkoxy group having from one to six carbon atoms inclusive with the open valency on the oxygen. Examples of such substituents include, but are not limited to, methoxy, ethoxy, n-butoxy, t-butoxy and n-hexyloxy.

As used herein, the term "$C_1$-$C_4$ fluoroalkyl" refers to a straight chained or branched saturated hydrocarbon having from one to four carbon atoms inclusive substituted with one or more fluorine atoms. Examples of such substituents include, but are not limited to, trifluoromethyl, pentafluoroethyl, 1-fluoroethyl, monofluoromethyl, difluoromethyl and 1,2-difluoroethyl.

Likewise, the term "$C_1$-$C_4$ fluoroalkoxy" refers to a straight chained or branched saturated alkoxy group having from one to four carbon atoms inclusive with the open valency on the oxygen and in which one or more carbon atoms are substituted with one or more fluorine atoms. Examples of such substituents include, but are not limited to, monofluoromethoxy, 1,1-difluoroethoxy and 1-monofluoro-n-butoxy.

Likewise the term "$C_{3-6}$ cycloalkyl" refers to saturated monocyclic hydrocarbon groups. Examples of such systems include, but are not limited to, cyclopropyl, cyclobutyl or cyclohexyl Likewise the term "5 membered heteroaryl" refers to a fully unsaturated aromatic monocyclic ring system having 1-4 heteroatoms. Examples of such systems include, but are not limited to, thienyl, furyl, imidazolyl and pyrrolyl.

Likewise the term "6 to 10 membered spiro(heterocyclyl)" refers to a heterocyclic ring which is a fused bicyclic system. Examples of such systems include, but are not limited to, 2-oxa-6-aza-spiro[3.3]heptane, 2-aza-spiro[3.3]heptane and 2,6-diaza-spiro[3.3]heptane.

The term "halogen" refers to fluorine, chlorine, bromine and iodine.

As used herein, the phrase "effective amount" when applied to a compound of the invention, is intended to denote an amount sufficient to cause an intended biological effect. The phrase "therapeutically effective amount" when applied to a compound of the invention is intended to denote an amount of the compound that is sufficient to ameliorate, palliate, stabilize, reverse, slow or delay the progression of a disorder or disease state, or of a symptom of the disorder or disease. In an embodiment, the method of the present invention provides for administration of combinations of compounds. In such instances, the "effective amount" is the amount of the combination sufficient to cause the intended biological effect.

The term "treatment" or "treating" as used herein means ameliorating or reversing the progress or severity of a disease or disorder, or ameliorating or reversing one or more symptoms or side effects of such disease or disorder. "Treatment" or "treating", as used herein, also means to inhibit or block, as in retard, arrest, restrain, impede or obstruct, the progress of a system, condition or state of a disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of a disease or disorder state, amelioration or palliation of a disease or disorder state, and remission of a disease or disorder, whether partial or total, detectable or undetectable.

Pharmaceutically Acceptable Salts

The present invention also comprises salts of the present compounds, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines (for example, 8-bromotheophylline and the like). Further examples of pharmaceutically acceptable inorganic or organic acid addition salts include the pharmaceutically acceptable salts listed in S. M. Berge, et al., J. Pharm. Sci., 1977, 66, 2.

Furthermore, the compounds of this invention may exist in unsolvated as well as in solvated forms with pharmaceutically acceptable solvents such as water, ethanol and the like.

Racemic forms may be resolved into the optical antipodes by known methods, for example, by separation of diastereomeric salts thereof with an optically active acid, and liberating the optically active amine compound by treatment with a base. Separation of such diastereomeric salts can be achieved, e.g. by fractional crystallization. The optically active acids suitable for this purpose may include, but are not limited to d- or l-tartaric, mandelic or camphorsulfonic acids. Another method for resolving racemates into the optical antipodes is based upon chromatography on an optically active matrix. The compounds of the present invention may also be resolved by the formation and chromatographic separation of diastereomeric derivatives from chiral derivatizing reagents, such as, chiral alkylating or acylating reagents, followed by cleavage of the chiral auxiliary. Any of the above methods may be applied either to resolve the optical antipodes of the compounds of the invention per se or to resolve the optical antipodes of synthetic intermediates, which can then be converted by methods described herein into the optically resolved final products which are the compounds of the invention.

Additional methods for the resolution of optical isomers, known to those skilled in the art, may be used. Such methods include those discussed by J. Jaques, A. Collet and S. Wilen in Enantiomers, Racemates, and Resolutions, John Wiley and Sons, New York, 1981. Optically active compounds can also be prepared from optically active starting materials.

Pharmaceutical Compositions

The present invention further provides a pharmaceutical composition comprising a therapeutically effective amount of a compound of Formula I and a pharmaceutically acceptable carrier. The present invention also provides a pharmaceutical composition comprising a therapeutically effective amount of one of the specific compounds disclosed in the Experimental Section and a pharmaceutically acceptable carrier.

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by an oral route. Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art. Liquid dosage forms for oral administration include solutions, emulsions, suspensions, syrups and elixirs.

The term "inhibit" or "inhibiting" as used herein means to reduce, diminish, block or even eliminate, such as in e.g. "inhibiting P2X$_7$ receptor activity". "Inhibiting P2X$_7$ receptor activity" or "inhibiting P2X$_7$ activity" as used herein means, e.g. reducing or even eliminating the ability of a P2X$_7$ receptor to exhibit a cellular response, such as inhibiting the response to stimuli or agonist ligands, or inhibiting the production or accumulation of IL1β.

The present invention also provides a method of treating a disease or disorder, the method comprising administering a therapeutically effective amount of at least one compound of the present invention or a pharmaceutically acceptable salt thereof to a mammal suffering from (or at risk for) the disease or disorder, or otherwise in need of the treatment. The present invention also provides a method of treating pain or inflammation, the method comprising administering a therapeutically effective amount of at least one compound of the present invention or a pharmaceutically acceptable salt thereof to a mammal in need thereof. In an embodiment, the pain that may be treated using the compounds described herein, including acute, chronic or inflammatory pain, is caused by neuropathic pain, post-operative pain, morphine tolerance, fibromyalgia, neuralgias, headache, osteoarthritis, rheumatoid arthritis, psoriatic arthritis, irritable bowel syndrome or inflammatory bowel disease.

In other embodiments, the disease or disorder that may be treated using the compounds described herein is a neurological disorder or neurodegenerative disorder, such as epilepsy, multiple sclerosis, Parkinson's disease, Huntington's disease or Alzheimer's disease. As used herein, the term "neurological disorder" means a disorder of the nervous system, and includes, but is not limited to, the disorders as described hereinabove. Based on the well-known meaning of disorders of the nervous system, neurological disorders result from structural, biochemical, electrical, or cellular (neuronal or microglial) signaling abnormalities that may occur in the brain or spinal cord of the afflicted mammal. As used herein, the term "neurodegenerative disorder" means a disorder characterized by symmetrical and progressive loss of structure or function of neurons, such as death of neurons or reduced growth of neurons. Such loss of neurons may affect motor, sensory, or cognitive neuronal systems. As such, treating a neurological or neurodegenerative disorder using the compounds described herein may result in the amelioration or relief of symptoms of the neurological or neurodegenerative disorder, such symptoms as paralysis, muscle weakness, poor coordination, uncontrolled movements, seizures, confusion, altered levels of consciousness, memory loss, emotional instability, loss of sensation, pain, and similar symptoms.

In an embodiment, the disease or disorder is a neuropsychiatric disorder, such as an affective disorder. As used herein, "affective disorder" means a mental disorder characterized by a consistent, pervasive alteration of mood, and affecting thoughts, emotions and behaviors. Affective disorders include mood disorders as described in DSM-IV-TR® (American Psychiatric Association, 2000, *Diagnostic and Statistical Manual of Mental Disorders* (4th ed., text rev.) doi:10.1176/appi.books.9780890423349; which is incorporated by reference herein). As such, treating an affective disorder using the compounds described herein may result in the amelioration, stabilization or otherwise diminishment or relief of symptoms of the affective disorder, such symptoms as mood instability, manic episodes, feelings of guilt or worthlessness, sleep disturbances, agitation, or the like. Examples of affective disorders include, but are not limited to, depressive disorders, anxiety disorders, bipolar disorders, dysthymia and schizoaffective disorders. Anxiety disorders include, but are not limited to, generalized anxiety disorder, panic disorder, obsessive-compulsive disorder, phobias, and post-traumatic stress disorder (PTSD). Depressive disorders include, but are not limited to, major depressive disorder (MDD), catatonic depression, melancholic depression, atypical depression, psychotic depression, postpartum depression, treatment-resistant depression, bipolar depression, including bipolar I and bipolar II, and mild, moderate or severe depression. Personality disorders include, but are not limited to, paranoia, antisocial and borderline personality disorders.

In an embodiment of the invention, the affective disorder treated using the compounds described herein is depression, major depressive disorder (MDD), treatment-resistant depression, bipolar disorder, generalized anxiety disorder, panic disorder, obsessive-compulsive disorder, or post-traumatic stress disorder (PTSD), or a combination thereof.

The present invention provides a method of treating an affective disorder in a subject, comprising administering to a subject in need of such treatment a therapeutically effective amount of at least one compound of Formula I.

The present invention provides a method of inhibiting $P2X_7$ activity in a subject, comprising administering to a subject in need thereof a therapeutically effective amount of at least one compound of Formula I.

The present invention also provides a method of inhibiting production or accumulation of IL1β, comprising administering to a subject in need of such treatment a therapeutically effective amount of at least one compound of Formula I.

In an embodiment, the present invention provides the use of a compound of Formula I for the manufacture of a medicament for the treatment of affective disorders. The present invention also provides the use of a compound of Formula I for the manufacture of a medicament for the inhibition of $P2X_7$ activity. The present invention further provides the use of a compound of Formula I for the manufacture of a medicament for the inhibition of production or accumulation of IL1β.

In an embodiment, the present invention provides at least one compound of Formula I for use in treating an affective disorder in a subject. In an embodiment, the present invention provides at least one compound of Formula I for use in inhibiting $P2X_7$ activity in a subject. In an embodiment, the present invention provides at least one compound of Formula I for use in inhibiting production or accumulation of IL1β in a subject.

The invention also provides a compound of Formula I for use in therapy of a subject, for example, in the treatment of affective disorders.

Experimental Section

The compounds of the present invention of the general formula I, wherein $R^1$, $R^{2a}$, $R^{2b}$, $R^3$, $R^4$ and n are as defined above can be prepared by the methods outlined in the following reaction scheme 1 and in the examples. In the described methods, it is possible to make use of variants or modifications, which are themselves known to chemists skilled in the art or could be apparent to the person of ordinary skill in this art. Furthermore, other methods for preparing compounds of the invention will be readily apparent to the person skilled in the art in light of the following reaction schemes and examples.

The schemes may involve the use of selective protecting groups during the synthesis of the compounds of the invention. One skilled in the art would be able to select the appropriate protecting group for a particular reaction. It may be necessary to incorporate protection and de-protection strategies for substituents such as amino, amino, carboxylic acid and hydroxyl groups in the synthetic methods described below to synthesize the compounds of Formula I. Methods for protection and de-protection of such groups are well known in the art, and may be found in T. Green, et al., Protective Groups in Organic Synthesis, 1991, $2^{nd}$ Edition, John Wiley & Sons, New York.

General Methods

Analytical LC-MS data were obtained using one of the methods identified below

Method A: Performed using electrospray ionization (ESI) operating in positive mode via a Waters ZQ (Waters Corp.) mass spectrometer (all from Waters Corp., Milford, Mass., USA), an Agilent 1100 LC pump (Agilent Technologies, Inc., Santa Clara, Calif.), and Agilent 1100 autosampler, with a 200 µl/min split to the ESI source with inline Agilent 1100 diode array detector (DAD) and variable wavelength detector (VWD) at 254 nm, and an 800 uL/min split to a Waters evaporative light scattering detector (ELSD). Separation was performed on a Inertsil ODS-3 3 µm 50×4.6 mm column using a mobile phase of A) water 1% acetonitrile and 0.2% ammonium formate; and B) Acetonitrile, which was delivered in a gradient fashion over 1.70 minutes going from 20% B to 85% B. Then stepped to 100% B at 1.85 minutes and maintained at 100% B until 1.99 minutes.

Method B: A PE Sciex API 150EX instrument equipped with atmospheric pressure photo ionisation and a Shimadzu LC-8A/SLC-10A LC system was used. Column: 3.0×30 mm Waters Symmetry C18 column with 2.2 µm particle size; Column temperature: 50° C.; Solvent system: A=water/trifluoroacetic acid (99.965:0.035) and B=acetonitrile/trifluoroacetic acid (99.965:0.035); Method: Linear gradient elution with A:B=90:10 to 20:80 in 1.5 minutes and with a flow rate of 1.2 mL/min.

Method C: A PE Sciex API 150EX instrument equipped with atmospheric pressure photo ionisation and a Shimadzu LC-8A/SLC-10A LC system was used. Column: 3.0×30 mm Waters Symmetry C18 column with 2.2 µm particle size; Column temperature: 50° C.; Solvent system: A=water/trifluoroacetic acid (99.965:0.035) and B=acetonitrile/trifluoroacetic acid (99.965:0.035); Method: Linear gradient elution with A:B=100:0 to 70:30 in 1.5 minutes and with a flow rate of 1.2 mL/min.

Method D: A Waters Acquity UPLC-MS was used. Column: Acquity UPLC BEH C18 1.7 µm; 2.1×50 mm; Column temperature: 60° C.; Solvent system: A=water/trifluoroacetic acid (99.965:0.035) and B=acetonitrile/water/trifluoroacetic acid (94.965:5:0.035); Method: Linear gradient elution with A:B=90:10 to 0:100 in 1.0 minutes and with a flow rate of 1.2 mL/min.

Method E: An Agilent 1200 LCIS system with ELS detector was used. Column: Agilent TC-C18 5 µm; 2.1×50 mm; Column temperature: 50° C.; Solvent system: A=water/trifluoroacetic acid (99.9:0.1) and B=acetonitrile/trifluoroacctic acid (99.95:0.05); Method: Linear gradient elution with A:B=99:1 to 0:100 in 4.0 minutes and with a flow rate of 0.8 mL/min.

Method F: A Waters Acquity UPLC-MS was used. Column: Acquity UPLC BEH C18 1.7 µm; 2.1×50 mm; Column temperature: 60° C.; Solvent system: A=water/trifluoroacetic acid (99.965:0.035) and B=acetonitrile/water/trifluoroacetic acid (94.965:5:0.035); Method: Linear gradient elution with A:B=98:2 to 0:100 in 1.0 minutes and with a flow rate of 1.2 mL/min.

Method G: An Agilent 1200 LCMS system with ELS detector was used. Column: Agilent TC-C18 5 µm; 2.1×50 mm; Column temperature: 50° C.; Solvent system: A=water/trifluoroacetic acid (99.9:0.1) and B=acetonitrile/trifluoroacetic acid (99.95:0.05); Method: Linear gradient elution with A:B=90:10 to 0:100 in 4.0 minutes and with a flow rate of 0.8 mL/min.

Method H: A Waters Acquity UPLC-MS was used. Column: Acquity UPLC BEH C18 1.7 µm; 2.1×50 mm; Column temperature: 60° C.; Solvent system: A=water/formic acid (99.9:0.1) and B=acetonitrile/water/formic acid (94.9:5:0.1); Method: Linear gradient elution with A:B=90:10 to 0:100 in 1.0 minutes and with a flow rate of 1.2 mL/min.

Method I: An Agilent 1200 LCMS system with ELS detector was used. Column: Waters XBridge Shield RP18 5 µm; 2.1×50 mm; Column temperature: 40° C.; Solvent system: A=water/ammonia (99.95:0.05) and B=acetonitrile; Method: Linear gradient elution with A:B=95:5 to 0:100 in 4.0 minutes and with a flow rate of 0.8 mL/min.

Preparative LC-MS-purification was performed on a PE Sciex API 150EX instrument with atmospheric pressure chemical ionization. Column: 50×20 mm YMC ODS-A with 5 µm particle size; Solvent system: A=water/trifluoroacetic acid (99.965:0.035) and B=acetonitrile/water/trifluoroacetic acid (94.965:5:0.035); Method: Linear gradient elution with A:B=80:20 to 0:100 in 7 minutes and with a flow rate of 22.7 mL/minute. Fraction collection was performed by split-flow MS detection.

Preparative SFC was performed on a Thar 80 instrument. Exemplified conditions can be, but not limited to: Column AD 250×30 mm with 20 µm particle size; Column temperature: 38° C., Mobile phase: Supercritical CO$_2$/EtOH (0.2% NH$_3$H$_2$O)=45155.

$^1$H NMR spectra were recorded at 300, 400, 500 or 600 MHz on Bruker Avance instruments. TMS was used as internal reference standard. Chemical shift values are expressed in ppm. The following abbreviations are used for multiplicity of NMR signals: s=singlet, d=doublet, t=triplet, q=quartet, qui=quintet, h=heptet, dd=double doublet, dt=double triplet, dq=double quartet, tt=triplet of triplets, m=multiplet, br s=broad singlet and br=broad signal.

Benzoic acids of formula II are commercially available or available by methods described in the literature (see for example Shaikh, Tanveer Mahammad Ali, *J. Org. Chem* (2006), 71, 5043-5046 and Mongin, Florence; Tetrahedron Lett. (1996), 37, 6551-6554).

Abbreviations are in accordance with to the ACS Style Guide: "The ACS Style guide—A manual for authors and editors" Janet S. Dodd, Ed. 1997, ISBN: 0841234620

Preparation of Intermediates

2-Trifluoromethyl-pyrimidine-5-carbaldehyde

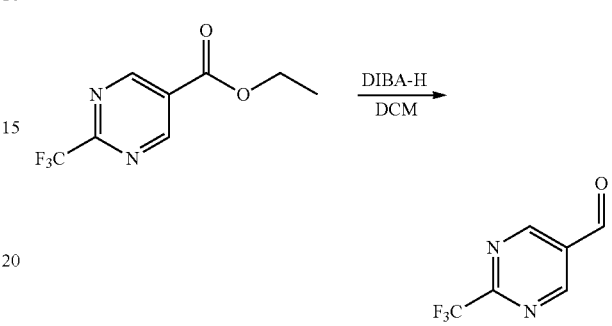

To a solution of ethyl 2-trifluoromethyl-pyrimidine-5-carboxylate (1 g, 5 mmol) in DCM (23 mL) at –78° C. was added DIBAL-H (6 ml, 6 mmol, 1.0 M solution in toluene) slowly and stirred at the same temperature for 3 h. The mixture was quenched with slow addition of 2M hydrochloric acid and warmed to room temperature. The mixture was extracted with EtOAc (3×20 mL). The combined organic extracts were dried over sodium sulfate, filtered and concentrated to give the title compound (572 mg, yield: 71.5%). $^1$H NMR (CDCl$_3$ 400 MHz): δppm 10.27 (s, 1H), 9.35 (s, 2H).

Morpholin-4-yl-(2-trifluoromethyl-pyrimidin-5-yl)-acetonitrile

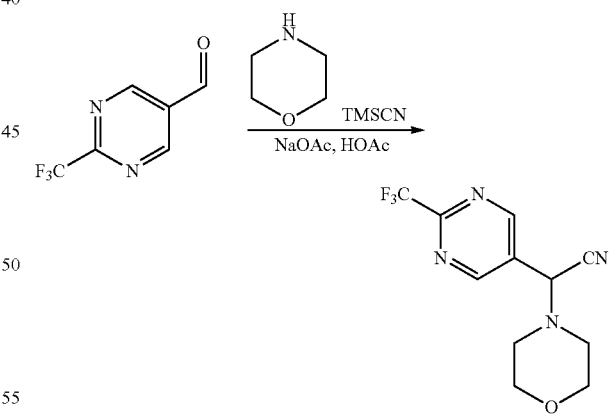

To a mixture of 2-trifluoromethyl-pyrimidine-5-carbaldehyde (572 mg, 3.25 mmol) and TMSCN (645 mg, 6.49 mmol) in HOAc (10 ml) was added dropwise morpholine (311 mg, 3.57 mmol), followed by NaOAc (320 mg, 3.90 mmol). The mixture was stirred at room temperature overnight. The solvent was removed in vacuum. The residue was basified by addition of sat. aq. NaHCO$_3$ solution to pH 8; then extracted with EtOAc (3×10 mL). The combined organic layers were washed with brine, dried over anhydrous sodium sulfate, filtered and evaporated to yield the title compound (591 mg, yield: 67%). ¹H NMR (CDCl₃ 400 MHz): δppm 9.10 (s, 2H), 4.96 (s, 1H), 3.88-3.71 (m, 4H), 2.79-2.55 (m, 4H).

2-Morpholin-4-yl-2-(2-trifluoromethyl-pyrimidin-5-yl)-ethylamine

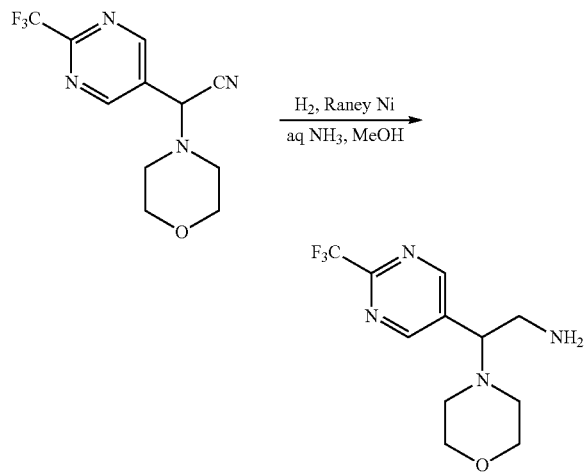

A mixture of morpholin-4-yl-(2-trifluoromethyl-pyrimidin-5-yl)-acetonitrile (200 mg, 0.735 mmol), Raney-Ni (200 mg), NH₃ (aq) (1.5 mL) in MeOH (20 mL) was degassed and purged with Ar and H₂ each 3 times. The mixture was stirred at room temperature under H₂ (30 psi) for 25 minutes. The resulting mixture was filtered and the filtrate was concentrated under reduced pressure to yield the title compound (175 mg, yield: 86%). ¹H NMR (CDCl₃ 400 MHz): δppm 8.83 (s, 2H), 3.80-3.61 (m, 4H), 3.44 (t, J=5.2 Hz, 1H), 3.19-2.99 (m, 2H), 2.52-2.35 (m, 4H).

The following intermediates were prepared in a similar way:
2-Morpholin-4-yl-2-pyridin-2-yl-ethylamine;
2-Morpholin-4-yl-2-pyridin-3-yl-ethylamine;
2-Morpholin-4-yl-2-pyridin-4-yl-ethylamine;
2-(4-Fluoro-phenyl)-2-morpholin-4-yl-ethylamine;
2-(4-Chloro-phenyl)-2-morpholin-4-yl-ethylamine;
2-(4-Methoxy-phenyl)-2-morpholin-4-yl-ethylamine;
2-(4-Methyl-phenyl)-2-morpholin-4-yl-ethylamine;
2-(4-Methoxy-phenyl)-2-piperidin-1-yl-ethylamine;
2-Azetidin-1-yl-2-(4-chloro-phenyl)-ethylamine;
2-(6-Cyclopropyl-pyridin-3-yl)-2-morpholin-4-yl-ethylamine;
2-Morpholin-4-yl-2-(6-trifluoromethyl-pyridin-3-yl)-ethylamine;
2-(6-Chloro-pyridin-3-yl)-2-morpholin-4-yl-ethylamine;
2-Morpholin-4-yl-2-pyrimidin-5-yl-ethylamine;
2-(2-Methyl-pyrimidin-5-yl)-2-morpholin-4-yl-ethylamine;
2-(6-Methyl-pyridin-3-yl)-2-morpholin-4-yl-ethylamine;
2-(4-Chloro-phenyl)-2-(4,4-difluoro-piperidin-1-yl)-ethylamine;
2-(4-Fluoro-phenyl)-2-(4,4-difluoro-piperidin-1-yl)-ethylamine;
2-(4,4-Difluoro-piperidin-1-yl)-2-(4-methoxy-phenyl)-ethylamine;
2-(4,4-Difluoro-piperidin-1-yl)-2-(6-fluoro-pyridin-3-yl)-ethylamine;
2-(4,4-Difluoro-piperidin-1-yl)-2-(6-trifluoromethyl-pyridin-3-yl)-ethylamine;
2-(4,4-difluoropiperidin-1-yl)-2-(2-methylpyrimidin-5-yl)ethanamine;
2-(4,4-difluoropiperidin-1-yl)-2-(2-(trifluoromethyl)pyrimidin-5-yl)ethanamine;
2-(4,4-dimethylpiperidin-1-yl)-2-(2-(trifluoromethyl)pyrimidin-5-yl)ethanamine;
2-morpholino-2-(2-(trifluoromethyl)pyrimidin-5-yl)ethanamine;
2-(3,3-difluoropiperidin-1-yl)-2-(2-methylpyrimidin-5-yl)ethanamine;
2-(4-fluoropiperidin-1-yl)-2-(2-methylpyrimidin-5-yl)ethanamine;
2-(4-fluoropiperidin-1-yl)-2-(2-(trifluoromethyl)pyrimidin-5-yl)ethanamine;
2-(4,4-difluoropiperidin-1-yl)-2-(1-methyl-1H-pyrazol-4-yl)ethanamine;
2-(2-methylpyrimidin-5-yl)-2-(piperidin-1-yl)ethanamine;
2-(4,4-difluoropiperidin-1-yl)-2-(2-ethylpyrimidin-5-yl)ethanamine;
2-(4-methoxypiperidin-1-yl)-2-(2-methylpyrimidin-5-yl)ethanamine;
2-(4-chloropiperidin-1-yl)-2-(2-methylpyrimidin-5-yl)ethanamine;
2-(4-chlorophenyl)-2-(1,4-oxazepan-4-yl)ethanamine;
2-(3-methylpiperidin-1-yl)-2-(2-methylpyrimidin-5-yl)ethanamine;
2-(2-methylpyrimidin-5-yl)-2-(1,4-oxazepan-4-yl)ethanamine;
2-(2-methylpyrimidin-5-yl)-2-(3-methylpyrrolidin-1-yl)ethanamine;
2-(2-methylpyrimidin-5-yl)-2-(3,3,4,4-tetrafluoropyrrolidin-1-yl)ethanamine;
2-(4,4-difluoropiperidin-1-yl)-2-(2-methylpyrimidin-5-yl)ethanamine;
2-(2-isopropylpiperidin-1-yl)-2-(2-methylpyrimidin-5-yl)ethanamine;
2-(2-azabicyclo[2.2.1]heptan-2-yl)-2-(2-methylpyrimidin-5-yl)ethanamine;
2-(2-methylpiperidin-1-yl)-2-(2-methylpyrimidin-5-yl)ethanamine;
5-(2-amino-1-(4,4-difluoropiperidin-1-yl)ethyl)-N,N-dimethylpyrimidin-2-amine;
5-(2-amino-1-(4,4-difluoropiperidin-1-yl)ethyl)-1-methylpyridin-2(1H)-one;
1-(2-Amino-1-(2-methylpyrimidin-5-yl)ethyl)piperidin-4-ol;
2-(4-chloropiperidin-1-yl)-2-(2-methylpyrimidin-5-yl)ethanamine;

2-Cyclopropylpyrimidine-5-carbaldehyde

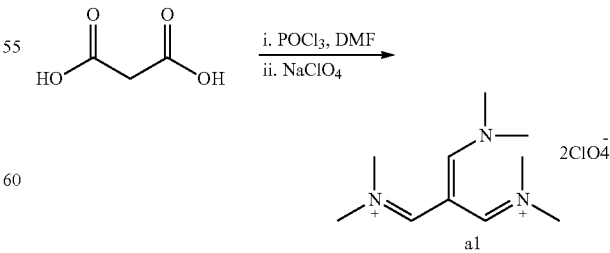

To a three-neck flask (1000 mL) was added dry DMF (85 mL) and POCl₃ (103 g, 0.67 mol) was added drop-wise at room temperature. After the addition was completed, the mixture was stirred for 30 minutes and malonic acid (20 g, 0.19 mol) was added in portions over 40 minutes, keeping the inner temperature below 25° C. The resulting mixture was heated to 90° C. for overnight. The reaction mixture was cooled to room temperature and added into stirring ice-water (80 mL) containing NaClO₄ (53 g, 0.38 mol) in portions, keeping the inner temperature at 0° C. The suspension was filtered; the solid was dried in air to give intermediate a1, which was used in the next step without further purification.

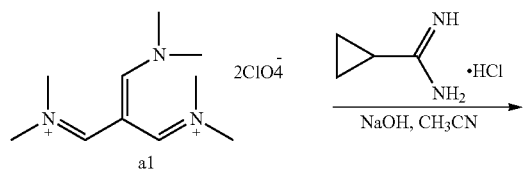

To a mixture of a1 (ca. 0.095 mol) in CH₃CN (300 mL) was added cyclopropanecarboximidamide hydrochloride (12.5 g, 0.105 mol), then sodium hydroxide (7.6 g, 0.19 mol) in water (7.6 mL) was added drop-wise at 0° C. After addition was complete, the resulting mixture was stirred at room temperature overnight. After filtration, the filtrate was concentrated to remove CH₃CN under reduced pressure and the residue water phase was extracted with DCM (3×300 mL). The organic layer was dried over Na₂SO₄, filtered and concentrated in vacuum to give a red oil, which was purified by column chromatography on silica gel (petroleum ether:EtOAc=2:1) to afford 2-cyclopropylpyrimidine-5-carbaldehyde (7.6 g, yield: 53.5%). ¹H NMR (CDCl₃ 400 MHz): δ 10.06 (s, 1H), 8.99 (s, 2H), 2.41-2.35 (m, 1H), 1.32-1.21 (m, 4H).

2-(2-Cyclopropylpyrimidin-5-yl)-2-(4,4-difluoropiperidin-1-yl)acetonitrile

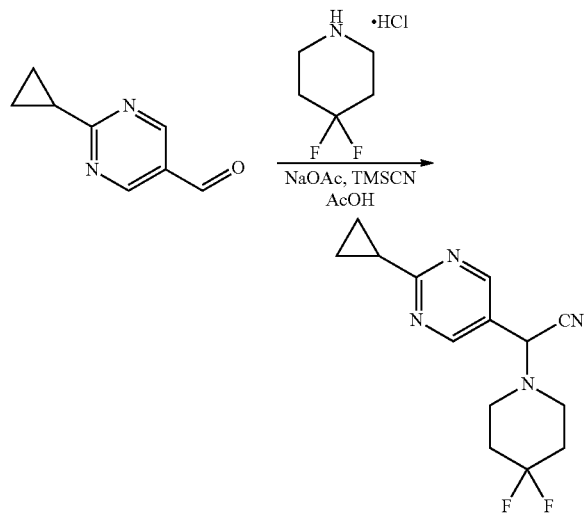

To a solution of 2-cyclopropylpyrimidine-5-carbaldehyde (2 g, 13.5 mmol) and TMSCN (2.68 g, 27 mmol) in AcOH (30 mL) was added 4,4-difluoropiperidine hydrochloride (3.1 g, 13.5 mmol), followed by AcONa (2.66 g, 32.4 mg). The mixture was stirred at 30° C. for overnight. The solvent was removed under reduced pressure and saturated NaHCO₃ (aq) was added to the mixture to pH=8. The resulting mixture was extracted with EtOAc (3×100 mL). The organic layer was dried over Na₂SO₄, filtered and concentrated in vacuum to give the 2-(2-cyclopropylpyrimidin-5-yl)-2-(4,4-difluoropiperidin-1-yl)acetonitrile as a light red solid (3.5 g, 93%), which was used directly for next step without further purification. ¹H NMR (CDCl₃ 400 MHz): δ 8.69 (s, 2H), 4.88 (s, 1H), 2.73-2.70 (t, J=5.5 Hz, 4H), 2.34-2.27 (m, 1H), 2.11-2.00 (m, 4H), 1.19-1.13 (m, 4H).

2-(2-Cyclopropylpyrimidin-5-yl)-2-(4,4-difluoropiperidin-1-yl)ethanamine

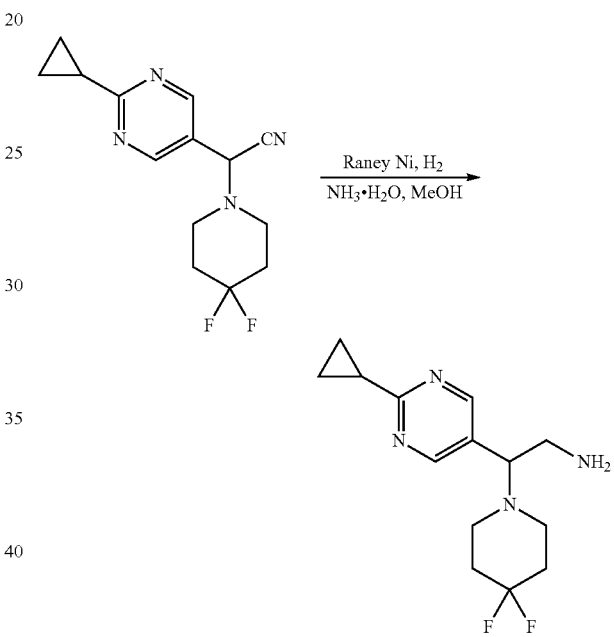

A mixture of 2-(2-cyclopropylpyrimidin-5-yl)-2-(4,4-difluoropiperidin-1-yl)acetonitrile (3.50 g, 126 mmol), Raney Ni (3.50 g) and NH₃H₂O (10 mL) in MeOH (150 mL) was degassed and purged with argon and H₂, then stirred at room temperature under H₂ (50 Psi) for 4 hours. The reaction mixture was filtered and concentrated in vacuum to give 2-(2-cyclopropylpyrimidin-5-yl)-2-(4,4-difluoropiperidin-1-yl)ethanamine as a yellow oil (3.10 g), which was used directly for next step without further purification.

(4-Chloro-phenyl)-pyrrolidin-1-yl-acetonitrile

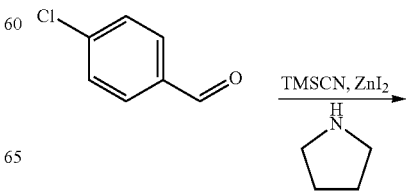

2-(3-methylpiperidin-1-yl)-2-(2-methylpyrimidin-5-yl)ethanamine

Bis(((difluoromethyl)sulfinyl)oxy)zinc (DFMS)

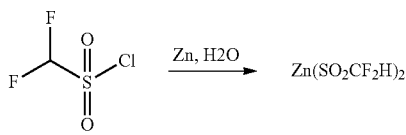

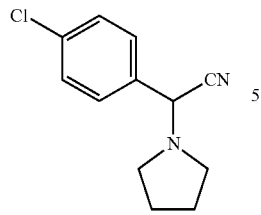

To a solution of 4-Chlorobenzaldehyde (2.50 g, 17.8 mmol) in tetrahydrofuran (15 mL) was added TMSCN (2.4 mL, 18.0 mmol) and Zinc diiodide (30.0 mg, 0.094 mmol) at 0° C. The mixture was stirred at 0° C. for 15 min. To the mixture was added pyrrolidine (1.50 mL, 18.0 mmol) at room temperature. The resultant mixture was stirred at room temperature overnight.

All of the volatiles were removed by rotary evaporator. The residue was dissolved in dichloromethane (100 mL) and was washed with saturated sodium bicarbonate (aq). The organic solution was dried over $MgSO_4$ and concentrated in vacuo.

The crude product was purified by column chromatography on silica gel (petroleum ether: EtOAc=1:0 to 1:1) to afford (4-Chloro-phenyl)-pyrrolidin-1-yl-acetonitrile (3.52 g, yield: 85%). $^1$H NMR (CDCl$_3$ 400 MHz): δ 7.48 (d, 214), 7.39 (d, 2H), 5.02 (s, 2H), 2.67 (m, 2H), 2.61 (m, 2H), 1.84 (m, 4H).

To a vessel equipped with a stir bar, Zn dust (1.8 g, 27.8 mmol) was added $H_2O$ (20 mL). The reaction vessel was then capped, wrapped in aluminum foil and cooled in an ice bath to 0° C. Difluoromethanesulfonyl chloride (5 g, 33.3 mmol) was then added via syringe open to air. The reaction vessel was sealed with cap and the reaction mixture was removed from the ice bath and allowed to warm to room temperature over 2 h. The excess Zn was removed via filtration, washed with EtOAc (3×10 mL), the filtrate was concentrated under reduced pressure. Residual water was removed azeotropically with toluene (3×10 mL) at 45° C., and the resulting pearly yellow powder was further dried under vacuum for an additional 3 h to give bis(((difluoromethyl)sulfinyl)oxy)zinc (DFMS) (4 g, yield: 81.6%), which was used in the next step without purification. $^1$H NMR (DMSO-d$_6$ 400 MHz) δ 5.24 (t, J=56.0 Hz, 1H).

2-Morpholino-2-(pyrimidin-5-yl)acetonitrile

2-(4-chlorophenyl)-2-(pyrrolidin-1-yl)ethanamine

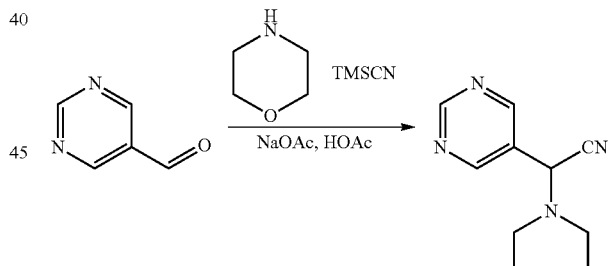

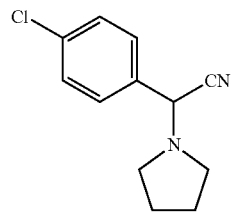

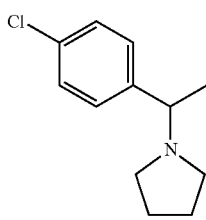

To a solution of (4-Chloro-phenyl)-pyrrolidin-1-yl-acetonitrile (3.52 g, 15.2 mmol; in Tetrahydrofuran (96 mL) was added Lithium tetrahydroaluminate (1225 mg, 32.28 mmol) and the reaction was refluxed over night. The reaction was quenched with $H_2O$ (1.22 ml), 2M NaOH (aq) (1.22 ml) and $H_2O$ (2.44 ml). The solid was filtered off and the reaction was concentrated, to yield 2-(4-chlorophenyl)-2-(pyrrolidin-1-yl)ethanamine (1.14 g, 30% yield).

The following intermediates were prepared in a similar way:

To a mixture of pyrimidine-5-carbaldehyde (2 g, 18.52 mmol) and TMSCN (3.67 g, 37.0 mmol) in HOAc (50 mL) was added morpholine (2.42 g, 27.8 mmol) at room temperature and NaOAc (3.34 g, 40.7 mmol) was followed. The resulting mixture was stirred at room temperature overnight. Saturated aqueous $Na_2CO_3$ solution was added to quench the reaction mixture, the pH was adjusted to about 7 and extracted with EtOAc (3×100 mL). The combined organic layer was washed with brine, dried over $Na_2SO_4$ and concentrated to give crude 2-morpholino-2-(pyrimidin-5-yl)acetonitrile (2.5 g, yield: 66%). $^1$H NMR (CDCl$_3$ 400 MHz): δ9.25 (s, 1H), 8.92 (d, J=10.0 Hz, 2H), 4.87 (s, 1H), 3.79-3.70 (m, 4H), 2.67-2.56 (m, 4H).

2-(2-(Difluoromethyl)pyrimidin-5-yl)-2-morpholinoacetonitrile

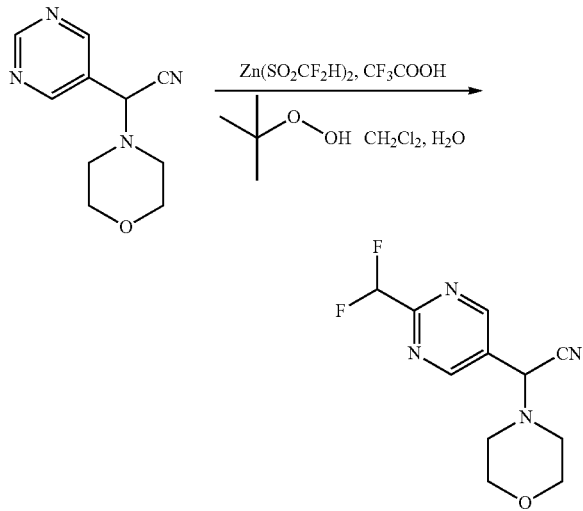

To a solution of 2-morpholino-2-(pyrimidin-5-yl)acetonitrile (1.03 g, 5.04 mmol) and DFMS (4 g, 13.61 mmol) in DCM (40 mL) and H₂O (16 mL) at room temperature was added CF₃COOH (575 mg, 5.04 mmol) followed by slow addition of 2-hydroperoxy-2-methylpropane (3.24 g, 70% solution in H₂O) with vigorous stirring. The reaction mixture was stirred at room temperature overnight. The reaction mixture was portioned between DCM (50 mL) and saturated NaHCO₃ solution (50 mL), the organic layer was separated and the aqueous layer was extracted with DCM (5 mL×3). The organic layer was washed with brine, dried over Na₂SO₄ and concentrated. The crude product was purified by Prep-TLC (Petroleum ether:EtOAc=10:12:1) to give 2-(2-(difluoromethyl)pyrimidin-5-yl)-2-morpholinoacetonitrile (150 mg, yield: 11.7%). $^1$H NMR (CDCl₃ 400 MHz): δ9.01 (d, J=10.0 Hz, 2H), 6.67 (t, J=54.4 Hz, 1H), 4.91 (s, 1H), 3.95-3.62 (m, 4H), 2.81-2.46 (m, 4H).

2-(2-(Difluoromethyl)pyrimidin-5-yl)-2-morpholinoethanamine

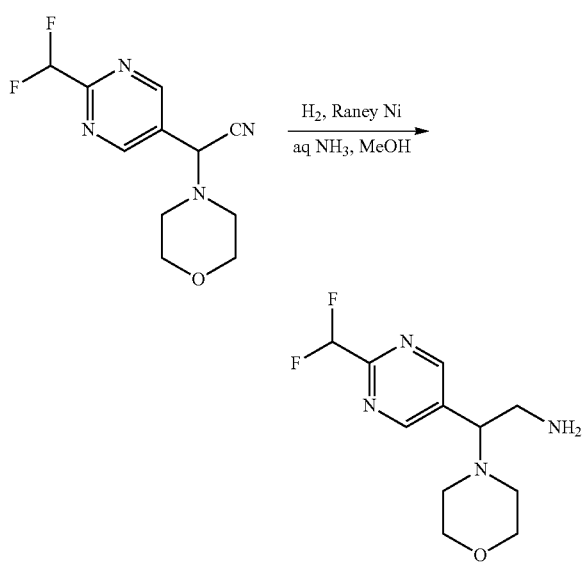

A mixture of 2-(2-(difluoromethyl)pyrimidin-5-yl)-2-morpholinoacetonitrile (150 mg, 0.59 mmol), Raney-Ni (75 mg), NH₃.H₂O (2 mL) in MeOH (20 mL) was degassed and purged with Ar and H₂ each 3 times. The mixture was stirred at room temperature under H₂ (50 psi) for 3 h. The resulting mixture was filtered through celite. The filtrate was concentrated under reduced pressure to give crude 2-(2-(difluoromethyl)pyrimidin-5-yl)-2-morpholinoethanamine, which was used in the next step without further purification.

The following intermediates were prepared in a similar way:

2-(2-(difluoromethyl)pyrimidin-5-yl)-2-(4,4-difluoropiperidin-1-yl)ethanamine;

2-(6-(difluoromethyl)pyridin-5-yl)-2-morpholinoethanamine;

2-(6-(difluoromethyl)pyridin-3-yl)-2-(4,4-difluoropiperidin-1-yl)ethanamine;

5-Bromopyrimidine-2-carbonitrile

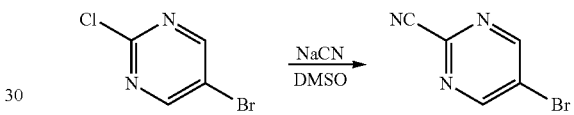

To a solution of NaCN (0.849 g, 17.32 mmol) and DABCO (0.390 g, 3.48 mmol) in a mixture of DMSO (4 ml) and H₂O (9 ml) was added a solution of 5-bromo-2-chloropyrimidine (3.05 g, 15.75 mmol) in DMSO (9 ml). The solution was stirred at room temperature overnight, and then diluted with water, and extracted with EtOAc. The combined organic layer was dried over anhydrous Na₂SO₄ and concentrated to give 5-bromopyrimidine-2-carbonitrile (2.327 g, 12.01 mmol, 76% yield, $^1$H NMR (CDCl₃ 500 MHz): δ 8.94 (s, 2H)).

1-(5-Bromopyrimidin-2-yl)ethanone

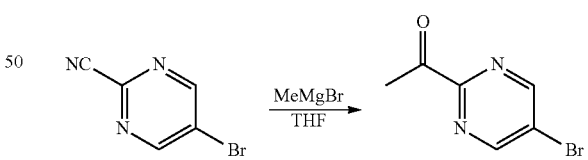

To a solution of 5-bromopyrimidine-2-carbonitrile (221 mg, 1.2 mmol) in THF (10 ml) was added methylmagnesium bromide (3.0 ml, 4.20 mmol, 1.4 molar, THF) at −78° C. under nitrogen. The solution was stirred at −78° C. for 3.5 hours, and then quenched with satd aq NH₄Cl, and extracted with EtOAc. The combined organic layer was dried over anhydrous Na₂SO₄ and concentrated. The reaction was purified by column chromatography on silica gel (petroleum ether: EtOAc=1:0 to 0:1) to afford 1-(5-bromopyrimidin-2-yl)ethanone (1.55 mg, 61% yield). $^1$H NMR (CDCl₃ 500 MHz): δ 9.00 (s, 2H), 2.80 (s, 3H).

5-Bromo-2-(1,1-difluoroethyl)pyrimidine

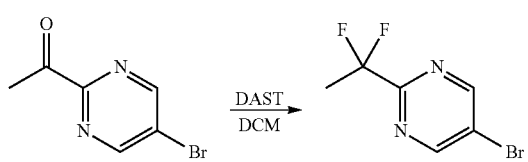

1-(5-bromopyrimidin-2-yl)ethanone (304 mg, 1.514 mmol) in anhydrous DCM (50 ml), under nitrogen, was treated w Diethylaminosulfur trifluoride (1220 mg, 1 ml, 7.57 mmol). After 12 hours of stirring additional Diethylaminosulfur trifluoride (610 mg, 0.5 ml, 3.75 mmol) was added. This was repeated again after 24 hours, Diethylaminosulfur trifluoride (610 mg, 0.5 ml, 3.75 mmol). After 36 hours the reaction was quenched with sat. NaHCO$_3$ and extracted with AcOEt, washed with Brine and dried over Na$_2$SO$_4$, filtered and concentrated. The reaction was purified by column chromatography on silica gel (petroleum ether: EtOAc=1:0 to 0:1) to afford 5-bromo-2-(1,1-difluoroethyl)pyrimidine (298 mg, 88% yield). $^1$H NMR (CDCl$_3$ 500 MHz): δ 8.92 (s, 21-1), 2.08 (t, 2H).

2-(1,1-Difluoroethyl)-5-vinylpyrimidine

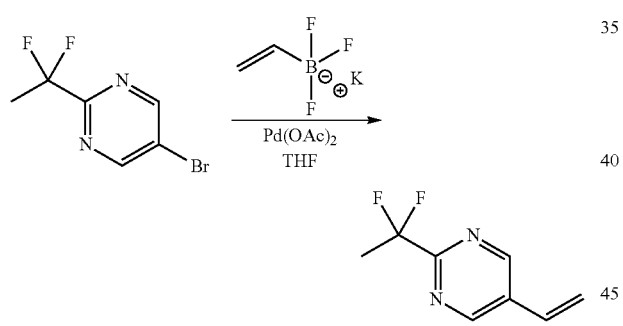

PdOAc$_2$ (22 mg, 0.1 mmol), 2-dicyclohexylphosphino-2'-(N,N-dimethylamino)-biphenyl (53 mg, 0.13 mmol) (DavePhos), cesium carbonate (880 mg, 2.70 mmol) and potassium trifluoro(vinyl)borate (145 mg, 1.1 mmol) were mixed. THF (10 ml), water (3 ml) and 5-bromo-2-(1,1-difluoroethyl)pyrimidine (200 mg, 0.897 mmol) was added. Degassed for 20 minutes, with argon. The resulting mixture was capped and heated to 100° C., for 30 min in microwave oven. The reaction mixture was partitioned between EtOAc (20 mL) and H$_2$O (10 mL). The aq. layer extracted with EtOAc (2×10 mL) and the combined organic layers washed with brine (10 mL), dried (Na$_2$SO$_4$) and concentrated. The reaction was purified by column chromatography on silica gel (petroleum ether: EtOAc=1:0 to 0:1) to afford 2-(1,1-difluoroethyl)-5-vinylpyrimidine (114 mg, 75% yield). $^1$H NMR (CDCl$_3$ 500 MHz): δ 8.88 (s, 2H), 6.73 (m, 1H), 6.02 (d, 1H), 5.61 (d, 1H), 2.10 (t, 2H).

2-(1,1-Difluoroethyl)pyrimidine-5-carbaldehyde

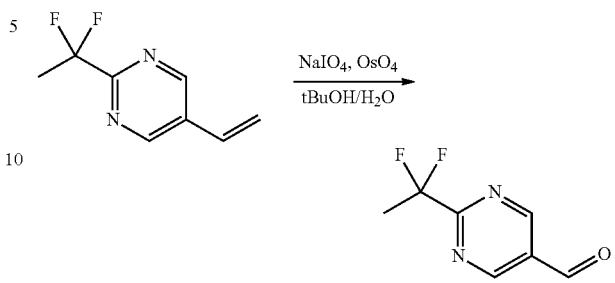

2-(1,1-difluoroethyl)-5-vinylpyrimidine (110 mg, 0.646 mmol) was dissolved in THF (5 ml) and water (2 ml). NaIO$_4$ (571 mg, 2.67 mmol), 2,6-lutidine (143 mg, 0.155 ml, 1.3 mmol) and osmium tetraoxide (138 mg, 0.17 ml, 0.013 mmol, 0.078 molar in tBuOH) was added. The reaction mixture was stirred at room temperature for 2 hours. Water was added and the mixture was extracted with diethyl ether. The organic phase was washed with brine, dried over Na$_2$SO$_4$ and concentrated in vacuo. $^1$H NMR showed a mixture of aldehyde and lutidine, which was used directly in the next reaction, (166 mg, 42% yield, 28% pure). $^1$H NMR (CDCl$_3$ 500 MHz): δ 10.24 (s, 1H), 9.30 (s, 2H), 2.12 (t, 2H).

2-(2-(1,1-Difluoroethyl)pyrimidin-5-yl)-2-(4,4-difluoropiperidin-1-yl)acetonitrile

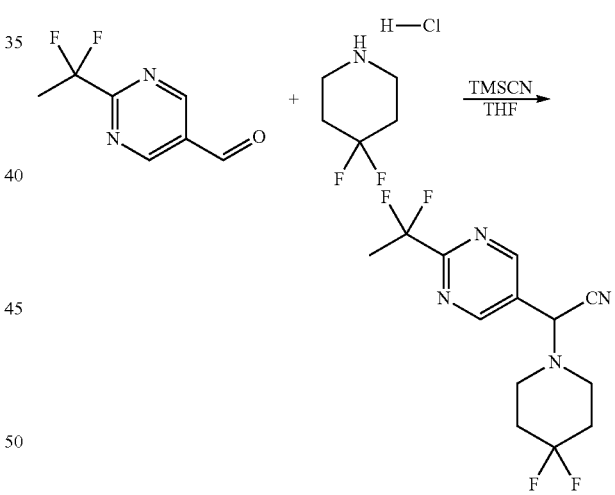

To a solution of 2-(1,1-difluoroethyl)pyrimidine-5-carbaldehyde (166 mg, 0.270 mmol, 28%) in THF (4 ml) was added TMS cyanide (79 mg, 0.1 ml, 0.8 mmol) and zinc iodide (2.2 mg, 6.89 μmol). The mixture was stirred for 15 min. To the mixture was added 4,4-difluoropiperidine hydrochloride (62 mg, 0.393 mmol) and DIPEA (37 mg, 0.05 ml, 0.286 mmol). The resultant mixture was stirred at room temperature overnight. The volatiles were removed by rotary evaporator and the reaction was purified by column chromatography on silica gel (petroleum ether: EtOAc=1:0 to 0:1) to afford 2-(2-(1,1-difluoroethyl)pyrimidin-5-yl)-2-(4,4-difluoropiperidin-1-yl) acetonitrile (as a 1:1 mixture of nitrile and aldehyde) (39 mg, 24% yield). $^1$H NMR (CDCl$_3$ 500 MHz): δ 9.03 (s, 2H), 5.02 (s, 1H), 2.75 (m, 4H), 2.10 (m, 6H).

2-(2-(1,1-Difluoroethyl)pyrimidin-5-yl)-2-(4,4-difluoropiperidin-1-yl)ethanamine

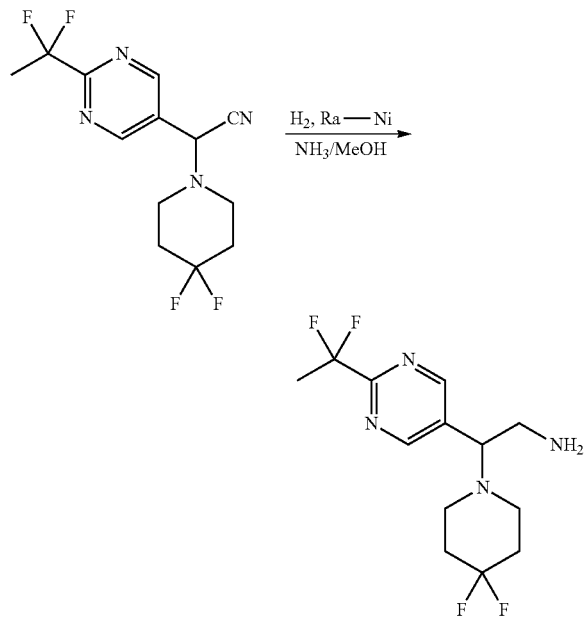

2-(2-(1,1-difluoroethyl)pyrimidin-5-yl)-2-(4,4-difluoropiperidin-1-yl)acetonitrile (39 mg, 0.065 mmol, 50%) was dissolved in ammonia (2034 µl, 4.07 mmol, 2 molar in MeOH) and hydrogenated on H-Cube, by passing the solution over the Ra—Ni catcart 3 times at 60° C. and 60 bar. The solution was concentrated to afford 2-(2-(1,1-difluoroethyl)pyrimidin-5-yl)-2-(4,4-difluoropiperidin-1-yl)ethanamine, which was used crude in the next reaction.

Compounds of formula I can be prepared by employing standard amide bond forming coupling procedures by the reaction of a carboxylic acid of formula II with an amine of formula III.

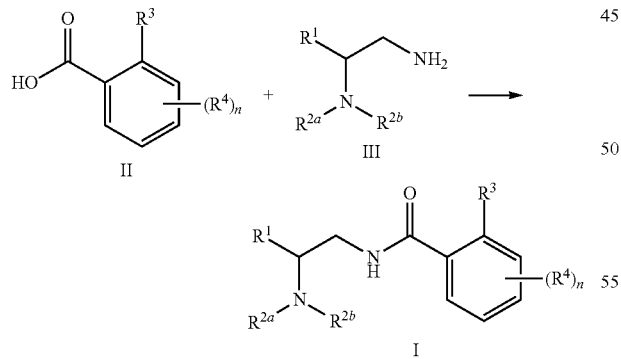

This reaction is typically carried out in a solvent such as THF or DMF, employing peptide coupling reagents exemplified by, but not limited to EDC and HOBt in the presence of a tertiary amine base such as triethylamine or diisopropylethylamine (DIPEA), at a temperature ranging from about 10° C. to about 30° C. Other non-limiting examples of coupling reagents include carbonyldiimidazole, N,N'-dicyclohexylcarbodiimide or benzotriazol-1-yl-oxytripyrrolidinophosphonium hexafluorophosphate as reported by Coste et al. *Tetrahedron Lett.* (1990) 31 (2): 205. Or Compounds of formula I can be prepared by employing standard amide bond forming coupling procedures by the reaction of a carboxylic acid chloride of formula IV with an amine of formula

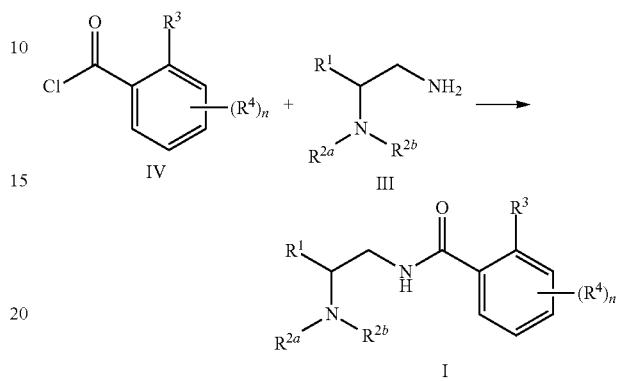

This reaction is typically carried out in a solvent such as THF, DCM or DMF in the presence of a tertiary amine base such as triethylamine or diisopropylethylamine (DIPEA), at a temperature ranging from about 10° C. to about 30° C.

Preparation of the Compounds of the Invention

Example 1a

2-Chloro-5-methyl-N-(2-morpholin-4-yl-2-pyridin-2-yl-ethyl)-benzamide

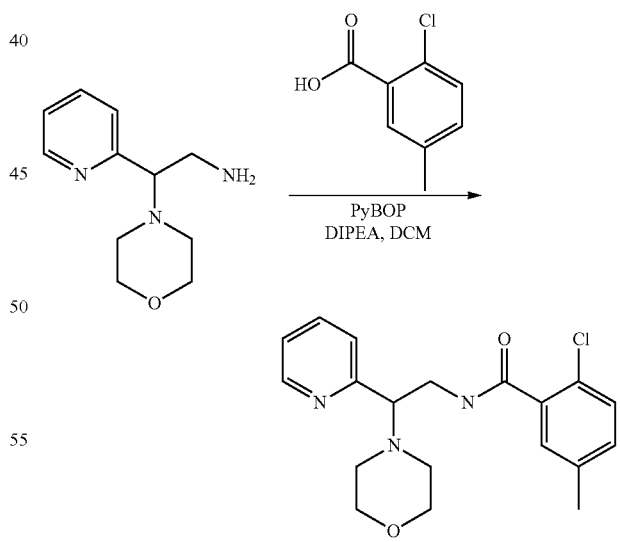

A mixture of (2-morpholin-4-yl-2-pyridin-2-ylethyl)amine (62.2 mg, 0.3 mmol), 2-chloro-5-methylbenzoic acid (54 mg, 0.315 mmol), PyBOP (187 mg, 0.36 mmol) and DIPEA (78 mg, 0.60 mmol) in DCM (1.5 mL) was stirred at room temperature overnight. The mixture was purified by preparative HPLC to yield the title compound (100 mg, yield: 90%). LCMS (Mt): m/z=360.0, $t_R$ (minutes, Method A)=0.89

The following compounds were synthesised in a similar way as to example 1a:

Example 1b

2-Chloro-5-methyl-N-(2-morpholin-4-yl-2-pyridin-3-yl-ethyl)-benzamide

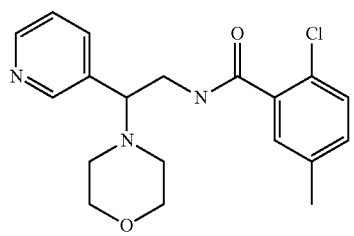 [SMILES: Cc1ccc(Cl)c(C(=O)NCC(c2cccnc2)N2CCOCC2)c1]

From 2-chloro-5-methylbenzoic acid and (2-morpholin-4-yl-2-pyridin-3-ylethyl)amine. LCMS (MH+): m/z=360.0, $t_R$ (minutes, Method A)=0.77

Example 1c

2-Chloro-5-methyl-N-(2-morpholin-4-yl-2-pyridin-4-yl-ethyl)-benzamide

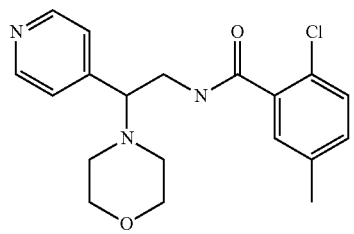 [SMILES: Cc1ccc(Cl)c(C(=O)NCC(c2ccncc2)N2CCOCC2)c1]

From 2-chloro-5-methylbenzoic acid and (2-morpholin-4-yl-2-pyridin-4-ylethyl)amine. LCMS (MH+): m/z=360.0, $t_R$ (minutes, Method A)=0.77

Example 1d

2-Methyl-N-(2-morpholin-4-yl-2-pyridin-2-yl-ethyl)-benzamide

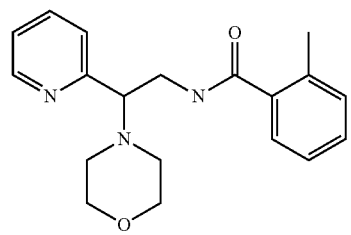 [SMILES: Cc1ccccc1C(=O)NCC(c1ccccn1)N1CCOCC1]

From 2-methylbenzoic acid and (2-morpholin-4-yl-2-pyridin-2-ylethyl)amine.
LCMS (MH+): m/z=326.1, $t_R$ (minutes, Method A)=0.76

Example 1e

2-Methyl-N-(2-morpholin-4-yl-2-pyridin-3-yl-ethyl)-benzamide

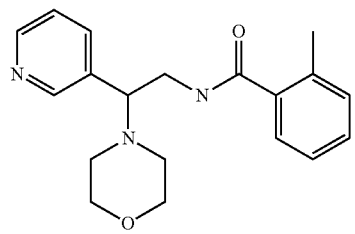 [SMILES: Cc1ccccc1C(=O)NCC(c1cccnc1)N1CCOCC1]

From 2-methylbenzoic acid and (2-morpholin-4-yl-2-pyridin-3-ylethyl)amine.
LCMS (MH+): m/z=326.0, $t_R$ (minutes, Method A)=0.62

Example 1f

2-Methyl-N-(2-morpholin-4-yl-2-pyridin-4-yl-ethyl)-benzamide

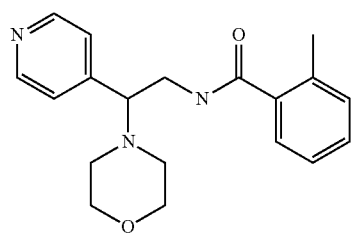 [SMILES: Cc1ccccc1C(=O)NCC(c1ccncc1)N1CCOCC1]

From 2-methylbenzoic acid and (2-morpholin-4-yl-2-pyridin-4-ylethyl)amine.
LCMS (MH+): m/z=326.1, $t_R$ (minutes, Method A)=0.62

Example 1g 2,3-Dichloro-N-(2-morpholin-4-yl-2-pyridin-2-yl-ethyl)-benzamide

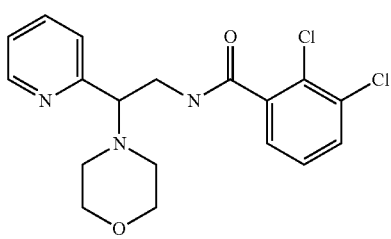 [SMILES: O=C(NCC(c1ccccn1)N1CCOCC1)c1cccc(Cl)c1Cl]

From 2,3-dichlorobenzoic acid and (2-morpholin-4-yl-2-pyridin-2-ylethyl)amine.
LCMS (MH+): m/z=380.1, $t_R$ (minutes, Method A)=0.83

Example 1h 2,3-Dichloro-N-(2-morpholin-4-yl-2-pyridin-3-yl-ethyl)-benzamide

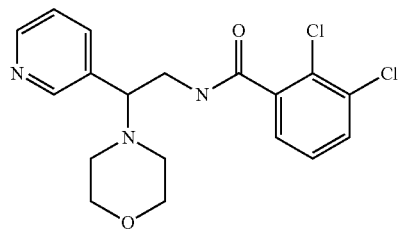 [SMILES: O=C(NCC(c1cccnc1)N1CCOCC1)c1cccc(Cl)c1Cl]

From 2,3-dichlorobenzoic acid and (2-morpholin-4-yl-2-pyridin-3-ylethyl)amine.

LCMS (MH$^+$): m/z=379.9, t$_R$ (minutes, Method A)=0.79

Example 1i 2,3-Dichloro-N-(2-morpholin-4-yl-2-pyridin-4-yl-ethyl)-benzamide

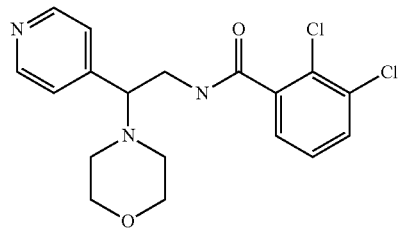 [SMILES: O=C(NCC(c1ccncc1)N1CCOCC1)c1cccc(Cl)c1Cl]

From 2,3-dichlorobenzoic acid and (2-morpholin-4-yl-2-pyridin-4-ylethyl)amine.

LCMS (MH$^+$): m/z=379.9, t$_R$ (minutes, Method A)=0.79

Example 1j 2,3-Dimethyl-N-(2-morpholin-4-yl-2-pyridin-2-yl-ethyl)-benzamide

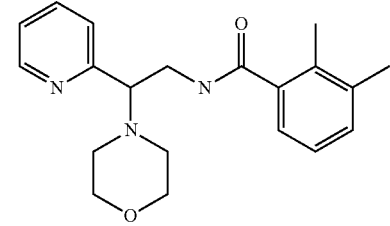 [SMILES: Cc1cccc(C(=O)NCC(c2ccccn2)N2CCOCC2)c1C]

From 2,3-dimethylbenzoic acid and (2-morpholin-4-yl-2-pyridin-2-ylethyl)amine.

LCMS (MH$^+$): m/z=340.1, t$_R$ (minutes, Method A)=0.83

Example 1k 2,3-Dimethyl-N-(2-morpholin-4-yl-2-pyridin-3-yl-ethyl)-benzamide

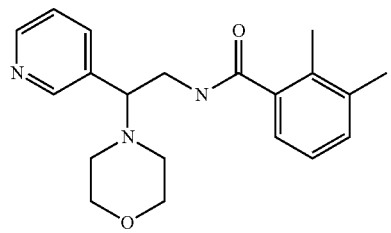 [SMILES: Cc1cccc(C(=O)NCC(c2cccnc2)N2CCOCC2)c1C]

From 2,3-dimethylbenzoic acid and (2-morpholin-4-yl-2-pyridin-3-ylethyl)amine.

LCMS (MH$^+$): m/z=340.1, t$_R$ (minutes, Method A)=0.73

Example 1l 2,3-Dimethyl-N-(2-morpholin-4-yl-2-pyridin-4-yl-ethyl)-benzamide

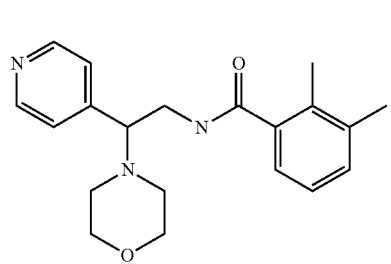 [SMILES: Cc1cccc(C(=O)NCC(c2ccncc2)N2CCOCC2)c1C]

From 2,3-dimethylbenzoic acid and (2-morpholin-4-yl-2-pyridin-4-ylethyl)amine.

LCMS (MH$^+$): m/z=340.0, t$_R$ (minutes, Method A)=0.73

Example 1m 2,3-Dichloro-N-[2-(4-fluoro-phenyl)-2-morpholin-4-yl-ethyl]-benzamide

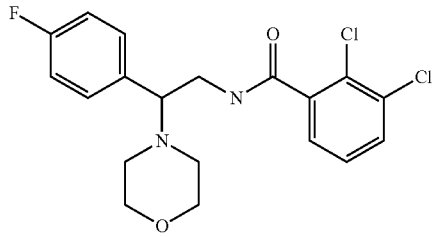 [SMILES: O=C(NCC(c1ccc(F)cc1)N1CCOCC1)c1cccc(Cl)c1Cl]

From 2,3-dichlorobenzoic acid and 2-(4-fluoro-phenyl)-2-morpholin-4-yl-ethylamine.

LCMS (MH$^+$): m/z=396.9, t$_R$ (minutes, Method A)=1.22

Example 1n 2,3-Dichloro-N-[2-(4-methoxy-phenyl)-2-piperidin-1-yl-ethyl]-benzamide

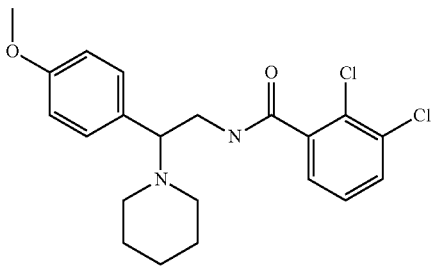 [SMILES: COc1ccc(C(CNC(=O)c2cccc(Cl)c2Cl)N2CCCCC2)cc1]

From 2,3-dichlorobenzoic acid and 2-(4-methoxy-phenyl)-2-piperidin-1-yl-ethylamine.
LCMS (MH$^+$): m/z=407.0, t$_R$ (minutes, Method A)=1.28

Example 1o 2,3-Dichloro-N-[2-(4-methoxy-phenyl)-2-morpholin-4-yl-ethyl]-benzamide

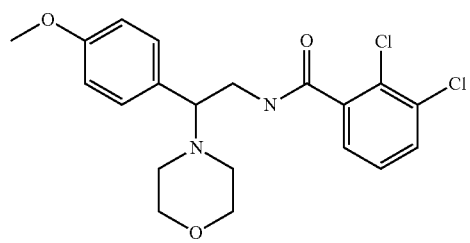 [SMILES: COc1ccc(C(CNC(=O)c2cccc(Cl)c2Cl)N2CCOCC2)cc1]

From 2,3-dichlorobenzoic acid and 2-(4-methoxy-phenyl)-2-morpholin-4-yl-ethylamine.
LCMS (MH$^+$): m/z=408.9, t$_R$ (minutes, Method A)=1.17

Example 1p

N-[2-(4-Fluoro-phenyl)-2-morpholin-4-yl-ethyl]-2,3-dimethyl-benzamide

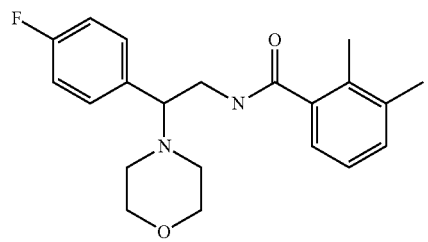 [SMILES: Cc1cccc(C(=O)NCC(c2ccc(F)cc2)N2CCOCC2)c1C]

From 2,3-dimethylbenzoic acid and 2-(4-fluoro-phenyl)-2-morpholin-4-yl-ethylamine.
LCMS (MH$^+$): m/z=357.0, t$_R$ (minutes, Method A)=1.16

Example 1q

N-[2-(4-Methoxy-phenyl)-2-piperidin-1-yl-ethyl]-2,3-dimethyl-benzamide

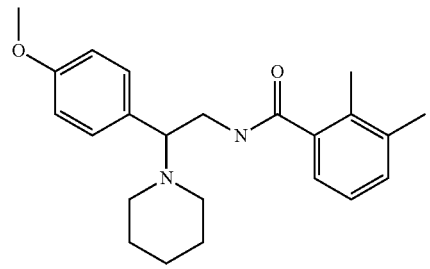 [SMILES: COc1ccc(C(CNC(=O)c2cccc(C)c2C)N2CCCCC2)cc1]

From 2,3-dimethylbenzoic acid and 2-(4-methoxy-phenyl)-2-piperidin-1-yl-ethylamine.
LCMS (MH$^+$): m/z=367.1, t$_R$ (minutes, Method A)=1.09

Example 1r

N-[2-(4-Methoxy-phenyl)-2-morpholin-4-yl-ethyl]-2,3-dimethyl-benzamide

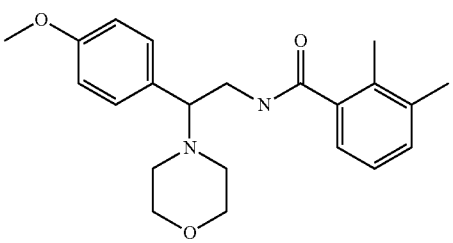

From 2,3-dimethylbenzoic acid and 2-(4-methoxy-phenyl)-2-morpholin-4-yl-ethylamine.
LCMS (MH$^+$): m/z=369.0, t$_R$ (minutes, Method A)=1.10

Example 1s

2-Chloro-N-[2-(4-fluoro-phenyl)-2-morpholin-4-yl-ethyl]-5-methyl-benzamide

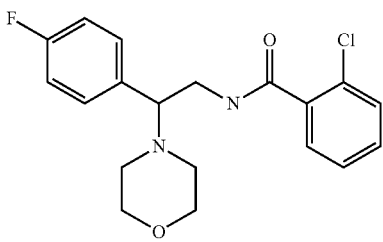

From 2-chlorobenzoic acid and 2-(4-fluoro-phenyl)-2-morpholin-4-yl-ethylamine.
LCMS (MH$^+$): m/z=376.9, t$_R$ (minutes, Method A)=1.21

Example 1t

2-Chloro-N-[2-(4-methoxy-phenyl)-2-piperidin-1-yl-ethyl]-5-methyl-benzamide

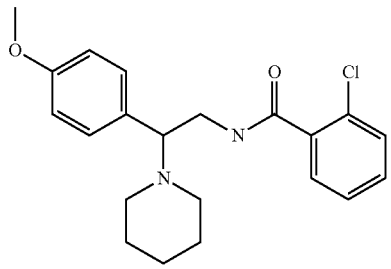 [SMILES: COc1ccc(C(CNC(=O)c2ccccc2Cl)N2CCCCC2)cc1]

From 2-chlorobenzoic acid and 2-(4-methoxy-phenyl)-2-piperidin-1-yl-ethylamine.
LCMS (MH$^+$): m/z=387.0, $t_R$ (minutes, Method A)=1.19

Example 1u

2-Chloro-N-[2-(4-methoxy-phenyl)-2-morpholin-4-yl-ethyl]-5-methyl-benzamide

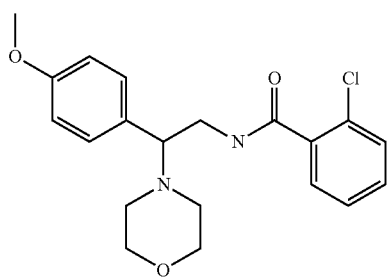 [SMILES: COc1ccc(C(CNC(=O)c2ccccc2Cl)N2CCOCC2)cc1]

From 2-chlorobenzoic acid and 2-(4-methoxy-phenyl)-2-morpholin-4-yl-ethylamine.
LCMS (MH$^+$): m/z=388.9, $t_R$ (minutes, Method A)=1.16

Example 1v

N-[2-(4-Fluoro-phenyl)-2-morpholin-4-yl-ethyl]-2-methyl-benzamide

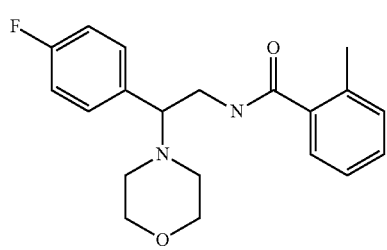 [SMILES: Cc1ccccc1C(=O)NCC(c1ccc(F)cc1)N1CCOCC1]

From 2-methylbenzoic acid and 2-(4-fluoro-phenyl)-2-morpholin-4-yl-ethylamine.
LCMS (MH$^+$): m/z=343.0, $t_R$ (minutes, Method A)=1.07

Example 1w

N-[2-(4-Methoxy-phenyl)-2-piperidin-1-yl-ethyl]-2-methyl-benzamide

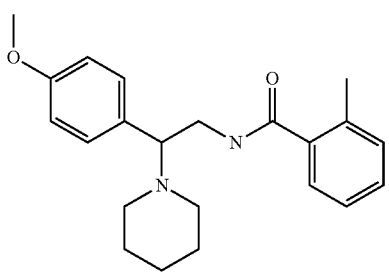 [SMILES: COc1ccc(C(CNC(=O)c2ccccc2C)N2CCCCC2)cc1]

From 2-methylbenzoic acid and 2-(4-methoxy-phenyl)-2-piperidin-1-yl-ethylamine.
LCMS (MH$^+$): m/z=353.0, $t_R$ (minutes, Method A)=0.96

Example 1x

N-[2-(4-Methoxy-phenyl)-2-morpholin-4-yl-ethyl]-2-methyl-benzamide

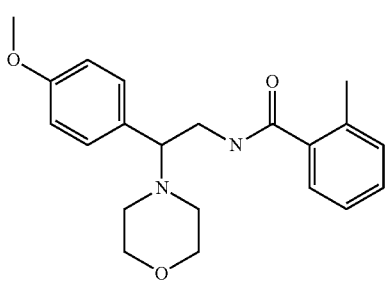 [SMILES: COc1ccc(C(CNC(=O)c2ccccc2C)N2CCOCC2)cc1]

From 2-methylbenzoic acid and 2-(4-methoxy-phenyl)-2-morpholin-4-yl-ethylamine.
LCMS (MH$^+$): m/z=355.0, $t_R$ (minutes, Method A)=1.01

Example 1y

2-Chloro-5-methyl-N-(2-morpholin-4-yl-2-p-tolyl-ethyl)-benzamide

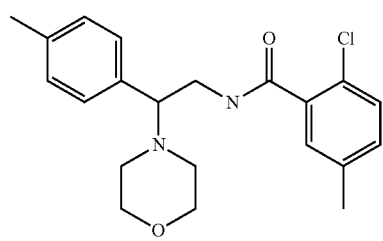 [SMILES: Cc1ccc(C(CNC(=O)c2cc(C)ccc2Cl)N2CCOCC2)cc1]

From 2-chloro-5-methylbenzoic acid and 2-(4-methyl-phenyl)-2-morpholin-4-yl-ethylamine.
LCMS (MH$^+$): m/z=373.0, $t_R$ (minutes, Method A)=1.18

Example 1z

N-[2-(4-Chloro-phenyl)-2-(4,4-difluoro-piperidin-1-yl)-ethyl]-2-methyl-benzamide

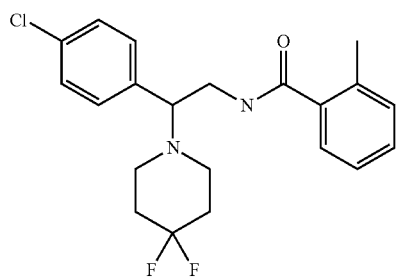 [SMILES: Cc1ccccc1C(=O)NCC(c1ccc(Cl)cc1)N1CCC(F)(F)CC1]

From 2-methylbenzoic acid and 2-(4-chloro-phenyl)-2-(4,4-difluoro-piperidin-1-yl)-ethylamine.
LCMS (MH$^+$): m/z=392.9, $t_R$ (minutes, Method A)=1.62

Example 1a1

N-[2-(4-Chloro-phenyl)-2-(4,4-difluoro-piperidin-1-yl)-ethyl]-2,3-dimethyl-benzamide

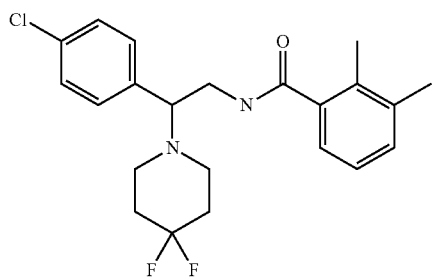 [SMILES: Cc1cccc(C(=O)NCC(c2ccc(Cl)cc2)N2CCC(F)(F)CC2)c1C]

From 2,3-dimethylbenzoic acid and 2-(4-chloro-phenyl)-2-(4,4-difluoro-piperidin-1-yl)-ethylamine.
LCMS (MH$^+$): m/z=407.0, $t_R$ (minutes, Method A)=1.68

Example 1b1

N-[2-(4-Chloro-phenyl)-2-(4,4-difluoro-piperidin-1-yl)-ethyl]-2,3-dichloro-benzamide

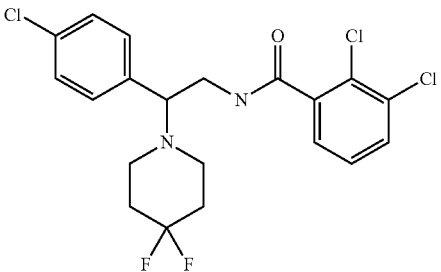 [SMILES: O=C(NCC(c1ccc(Cl)cc1)N1CCC(F)(F)CC1)c1cccc(Cl)c1Cl]

From 2,3-dichlorobenzoic acid and 2-(4-chloro-phenyl)-2-(4,4-difluoro-piperidin-1-yl)-ethylamine.
LCMS (MH$^+$): m/z=446.8, $t_R$ (minutes, Method A)=1.73

Example 2a 2,3-Dichloro-N-[2-(4,4-difluoro-1-piperidyl)-2-(6-fluoro-3-pyridyl)ethyl]benzamide

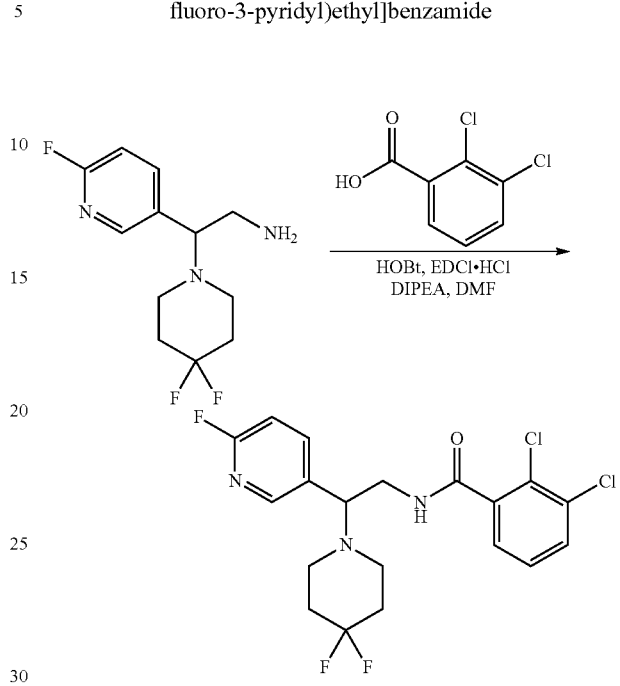

A mixture of 2-(4,4-difluoro-piperidin-1-yl)-2-(6-fluoro-pyridin-3-yl)-ethylamine (100 mg, 0.38 mmol), 2,3-dichlorobenzoic acid (51 mg, 0.28 mmol), HOBT (57 mg, 0.42 mmol), EDC.HCl (81 mg, 0.42 mmol) and DIPEA (108 mg, 0.84 mmol) in DMF (4 mL) was stirred at room temperature overnight. The mixture was purified by preparative HPLC directly to yield the title compound (43 mg, yield: 30%)

LCMS (MH$^+$): m/z=432.0, $t_R$ (minutes, Method E)=2.33

The following compounds were synthesised in a similar way:

Example 2b 2,3-Dichloro-N-[2-(4-chloro-phenyl)-2-morpholin-4-yl-ethyl]-benzamide

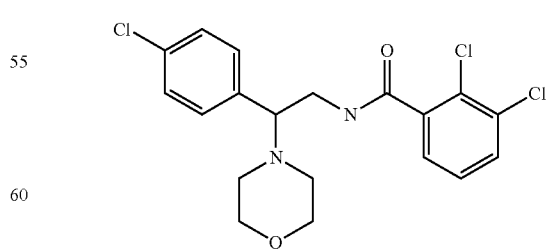

From 2,3-dichlorobenzoic acid and 2-(4-chloro-phenyl)-2-morpholin-4-yl-ethylamine.
LCMS (MH$^+$): m/z=412.8, $t_R$ (minutes, Method D)=0.54

Example 2c 2,3-Dichloro-N-[2-(6-cyclopropyl-pyridin-3-yl)-2-morpholin-4-yl-ethyl]-benzamide

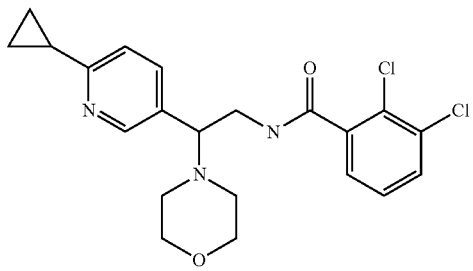 [SMILES: O=C(NCC(c1ccc(C2CC2)nc1)N1CCOCC1)c1cccc(Cl)c1Cl]

From 2,3-dichlorobenzoic acid and 2-(6-cyclopropyl-pyridin-3-yl)-2-morpholin-4-yl-ethylamine.
LCMS (MH$^+$): m/z=412.8, t$_R$ (minutes, Method D)=0.54

Example 2d

N-[2-(4-Chloro-phenyl)-2-morpholin-4-yl-ethyl]-2-methyl-benzamide

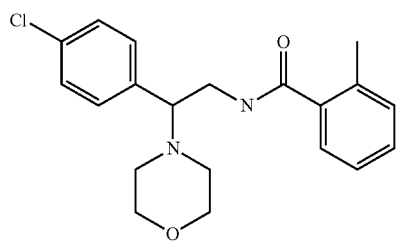 [SMILES: Cc1ccccc1C(=O)NCC(c1ccc(Cl)cc1)N1CCOCC1]

From 2-methylbenzoic acid and 2-(4-chloro-phenyl)-2-morpholin-4-yl-ethylamine.
LCMS (MH$^+$): m/z=359.2, t$_R$ (minutes, Method F)=0.55

Example 2e 2,3-Dichloro-N-[2-morpholino-2-[6-(trifluoromethyl)-3-pyridyl]ethyl]benzamide

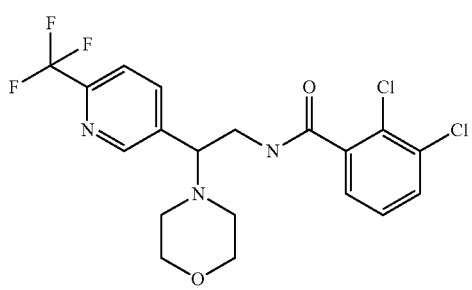 [SMILES: O=C(NCC(c1ccc(C(F)(F)F)nc1)N1CCOCC1)c1cccc(Cl)c1Cl]

From 2,3-dichlorobenzoic acid and 2-morpholin-4-yl-2-(6-trifluoromethyl-pyridin-3-yl)-ethylamine.
LCMS (MH$^+$): m/z=448.1, t$_R$ (minutes, Method B)=0.91

Example 2f

2-Chloro-N-[2-(4-chloro-phenyl)-2-morpholin-4-yl-ethyl]-3-methyl-benzamide

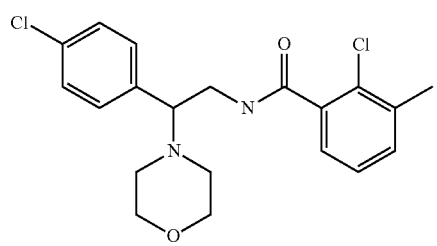 [SMILES: Cc1cccc(C(=O)NCC(c2ccc(Cl)cc2)N2CCOCC2)c1Cl]

From 2-chloro-3-methylbenzoic acid and 2-(4-chloro-phenyl)-2-morpholin-4-yl-ethylamine.
LCMS (MH$^+$): m/z=393.2, t$_R$ (minutes, Method F)=0.58

Example 2g 2,3-Dichloro-N-[2-(6-chloro-3-pyridyl)-2-morpholino-ethyl]benzamide

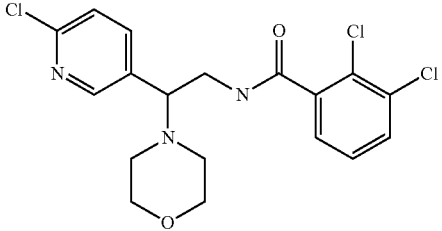

From 2,3-dichlorobenzoic acid and 2-(6-chloro-3-pyridyl)-2-morpholin-4-yl-ethylamine.
LCMS (MH$^+$): m/z=415.8, t$_R$ (minutes, Method C)=1.15

Example 2h 2,3-Dichloro-N-(2-morpholino-2-pyrimidin-5-yl-ethyl)benzamide

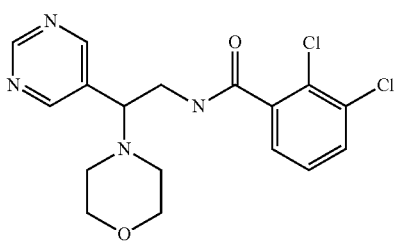 [SMILES: O=C(NCC(c1cncnc1)N1CCOCC1)c1cccc(Cl)c1Cl]

From 2,3-dichlorobenzoic acid and 2-morpholin-4-yl-2-pyrimidin-5-yl-ethylamine.
LCMS (MH$^+$): m/z=381.1, t$_R$ (minutes, Method C)=0.92

Example 2i 2,3-Dichloro-N-[2-(2-methylpyrimidin-5-yl)-2-morpholino-ethyl]benzamide

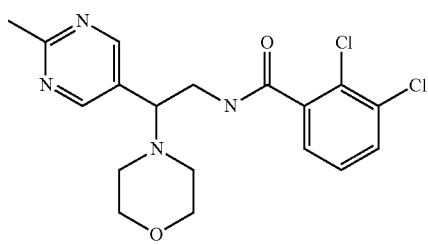 [SMILES: Cc1ncc(C(CNC(=O)c2cccc(Cl)c2Cl)N2CCOCC2)cn1]

From 2,3-dichlorobenzoic acid and 2-(2-methyl-pyrimidin-5-yl)-2-morpholin-4-yl-ethylamine.
LCMS (MH$^+$): m/z=395.0, t$_R$ (minutes, Method C)=0.94

Example 2j 2,3-Dichloro-N-[2-morpholino-2-[2-(trifluoromethyl)pyrimidin-5-yl]ethyl]benzamide

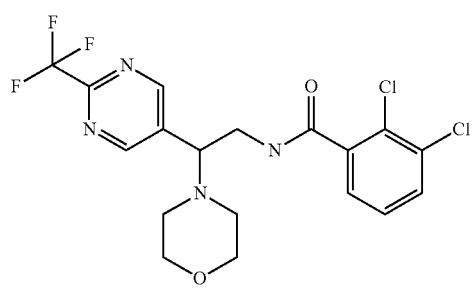 [SMILES: O=C(NCC(c1cnc(C(F)(F)F)nc1)N1CCOCC1)c1cccc(Cl)c1Cl]

From 2,3-dichlorobenzoic acid and 2-(2-(trifluoromethyl)pyrimidin-5-yl)-2-morpholin-4-yl-ethylamine.
LCMS (MH$^+$): m/z=449.0, t$_R$ (minutes, Method B)=0.95

Example 2k 2,3-Dichloro-N-[2-(4,4-difluoro-piperidin-1-yl)-2-(4-fluoro-phenyl)-ethyl]-benzamide

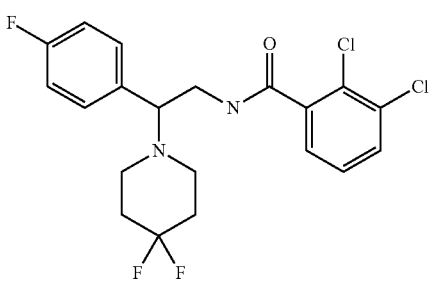

From 2,3-dichlorobenzoic acid and 2-(4-fluoro-phenyl)-2-(4,4-difluoro-piperidin-1-yl)-ethylamine.
LCMS (MH$^+$): m/z=431.2, t$_R$ (minutes, Method D)=0.57

Example 2l 2,3-dichloro-N-[2-(4,4-difluoro-1-piperidyl)-2-(4-methoxyphenyl)ethyl]benzamide

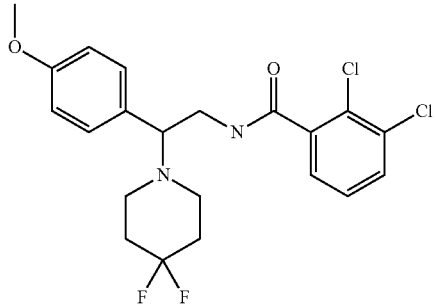

From 2,3-dichlorobenzoic acid and 2-(4-methoxy-phenyl)-2-(4,4-difluoro-piperidin-1-yl)-ethylamine.
LCMS (MH$^+$): m/z=443.1, t$_R$ (minutes, Method E)=1.81

Example 2m

3-Dichloro-N-[2-(4,4-difluoro-1-piperidyl)-2-(6-fluoro-3-pyridyl)ethyl]benzamide

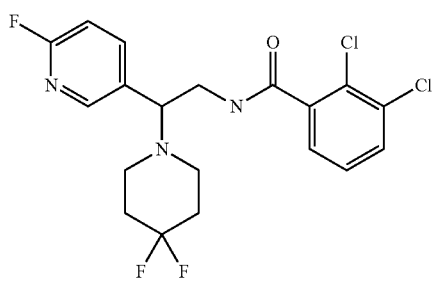 [SMILES: O=C(NCC(c1ccc(F)cc1)N1CCC(F)(F)CC1)c1cccc(Cl)c1Cl]

From 2,3-dichlorobenzoic acid and 2-(6-fluoro-3-pyridyl)-2-(4,4-difluoro-piperidin-1-yl)-ethylamine.
LCMS (MH$^+$): m/z=432.0, t$_R$ (minutes, Method E)=2.33

Example 2n 2-chloro-N-[2-(4,4-difluoro-1-piperidyl)-2-(6-fluoro-3-pyridyl)ethyl]benzamide

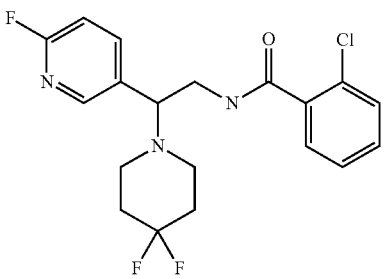 [SMILES: O=C(NCC(c1ccc(F)nc1)N1CCC(F)(F)CC1)c1ccccc1Cl]

From 2-chlorobenzoic acid and 2-(6-fluoro-3-pyridyl)-2-(4,4-difluoro-piperidin-1-yl)-ethylamine.
LCMS (MH$^+$): m/z=398.1, t$_R$ (minutes, Method E)=2.10

Example 2o 2,3-Dichloro-N-[2-(4,4-difluoro-1-piperidyl)-2-[6-(trifluoromethyl)-3-pyridyl]ethyl]benzamide

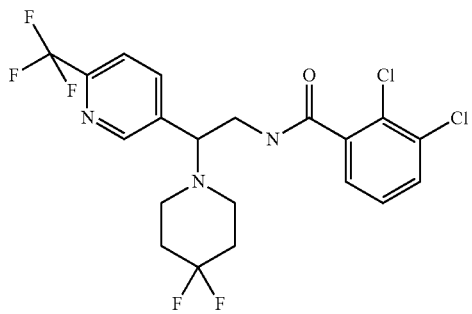 [SMILES: O=C(NCC(c1ccc(C(F)(F)F)nc1)N1CCC(F)(F)CC1)c1cccc(Cl)c1Cl]

From 2,3-dichlorobenzoic acid and 2-(6-(trifluoromethyl)-3-pyridyl)-2-(4,4-difluoro-piperidin-1-yl)-ethylamine.
LCMS (MH$^+$): m/z=482.0, t$_R$ (minutes, Method E)=2.62

Example 2p

2-Chloro-N-[2-(4,4-difluoro-1-piperidyl)-2-[6-(trifluoromethyl)-3-pyridyl]ethyl]benzamide

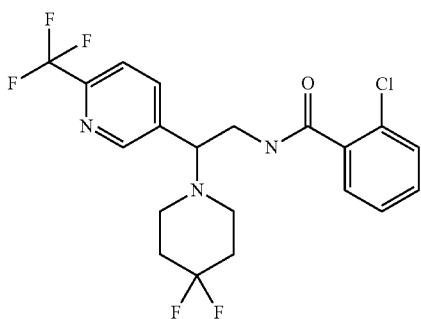 [SMILES: O=C(NCC(c1ccc(C(F)(F)F)nc1)N1CCC(F)(F)CC1)c1ccccc1Cl]

From 2-chlorobenzoic acid and 2-(6-(trifluoromethyl)-3-pyridyl)-2-(4,4-difluoro-piperidin-1-yl)-ethylamine.
LCMS (MH$^+$): m/z=448.1, t$_R$ (minutes, Method E)=2.30

Example 2q 2,3-dichloro-N-(2-(4-chlorophenyl)-2-(1,4-oxazepan-4-yl)ethyl)benzamide

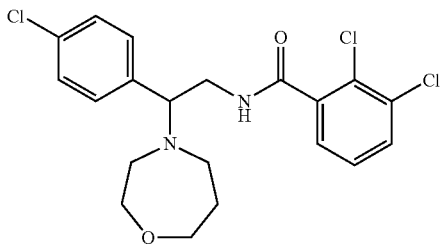 [SMILES: O=C(NCC(c1ccc(Cl)cc1)N1CCCOCC1)c1cccc(Cl)c1Cl]

From 2,3-dichlorobenzoic acid and 2-(4-chlorophenyl)-2-(1,4-oxazepan-4-yl)ethanamine.
LCMS (MH+): m/z=429.0, t$_R$ (minutes, Method H)=0.51

Example 2r 2,3-dichloro-N-(2-(4-chlorophenyl)-2-(pyrrolidin-1-yl)ethyl)benzamide

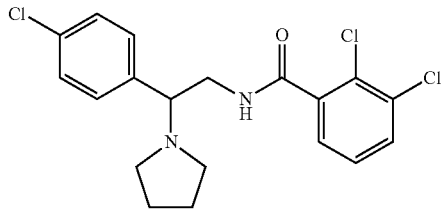 [SMILES: O=C(NCC(c1ccc(Cl)cc1)N1CCCC1)c1cccc(Cl)c1Cl]

From 2,3-dichlorobenzoic acid and 2-(4-chlorophenyl)-2-(pyrrolidin-1-yl)ethanamine.
LCMS (MH+): m/z=397.2, t$_R$ (minutes, Method D)=0.54

Example 2s 2-chloro-3-fluoro-N-(2-(2-methylpyrimidin-5-yl)-2-morpholinoethyl)benzamide

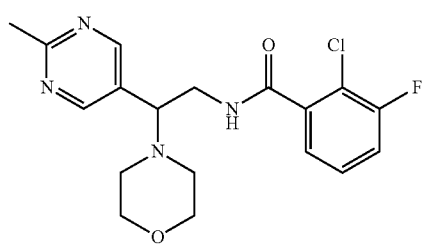 [SMILES: Cc1ncc(C(CNC(=O)c2cccc(F)c2Cl)N2CCOCC2)cn1]

From 2-chloro-3-fluorobenzoic acid and 2-(2-methylpyrimidin-5-yl)-2-morpholinoethanamine.
LCMS (MH+): m/z=379.2, t$_R$ (minutes, Method D)=0.36

Example 2t 2,6-difluoro-N-(2-(2-methylpyrimidin-5-yl)-2-morpholinoethyl)benzamide

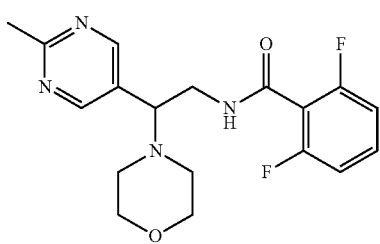 [SMILES: Cc1ncc(C(CNC(=O)c2c(F)cccc2F)N2CCOCC2)cn1]

From 2,6-difluorobenzoic acid and 2-(2-methylpyrimidin-5-yl)-2-morpholinoethanamine.
LCMS (MH+): m/z=363.2, t$_R$ (minutes, Method D)=0.40

Example 2u 2,6-dichloro-N-(2-(2-methylpyrimidin-5-yl)-2-morpholinoethyl)benzamide

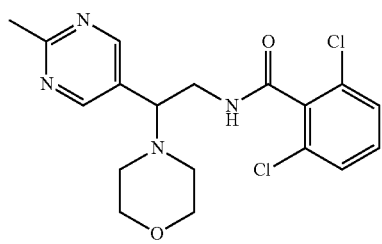 [SMILES: Cc1ncc(C(CNC(=O)c2c(Cl)cccc2Cl)N2CCOCC2)cn1]

From 2,6-dichlorobenzoic acid and 2-(2-methylpyrimidin-5-yl)-2-morpholinoethanamine.
LCMS (MH+): m/z=395.2, $t_R$ (minutes, Method D)=0.45

Example 2v 2-chloro-6-fluoro-N-(2-(2-methylpyrimidin-5-yl)-2-morpholinoethyl)benzamide

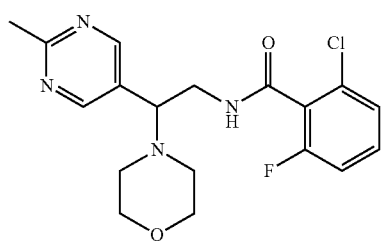 [SMILES: Cc1ncc(C(CNC(=O)c2c(F)cccc2Cl)N2CCOCC2)cn1]

From 2-chloro-6-fluorobenzoic acid and 2-(2-methylpyrimidin-5-yl)-2-morpholinoethanamine.
LCMS (MH+): m/z=379.2, $t_R$ (minutes, Method D)=0.43

Example 2x 2,3-dichloro-N-(2-(4,4-difluoropiperidin-1-yl)-2-(2-(trifluoromethyl)pyrimidin-5-yl)ethyl)benzamide

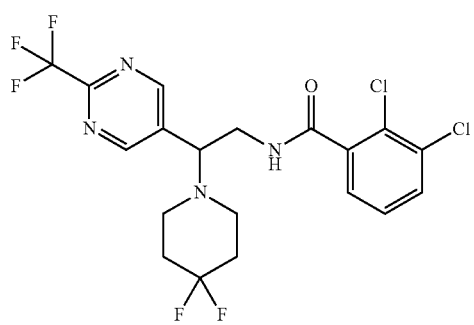 [SMILES: O=C(NCC(c1cnc(C(F)(F)F)nc1)N1CCC(F)(F)CC1)c1cccc(Cl)c1Cl]

From 2,3-dichlorobenzoic acid and 2-(4,4-difluoropiperidin-1-yl)-2-(2-(trifluoromethyl)pyrimidin-5-yl)ethanamine.
LCMS (MH+): m/z=483.1, $t_R$ (minutes, Method F)=2.56

Example 2y 2-chloro-N-(2-(4,4-difluoropiperidin-1-yl)-2-(2-(trifluoromethyl)pyrimidin-5-yl)ethyl)benzamide

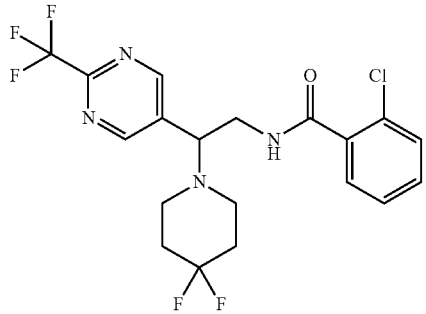 [SMILES: O=C(NCC(c1cnc(C(F)(F)F)nc1)N1CCC(F)(F)CC1)c1ccccc1Cl]

From 2-chlorobenzoic acid and 2-(4,4-difluoropiperidin-1-yl)-2-(2-(trifluoromethyl)pyrimidin-5-yl)ethanamine.
LCMS (MH+): m/z=449.1, $t_R$ (minutes, Method F)=2.38

Example 2z 2,3-dichloro-N-(2-(4,4-difluoropiperidin-1-yl)-2-(2-methylpyrimidin-5-yl)ethyl)benzamide

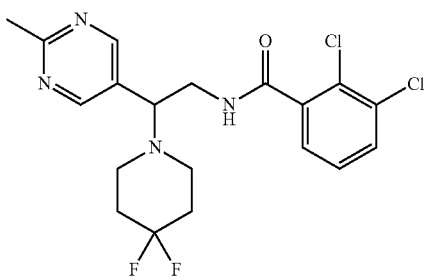 [SMILES: Cc1ncc(C(CNC(=O)c2cccc(Cl)c2Cl)N2CCC(F)(F)CC2)cn1]

From 2,3-dichlorobenzoic acid and 2-(4,4-difluoropiperidin-1-yl)-2-(2-methylpyrimidin-5-yl)ethanamine.
LCMS (MH+): m/z=429.1, $t_R$ (minutes, Method F)=1.83

Example 2a1

2,3-dichloro-N-(2-(4,4-dimethylpiperidin-1-yl)-2-(2-(trifluoromethyl)pyrimidin-5-yl)ethyl)benzamide

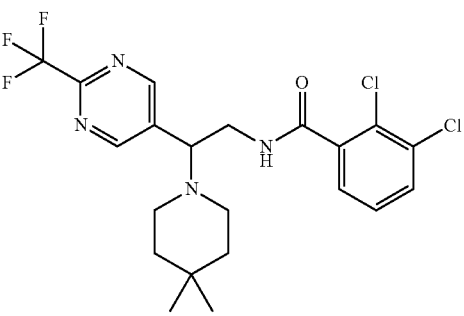 [SMILES: CC1(C)CCN(C(CNC(=O)c2cccc(Cl)c2Cl)c2cnc(C(F)(F)F)nc2)CC1]

From 2,3-dichlorobenzoic acid and 2-(4,4-dimethylpiperidin-1-yl)-2-(2-(trifluoromethyl)pyrimidin-5-yl)ethanamine.
LCMS (MH+): m/z=475.1, $t_R$ (minutes, Method G)=2.23

Example 2b1

2,3-dichloro-N-(2-(4-methoxypiperidin-1-yl)-2-(2-methylpyrimidin-5-yl)ethyl)benzamide

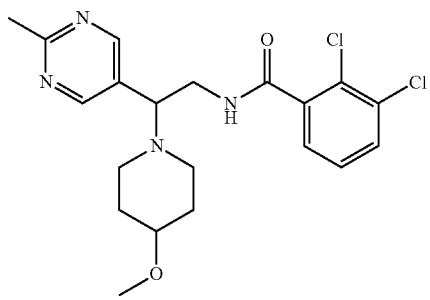 [SMILES: COC1CCN(C(CNC(=O)c2cccc(Cl)c2Cl)c2cnc(C)nc2)CC1]

From 2,3-dichlorobenzoic acid and 2-(4-methoxypiperidin-1-yl)-2-(2-methylpyrimidin-5-yl)ethanamine.
LCMS (MH+): m/z=423.1, $t_R$ (minutes, Method F)=2.04

Example 2c1

2,3-dichloro-N-(2-(2-methylpyrimidin-5-yl)-2-(1,4-oxazepan-4-yl)ethyl)benzamide

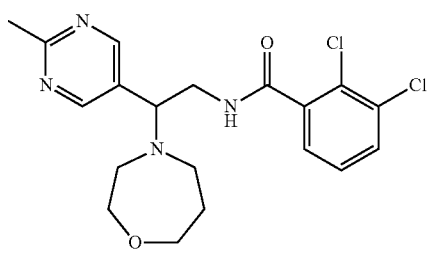 [SMILES: Cc1ncc(C(CNC(=O)c2cccc(Cl)c2Cl)N2CCCOCC2)cn1]

From 2,3-dichlorobenzoic acid and 2-(2-methylpyrimidin-5-yl)-2-(1,4-oxazepan-4-yl)ethanamine.
LCMS (MH+): m/z=409.1, $t_R$ (minutes, Method D)=0.40

Example 2d1

2-chloro-N-(2-(2-methylpyrimidin-5-yl)-2-(1,4-oxazepan-4-yl)ethyl)benzamide

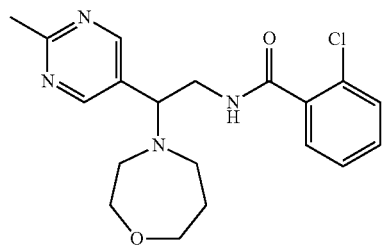 [SMILES: Cc1ncc(C(CNC(=O)c2ccccc2Cl)N2CCCOCC2)cn1]

From 2-chlorobenzoic acid and 2-(2-methylpyrimidin-5-yl)-2-(1,4-oxazepan-4-yl)ethanamine.
LCMS (MH+): m/z=375.1, $t_R$ (minutes, Method D)=0.33

Example 2e1

2-chloro-3-fluoro-N-(2-(2-methylpyrimidin-5-yl)-2-(1,4-oxazepan-4-yl)ethyl)benzamide

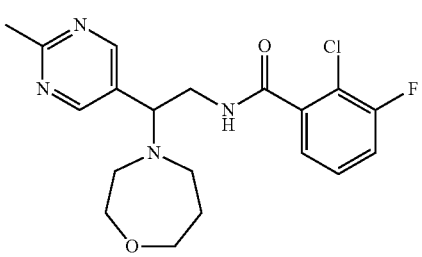 [SMILES: Cc1ncc(C(CNC(=O)c2cccc(F)c2Cl)N2CCCOCC2)cn1]

From 2-chloro-3-fluorobenzoic acid and 2-(2-methylpyrimidin-5-yl)-2-(1,4-oxazepan-4-yl)ethanamine.
LCMS (MH+): m/z=393.1, $t_R$ (minutes, Method D)=0.35

Example 2f1

2,6-dichloro-N-(2-(2-methylpyrimidin-5-yl)-2-(1,4-oxazepan-4-yl)ethyl)benzamide

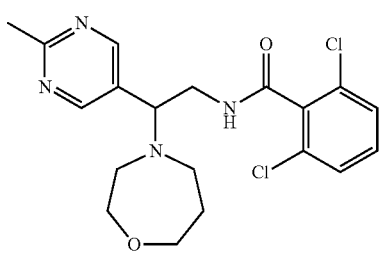 [SMILES: Cc1ncc(C(CNC(=O)c2c(Cl)cccc2Cl)N2CCCOCC2)cn1]

From 2,6-dichlorobenzoic acid and 2-(2-methylpyrimidin-5-yl)-2-(1,4-oxazepan-4-yl)ethanamine.
LCMS (MH+): m/z=409.1, $t_R$ (minutes, Method D)=0.35

Example 2g1

2-chloro-6-fluoro-N-(2-(2-methylpyrimidin-5-yl)-2-(1,4-oxazepan-4-yl)ethyl)benz amide

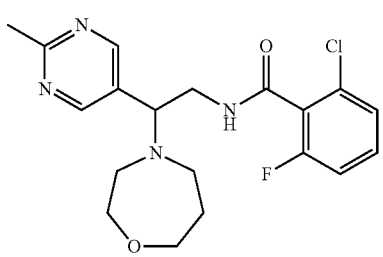 [SMILES: Cc1ncc(C(CNC(=O)c2c(F)cccc2Cl)N2CCCOCC2)cn1]

From 2-chloro-6-fluorobenzoic acid and 2-(2-methylpyrimidin-5-yl)-2-(1,4-oxazepan-4-yl)ethanamine.
LCMS (MH+): m/z=393.1, $t_R$ (minutes, Method D)=0.32

Example 2h1

2,3-dichloro-N-(2-(2-methylpyrimidin-5-yl)-2-(3-methylpyrrolidin-1-yl)ethyl)benzamide

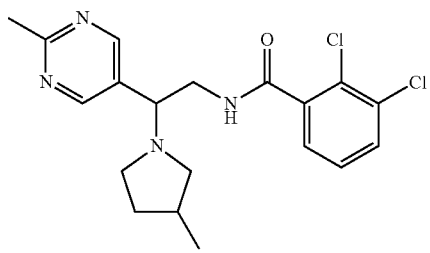 [SMILES: Cc1ncc(C(CNC(=O)c2cccc(Cl)c2Cl)N2CCC(C)C2)cn1]

From 2,3-dichlorobenzoic acid and 2-(2-methylpyrimidin-5-yl)-2-(3-methylpyrrolidin-1-yl)ethanamine.
LCMS (MH+): m/z=393.1, $t_R$ (minutes, Method D)=0.44

Example 2i1

2,3-dichloro-N-(2-(2-methylpyrimidin-5-yl)-2-(3,3,4,4-tetrafluoropyrrolidin-1-yl)ethyl)benzamide

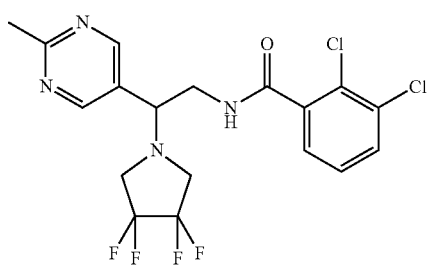 [SMILES: Cc1ncc(C(CNC(=O)c2cccc(Cl)c2Cl)N2CC(F)(F)C(F)(F)C2)cn1]

From 2,3-dichlorobenzoic acid and 2-(2-methylpyrimidin-5-yl)-2-(3,3,4,4-tetrafluoropyrrolidin-1-yl)ethanamine.
LCMS (MH+): m/z=451.1, $t_R$ (minutes, Method D)=0.64

Example 2j1

2,4-dichloro-N-(2-morpholino-2-(2-(trifluoromethyl)pyrimidin-5-yl)ethyl)benzamide

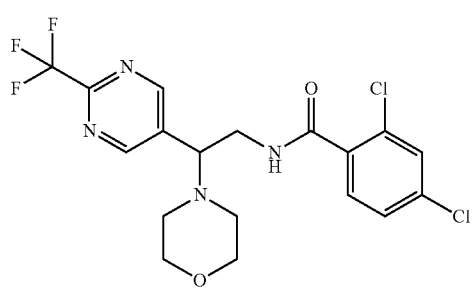 [SMILES: O=C(NCC(c1cnc(C(F)(F)F)nc1)N1CCOCC1)c1ccc(Cl)cc1Cl]

From 2,4-dichlorobenzoic acid and 2-morpholino-2-(2-(trifluoromethyl)pyrimidin-5-yl)ethanamine.
LCMS (MH+): m/z=449.1, $t_R$ (minutes, Method D)=0.63

Example 2k1

2,4-dichloro-N-(2-(4,4-difluoropiperidin-1-yl)-2-(2-methylpyrimidin-5-yl)ethyl)benzamide

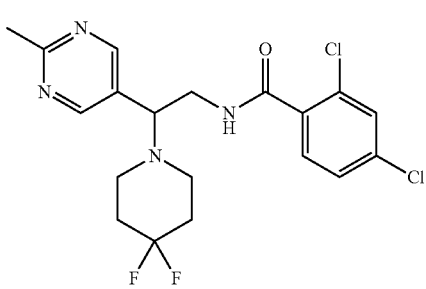 [SMILES: Cc1ncc(C(CNC(=O)c2ccc(Cl)cc2Cl)N2CCC(F)(F)CC2)cn1]

From 2,4-dichlorobenzoic acid and 2-(4,4-difluoropiperidin-1-yl)-2-(2-methylpyrimidin-5-yl)ethanamine.
LCMS (MH+): m/z=429.2, $t_R$ (minutes, Method D)=0.61

Example 2l1

2,3-dichloro-N-(2-(3-methylpiperidin-1-yl)-2-(2-methylpyrimidin-5-yl)ethyl)benzamide

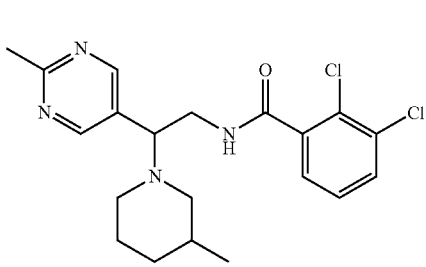 [SMILES: Cc1ncc(C(CNC(=O)c2cccc(Cl)c2Cl)N2CCCC(C)C2)cn1]

From 2,3-dichlorobenzoic acid and 2-(3-methylpiperidin-1-yl)-2-(2-methylpyrimidin-5-yl)ethanamine.
LCMS (MH+): m/z=407.2, $t_R$ (minutes, Method D)=0.49

Example 2m1

2,3-dichloro-N-(2-(2-isopropylpiperidin-1-yl)-2-(2-methylpyrimidin-5-yl)ethyl)benzamide

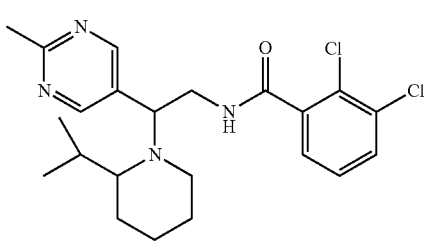 [SMILES: Cc1ncc(C(CNC(=O)c2cccc(Cl)c2Cl)N2CCCCC2C(C)C)cn1]

From 2,3-dichlorobenzoic acid and 2-(2-isopropylpiperidin-1-yl)-2-(2-methylpyrimidin-5-yl)ethanamine.
LCMS (MH+): m/z=435.2, $t_R$ (minutes, Method D)=0.51

Example 2n1

2,3-dichloro-N-(2-(2-methylpiperidin-1-yl)-2-(2-methylpyrimidin-5-yl)ethyl)benzamide

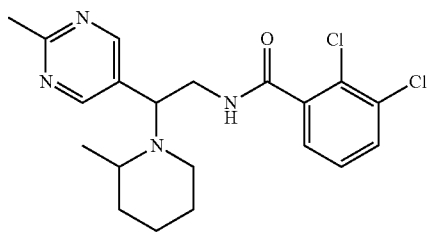 [SMILES: Cc1ncc(C(CNC(=O)c2cccc(Cl)c2Cl)N2CCCCC2C)cn1]

From 2,3-dichlorobenzoic acid and 2-(2-methylpiperidin-1-yl)-2-(2-methylpyrimidin-5-yl)ethanamine.
LCMS (MH+): m/z=407.1, $t_R$ (minutes, Method E)=0.49

Example 2o1

N-(2-(2-azabicyclo[2.2.1]heptan-2-yl)-2-(2-methylpyrimidin-5-yl)ethyl)-2,3-dichlorobenzamide

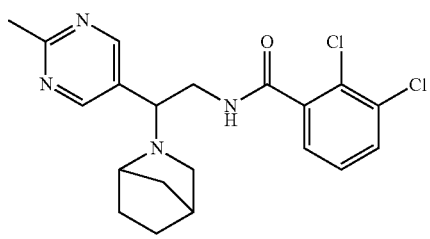 [SMILES: Cc1ncc(C(CNC(=O)c2cccc(Cl)c2Cl)N2CC3CCC2C3)cn1]

From 2,3-dichlorobenzoic acid and 2-(2-azabicyclo[2.2.1]heptan-2-yl)-2-(2-methylpyrimidin-5-yl)ethanamine.
LCMS (MH+): m/z=405.2, $t_R$ (minutes, Method D)=0.46

Example 2p1

2,3-dichloro-N-(2-(4,4-difluoropiperidin-1-yl)-2-(2-(dimethylamino)pyrimidin-5-yl)ethyl)benzamide

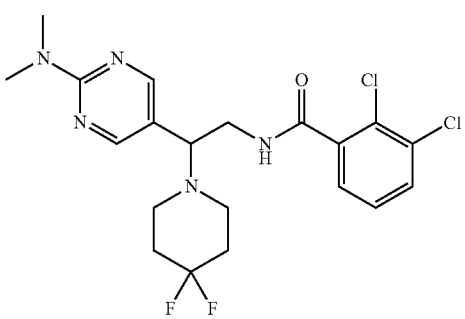 [SMILES: CN(C)c1ncc(C(CNC(=O)c2cccc(Cl)c2Cl)N2CCC(F)(F)CC2)cn1]

From 2,3-dichlorobenzoic acid and 5-(2-amino-1-(4,4-difluoropiperidin-1-yl)ethyl)-N,N-dimethylpyrimidin-2-amine.
LCMS (MH+): m/z=458.2, $t_R$ (minutes, Method D)=0.57

Example 2q1

2-chloro-3-fluoro-N-(2-morpholino-2-(2-(trifluoromethyl)pyrimidin-5-yl)ethyl)benzamide

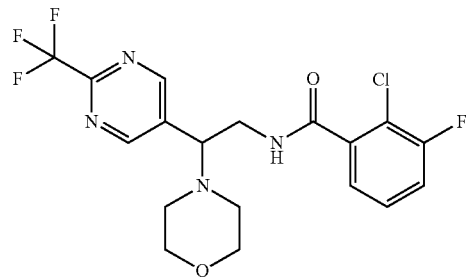 [SMILES: O=C(NCC(c1cnc(C(F)(F)F)nc1)N1CCOCC1)c1cccc(F)c1Cl]

From 2-chloro-3-fluorobenzoic acid and 2-morpholino-2-(2-(trifluoromethyl)pyrimidin-5-yl)ethanamine.
LCMS (MH+): m/z=433.3, $t_R$ (minutes, Method D)=0.57

Example 2r1

2,3-dichloro-N-(2-(4,4-difluoropiperidin-1-yl)-2-(1-methyl-6-oxo-1,6-dihydropyridin-3-yl)ethyl)benzamide

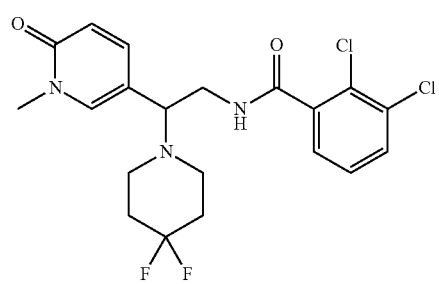 [SMILES: Cn1cc(C(CNC(=O)c2cccc(Cl)c2Cl)N2CCC(F)(F)CC2)ccc1=O]

From 2,3-dichlorobenzoic acid and 5-(2-amino-1-(4,4-difluoropiperidin-1-yl)ethyl)-1-methylpyridin-2(1H)-one.
LCMS (MH+): m/z=323.0, $t_R$ (minutes, Method E)=0.43

Example 2s1

2,3-dichloro-N-(2-(4-chloropiperidin-1-yl)-2-(2-methylpyrimidin-5-yl)ethyl)benzamide

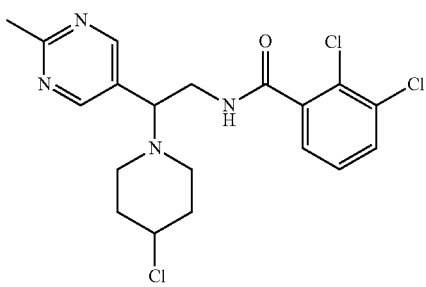

From 2,3-dichlorobenzoic acid and 2-(4-chloropiperidin-1-yl)-2-(2-methylpyrimidin-5-yl)ethanamine.
LCMS (MH+): m/z=427.0, $t_R$ (minutes, Method F)=1.95

Example 2t1

2,4-dichloro-N-(2-(4-chloropiperidin-1-yl)-2-(2-methylpyrimidin-5-yl)ethyl)benzamide

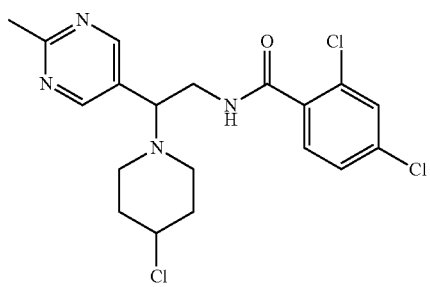 [SMILES: Cc1ncc(C(CNC(=O)c2ccc(Cl)cc2Cl)N2CCC(Cl)CC2)cn1]

From 2,4-dichlorobenzoic acid and 2-(4-chloropiperidin-1-yl)-2-(2-methylpyrimidin-5-yl)ethanamine.
LCMS (MH+): m/z=427.0, $t_R$ (minutes, Method F)=1.99

Example 3a (−)2,3-Dichloro-N-[2-morpholino-2-[6-(trifluoromethyl)-3-pyridyl]ethyl]benzamide

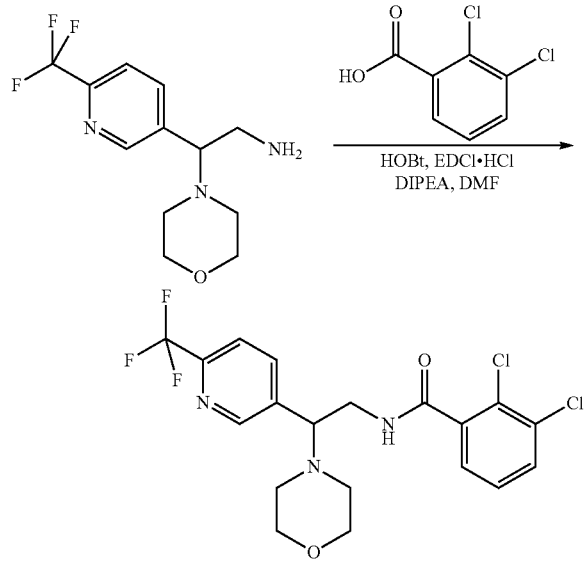

A mixture of 2-Morpholin-4-yl-2-(6-trifluoromethyl-pyridin-3-yl)-ethylamine (200 mg, 0.72 mmol), 2,3-dichlorobenzoic acid (138 mg, 0.726 mmol), HOBT (147 mg, 1.09 mmol), EDCl.HCl (207 mg, 1.09 mmol) and DIPEA (281 mg, 2.18 mmol) in DMF (2 mL) was stirred at room temperature overnight. The mixture was purified by preparative HPLC directly to yield the racemic compound (150 mg, yield: 46.3%).

The racemic mixture was separated into the two enantiomers by preparative SFC to yield the title compound LCMS (MH$^+$): m/z=448.0, $t_R$ (minutes, Method E)=2.31. $[\alpha]_D^{20}$=−5.7 (c=2.28 mg/mL, CHCl$_3$)
And the corresponding enantiomer

Example 3b (+)2,3-Dichloro-N-[2-morpholino-2-[6-(trifluoromethyl)-3-pyridyl]ethyl]benzamide LCMS (MH$^+$): m/z=448.0, $t_R$ (minutes, Method E)=2.31. $[\alpha]_D^{20}$=5.4 (c=5.2 mg/mL, CHCl$_3$)
The following compounds were synthesised in a similar way:

Example 3c (−)2-Chloro-N-[2-morpholino-2-[6-(trifluoromethyl)-3-pyridyl]ethyl]-3-(trifluoromethyl)benzamide

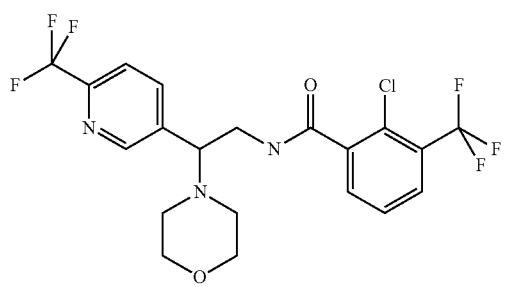 [SMILES: O=C(NCC(c1ccc(C(F)(F)F)nc1)N1CCOCC1)c1cccc(C(F)(F)F)c1Cl]

From 2-chloro-3-(trifluoromethyl)benzoic acid and 2-morpholin-4-yl-2-(6-trifluoromethyl-pyridin-3-yl)-ethylamine.
LCMS (MH$^+$): m/z=482.1, $t_R$ (minutes, Method E)=2.43. $[\alpha]_D^{20}$=−6.67 (c=1.2 mg/mL, CHCl$_3$)

Example 3d (+)2-Chloro-N-[2-morpholino-2-[6-(trifluoromethyl)-3-pyridyl]ethyl]-3-(trifluoromethyl)benzamide LCMS (MH$^+$): m/z=482.1, $t_R$ (minutes, Method E)=2.42. $[\alpha]_D^{20}$=5.83 (c=1.2 mg/mL, CHCl$_3$)

Example 3e (−)2,3-Dichloro-N-[2-morpholino-2-[2-(trifluoromethyl)pyrimidin-5-yl]ethyl]benzamide

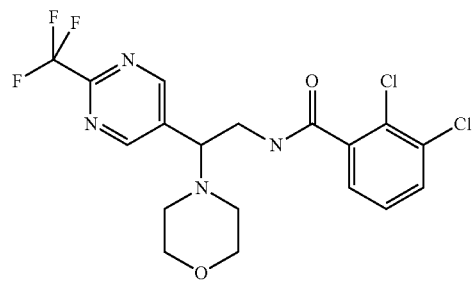 [SMILES: O=C(NCC(c1cnc(C(F)(F)F)nc1)N1CCOCC1)c1cccc(Cl)c1Cl]

From 2,3-dichlorobenzoic acid and 2-(2-(trifluoromethyl)pyrimidin-5-yl)-2-morpholin-4-yl-ethylamine.
LCMS (MH$^+$): m/z=449.0, $t_R$ (minutes, Method E)=2.49. $[\alpha]_D^{20}$=−17.14 (c=1.4 mg/mL, CHCl$_3$)

Example 3f (+)2,3-Dichloro-N-[2-morpholino-2-[2-(trifluoromethyl)pyrimidin-5-yl]ethyl]benzamide LCMS (MH$^+$): m/z=449.0, t$_R$ (minutes, Method E)=2.49. [α]$_D^{20}$=17.47 (c=1.66 mg/mL, CHCl$_3$)

Example 3g (−)2-Chloro-N-[2-morpholino-2-[2-(trifluoromethyl)pyrimidin-5-yl]ethyl]-3-(trifluoromethyl)benzamide

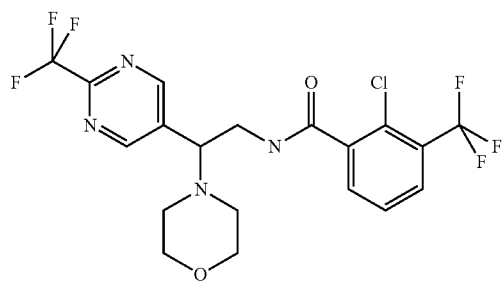 [SMILES: O=C(NCC(c1cnc(C(F)(F)F)nc1)N1CCOCC1)c1cccc(C(F)(F)F)c1Cl]

From 2-chloro-3-(trifluoromethyl)benzoic acid and 2-(2-(trifluoromethyl)pyrimidin-5-yl)-2-morpholin-4-yl-ethylamine.
LCMS (MH$^+$): m/z=483.1, t$_R$ (minutes, Method E)=2.62. [α]$_D^{20}$=−15.09 (c=1.06 mg/mL, CHCl$_3$)

Example 3h (+)2-Chloro-N-[2-morpholino-2-[2-(trifluoromethyl)pyrimidin-5-yl]ethyl]-3-(trifluoromethyl)benzamide LCMS (MH$^+$): m/z=483.1, t$_R$ (minutes, Method E)=2.62. [α]$_D^{20}$=15.04 (c=1.33 mg/mL, CHCl$_3$)

Example 3i (−)2-Chloro-N-[2-morpholino-2-[2-(trifluoromethyl)pyrimidin-5-yl]ethyl]benzamide

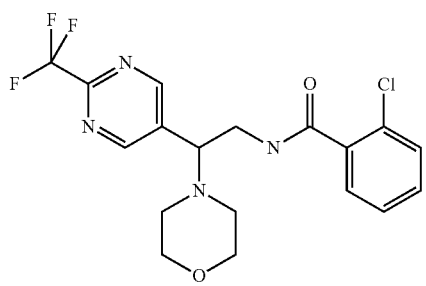 [SMILES: O=C(NCC(c1cnc(C(F)(F)F)nc1)N1CCOCC1)c1ccccc1Cl]

From 2-chlorobenzoic acid and 2-(2-(trifluoromethyl)pyrimidin-5-yl)-2-morpholin-4-yl-ethylamine.
LCMS (MH$^+$): m/z=415.1, t$_R$ (minutes, Method E)=2.30. [α]$_D^{20}$=−16.0 (c=2.00 mg/mL, CHCl$_3$)

Example 3j (+)2-Chloro-N-[2-morpholino-2-[2-(trifluoromethyl)pyrimidin-5-yl]ethyl]benzamide LCMS (MH$^+$): m/z=415.1, t$_R$ (minutes, Method E)=2.30. [α]$_D^{20}$=16.5 (c=2.00 mg/mL, CHCl$_3$)

Example 3k (−)2-Fluoro-N-[2-morpholino-2-[2-(trifluoromethyl)pyrimidin-5-yl]ethyl]benzamide

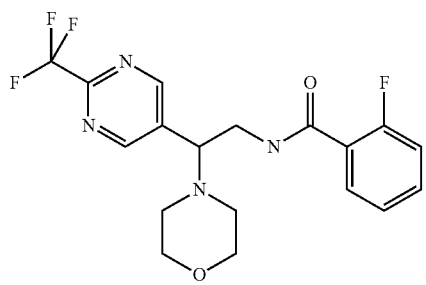 [SMILES: O=C(NCC(c1cnc(C(F)(F)F)nc1)N1CCOCC1)c1ccccc1F]

From 2-fluorobenzoic acid and 2-(2-(trifluoromethyl)pyrimidin-5-yl)-2-morpholin-4-yl-ethylamine.
LCMS (MH$^+$): m/z=399.1, t$_R$ (minutes, Method E)=2.27. [α]$_D^{20}$=−16.9 (c=1.6 mg/mL, CHCl$_3$)

Example 3l (+)2,3-Dichloro-N-[2-(6-methyl-3-pyridyl)-2-morpholino-ethyl]benzamide

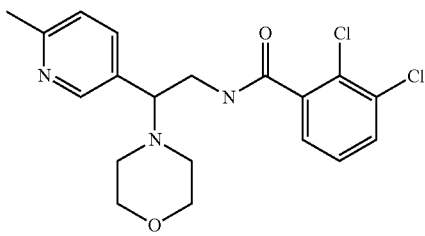 [SMILES: Cc1ccc(C(CNC(=O)c2cccc(Cl)c2Cl)N2CCOCC2)cn1]

From 2,3-dichlorobenzoic acid and 2-(6-methyl-pyridin-3-yl)-2-morpholin-4-yl-ethylamine.
LCMS (MH$^+$): m/z=394.0, t$_R$ (minutes, Method E)=1.79. [α]$_D^{20}$=8.3 (c=4.7 mg/mL, CHCl$_3$)

Example 3m (+)2-Chloro-3-methoxy-N-[2-morpholino-2-[6-(trifluoromethyl)-3-pyridyl]ethyl]benzamide

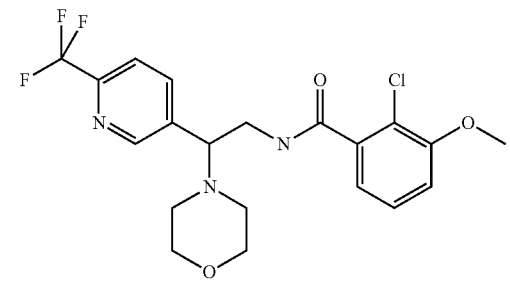 [SMILES: COc1cccc(C(=O)NCC(c2ccc(C(F)(F)F)nc2)N2CCOCC2)c1Cl]

From 2-chloro-3-methoxybenzoic acid and 2-morpholin-4-yl-2-(6-trifluoromethyl-pyridin-3-yl)-ethylamine
LCMS (MH$^+$): m/z=444.2, t$_R$ (minutes, Method E)=2.08. [α]$_D^{20}$=7.5 (c=2.0 mg/mL, CHCl$_3$).

Example 3n (−)2,3-Dichloro-N-[2-(2-methylpyrimidin-5-yl)-2-morpholino-ethyl]benzamide

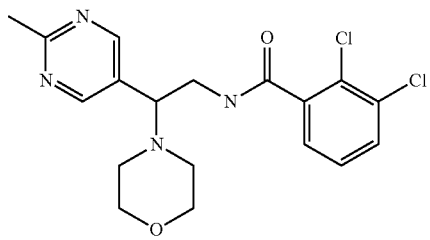 [SMILES: Cc1ncc(C(CNC(=O)c2cccc(Cl)c2Cl)N2CCOCC2)cn1]

From 2,3-dichlorobenzoic acid and 2-(2-methylpyrimidin-5-yl)-2-morpholin-4-yl-ethylamine.
LCMS (MH$^+$): m/z=395.1, t$_R$ (minutes, Method E)=1.56. [α]$_D^{20}$=−6.67 (c=0.9 mg/mL, CHCl$_3$)

Example 3o (+)2,3-Dichloro-N-[2-(2-methylpyrimidin-5-yl)-2-morpholino-ethyl]benzamide LCMS (MH$^+$): m/z=395.1, t$_R$ (minutes, Method E)=1.58. [α]$_D^{20}$=6.9 (c=0.87 mg/mL, CHCl$_3$)

Example 3p (+)2,6-Difluoro-N-[2-morpholino-2-[6-(trifluoromethyl)-3-pyridyl]ethyl]benzamide

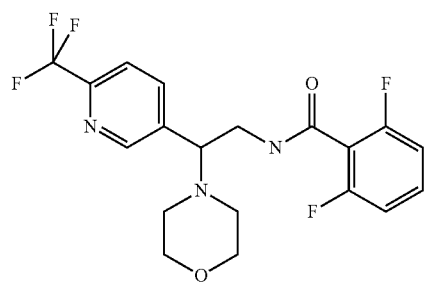 [SMILES: O=C(NCC(c1ccc(C(F)(F)F)nc1)N1CCOCC1)c1c(F)cccc1F]

From 2,6-difluorobenzoic acid and 2-morpholin-4-yl-2-(6-trifluoromethyl-pyridin-3-yl)-ethylamine
LCMS (MH$^+$): m/z=416.2, t$_R$ (minutes, Method E)=1.75. [α]$_D^{20}$=7.9 (c=2.8 mg/mL, CHCl$_3$)

Example 3q (+)2-Methoxy-N-[2-morpholin-4-yl-2-(6-trifluoromethyl-pyridin-3-yl)-ethyl]-benzamide

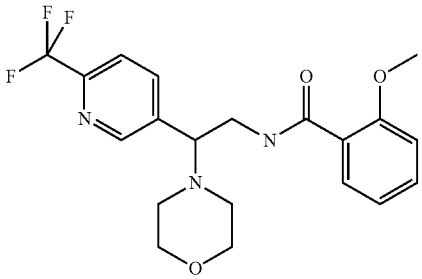 [SMILES: COc1ccccc1C(=O)NCC(c1ccc(C(F)(F)F)nc1)N1CCOCC1]

From 2-methoxybenzoic acid and 2-morpholin-4-yl-2-(6-trifluoromethyl-pyridin-3-yl)-ethylamine
LCMS (MH$^+$): m/z=410.2, t$_R$ (minutes, Method E)=1.96. [α]$_D^{20}$=24.8 (c=7.0 mg/mL, CHCl$_3$).

Example 3r (−)2-Methoxy-N-[2-morpholin-4-yl-2-(6-trifluoromethyl-pyridin-3-yl)-ethyl]-benzamide LCMS (MH$^+$) m/z=410.2, t$_R$ (minutes, Method E)=1.96. [α]$_D^{20}$=−20.7 (c=7.0 mg/mL, CHCl$_3$).

Example 3s (−)2-chloro-3-methoxy-N-(2-morpholino-2-(6-(trifluoromethyl)pyridin-3-yl)ethyl)benzamide

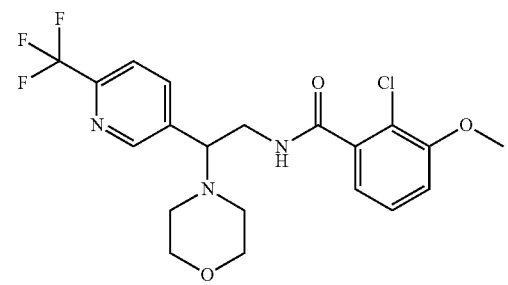 [SMILES: COc1cccc(C(=O)NCC(c2ccc(C(F)(F)F)nc2)N2CCOCC2)c1Cl]

From 2-chloro-3-methoxybenzoic acid and 2-morpholin-4-yl-2-(6-trifluoromethyl-pyridin-3-yl)-ethylamine
LCMS (MH$^+$): m/z=442.2, t$_R$ (minutes, Method F)=2.10. [α]$_D^{20}$=−8.0 (c=1.5 mg/mL, CHCl$_3$).

Example 3t (−)2,6-difluoro-N-(2-morpholino-2-(6-(trifluoromethyl)pyridin-3-yl)ethyl)benzamide

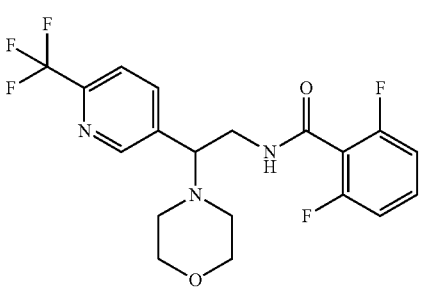

From 2,6-difluorobenzoic acid and 2-morpholin-4-yl-2-(6-trifluoromethyl-pyridin-3-yl)-ethylamine LCMS (MH$^+$): m/z=416.2, $t_R$ (minutes, Method F)=1.73. $[\alpha]_D^{20}$=−7.5 (c=2.4 mg/mL, CHCl$_3$).

Example 3u (+)2-chloro-6-fluoro-N-(2-morpholino-2-(6-(trifluoromethyl)pyridin-3-yl)ethyl)benzamide

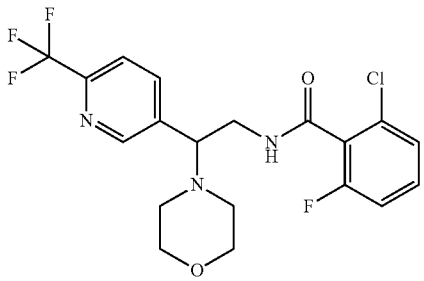 [SMILES: O=C(NCC(c1ccc(C(F)(F)F)nc1)N1CCOCC1)c1c(F)cccc1F]

From 2-chloro-6-fluorobenzoic acid and 2-morpholin-4-yl-2-(6-trifluoromethyl-pyridin-3-yl)-ethylamine LCMS (MH$^+$): m/z=432.2, $t_R$ (minutes, Method F)=2.09. $[\alpha]_D^{20}$=12.1 (c=1.9 mg/mL, CHCl$_3$).

Example 3v (−)2-chloro-6-fluoro-N-(2-morpholino-2-(6-(trifluoromethyl)pyridin-3-yl)ethyl)benzamide LCMS (MH$^+$): m/z=432.2, $t_R$ (minutes, Method F)=2.38. $[\alpha]_D^{20}$=−12.5 (c=2.0 mg/mL, CHCl$_3$).

Example 3x (+)2-chloro-5-(methylsulfonyl)-N-(2-morpholino-2-(6-(trifluoromethyl)pyridin-3-yl)ethyl)benzamide

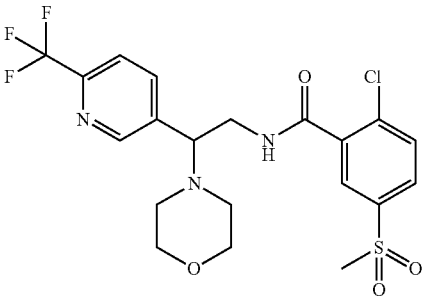 [SMILES: CS(=O)(=O)c1ccc(Cl)c(C(=O)NCC(c2ccc(C(F)(F)F)nc2)N2CCOCC2)c1]

From 2-chloro-5-(methylsulfonyl)benzoic acid and 2-morpholin-4-yl-2-(6-trifluoromethyl-pyridin-3-yl)-ethylamine LCMS (MH$^+$): m/z=492.1, $t_R$ (minutes, Method F)=1.73. $[\alpha]_D^{20}$=5.8 (c=3.6 mg/mL, CHCl$_3$).

Example 3y (−)2-chloro-5-(methylsulfonyl)-N-(2-morpholino-2-(6-(trifluoromethyl)pyridin-3-yl)ethyl)benzamide LCMS (MH$^+$): m/z=492.1, $t_R$ (minutes, Method F)=1.74. $[\alpha]_D^{20}$=−5.8 (c=3.8 mg/mL, CHCl$_3$).

Example 3z (+)2-chloro-N-(2-(2-methylpyrimidin-5-yl)-2-morpholinoethyl)benzamide

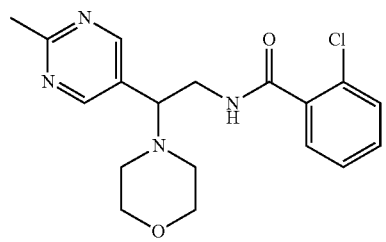 [SMILES: Cc1ncc(C(CNC(=O)c2ccccc2Cl)N2CCOCC2)cn1]

From 2-chlorobenzoic acid and 2-(2-methylpyrimidin-5-yl)-2-morpholinoethanamine

LCMS (MH$^+$): m/z=361.1, $t_R$ (minutes, Method I)=1.48. $[\alpha]_D^{20}$=12.86 (c=2.8 mg/mL, CHCl$_3$).

Example 3a1

(−)2-chloro-N-(2-(2-methylpyrimidin-5-yl)-2-morpholinoethyl)benzamide

LCMS (MH$^+$): m/z=361.1, $t_R$ (minutes, Method I)=1.48. $[\alpha]_D^{20}$=−13.23 (c=3.4 mg/mL, CHCl$_3$).

Example 3b1

(+)2-chloro-N-(2-(4-chlorophenyl)-2-morpholinoethyl)-5-(methylsulfonyl)benzamide

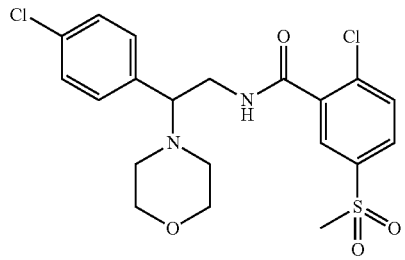 [SMILES: CS(=O)(=O)c1ccc(Cl)c(C(=O)NCC(c2ccc(Cl)cc2)N2CCOCC2)c1]

From 2-chloro-5-(methylsulfonyl)benzoic acid and 2-(4-chlorophenyl)-2-morpholinoethanamine LCMS (MH$^+$): m/z=457.1, $t_R$ (minutes, Method F)=1.96. $[\alpha]_D^{20}$=18.3 (c=1.2 mg/mL, CHCl$_3$).

Example 3c1

(−)2-chloro-N-(2-(4-chlorophenyl)-2-morpholinoethyl)-5-(methylsulfonyl)benzamide LCMS (MH+): m/z=457.1, $t_R$ (minutes, Method F)=195. $[\alpha]_D^{20}$=−17.6 (c=2.6 mg/mL, CHCl$_3$).

Example 3d1

(+)2-chloro-N-(2-(4-chlorophenyl)-2-morpholinoethyl)-5-cyanobenzamide

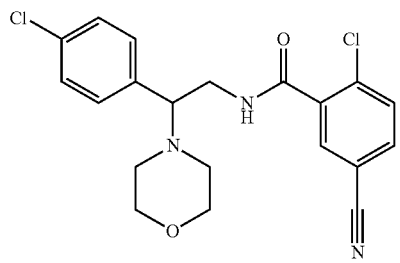 [SMILES: N#Cc1ccc(Cl)c(C(=O)NCC(c2ccc(Cl)cc2)N2CCOCC2)c1]

From 2-chloro-5-cyanobenzoic acid and 2-(4-chlorophenyl)-2-morpholinoethanamine

LCMS (MH+): m/z=404.1, $t_R$ (minutes, Method F)=1.78. $[\alpha]_D^{20}$=5.7 (c=2.3 mg/mL, CHCl$_3$).

Example 3e1

(−)2-chloro-N-(2-(4-chlorophenyl)-2-morpholinoethyl)-5-cyanobenzamide

LCMS (MH+): m/z=404.1, $t_R$ (minutes, Method F)=1.77. $[\alpha]_D^{20}$=−4.6 (c=1.3 mg/mL, CHCl$_3$).

Example 3f1

(−)2-chloro-N-(2-(4-chlorophenyl)-2-morpholinoethyl)-5-(isopropylsulfonyl)benzamide

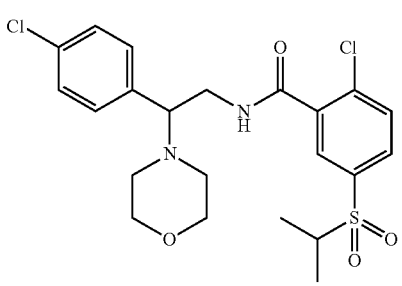 [SMILES: CC(C)S(=O)(=O)c1ccc(Cl)c(C(=O)NCC(c2ccc(Cl)cc2)N2CCOCC2)c1]

From 2-chloro-5-(isopropylsulfonyl)benzoic acid and 2-(4-chlorophenyl)-2-morpholinoethanamine LCMS (MH+): m/z=485.1, $t_R$ (minutes, Method F)=1.90. $[\alpha]_D^{20}$=−5.6 (c=3.56 mg/mL, CHCl$_3$).

Example 3g1

(+)2-chloro-3-fluoro-N-(2-(4,4-difluoropiperidin-1-yl)-2-(2-methylpyrimidin-5-yl)ethyl)benzamide

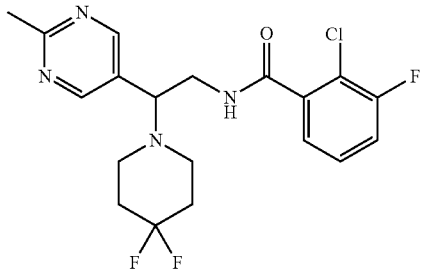 [SMILES: Cc1ncc(C(CNC(=O)c2cccc(F)c2Cl)N2CCC(F)(F)CC2)cn1]

From 2-chloro-3-fluorobenzoic acid and 2-(4,4-difluoropiperidin-1-yl)-2-(2-methylpyrimidin-5-yl)ethanamine LCMS (MH+): m/z=413.2, $t_R$ (minutes, Method F)=1.75. $[\alpha]_D^{20}$=9.06 (c=3.2 mg/mL, CHCl$_3$).

Example 3h1

(−)2-chloro-3-fluoro-N-(2-(4,4-difluoropiperidin-1-yl)-2-(2-methylpyrimidin-5-yl)ethyl)benzamide LCMS (MH+): m/z=413.2, $t_R$ (minutes, Method F)=1.75. $[\alpha]_D^{20}$=−7.74 (c=3.1 mg/mL, CHCl$_3$).

Example 3i1

(+)2-chloro-6-fluoro-N-(2-(4,4-difluoropiperidin-1-yl)-2-(2-methylpyrimidin-5-yl)ethyl)benzamide

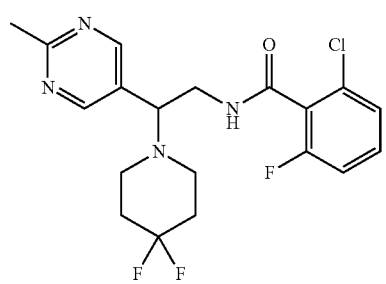 [SMILES: Cc1ncc(C(CNC(=O)c2c(F)cccc2Cl)N2CCC(F)(F)CC2)cn1]

From 2-chloro-6-fluorobenzoic acid and 2-(4,4-difluoropiperidin-1-yl)-2-(2-methylpyrimidin-5-yl)ethanamine LCMS (MH+): m/z=413.2, $t_R$ (minutes, Method F)=1.67. $[\alpha]_D^{20}$=13.56 (c=4.5 mg/mL, CHCl$_3$).

Example 3j1

(−)2-chloro-6-fluoro-N-(2-(4,4-difluoropiperidin-1-yl)-2-(2-methylpyrimidin-5-yl)ethyl)benzamide LCMS (MH+): m/z=413.2, $t_R$ (minutes, Method F)=1.67. $[\alpha]_D^{20}$=−10.21 (c=4.8 mg/mL, CHCl$_3$).

Example 3k1

(+)2-chloro-N-(2-(4,4-difluoropiperidin-1-yl)-2-(2-(trifluoromethyl)pyrimidin-5-yl)ethyl)-3-fluorobenzamide

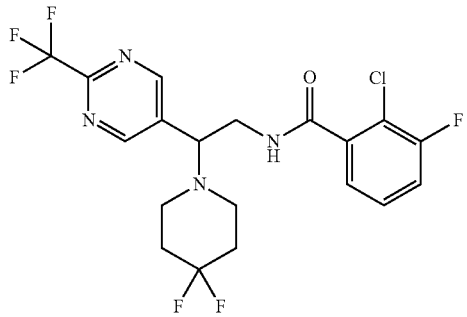 [SMILES: O=C(NCC(c1cnc(C(F)(F)F)nc1)N1CCC(F)(F)CC1)c1cccc(F)c1Cl]

From 2-chloro-3-fluorobenzoic acid and 2-(4,4-difluoropiperidin-1-yl)-2-(2-(trifluoromethyl)pyrimidin-5-yl)ethanamine LCMS (MH$^+$): m/z=467.1, $t_R$ (minutes, Method F)=2.52. $[\alpha]_D^{20}$=9.33 (c=1.5 mg/mL, CHCl$_3$).

Example 3l1

(−)2-chloro-N-(2-(4,4-difluoropiperidin-1-yl)-2-(2-(trifluoromethyl)pyrimidin-5-yl)ethyl)-3-fluorobenzamide LCMS (MH$^+$): m/z=467.2, $t_R$ (minutes, Method F)=2.52. $[\alpha]_D^{20}$=−8.57 (c=1.4 mg/mL, CHCl$_3$).

Example 3 m1

(+)2-chloro-6-fluoro-N-(2-(4,4-difluoropiperidin-1-yl)-2-(2-(trifluoromethyl)pyrimidin-5-yl)ethyl)benzamide

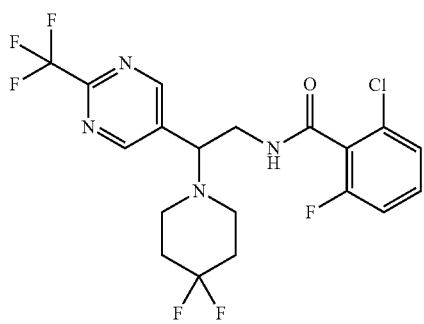 [SMILES: O=C(NCC(c1cnc(C(F)(F)F)nc1)N1CCC(F)(F)CC1)c1c(F)cccc1Cl]

From 2-chloro-6-fluorobenzoic acid and 2-(4,4-difluoropiperidin-1-yl)-2-(2-(trifluoromethyl)pyrimidin-5-yl)ethanamine LCMS (MH$^+$): m/z=467.1, $t_R$ (minutes, Method F)=2.5. $[\alpha]_D^{20}$=19.32 (c=2.07 mg/mL, CHCl$_3$).

Example 3n1

(−)2-chloro-6-fluoro-N-(2-(4,4-difluoropiperidin-1-yl)-2-(trifluoromethyl)pyrimidin-5-yl)ethyl)benzamide LCMS (MH$^+$): m/z=467.1, $t_R$ (minutes, Method F)=2.5. $[\alpha]_D^{20}$=−18.87 (c=1.59 mg/mL, CHCl$_3$).

Example 3o1

(+)2-chloro-3-fluoro-N-(2-(4,4-difluoropiperidin-1-yl)-2-(2-methylpyridin-5-yl)ethyl)benzamide

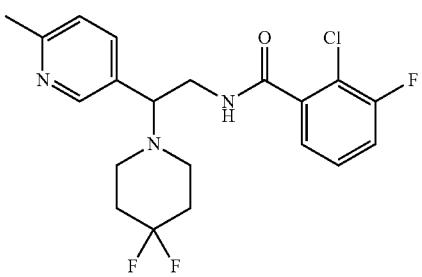 [SMILES: Cc1ccc(C(CNC(=O)c2cccc(F)c2Cl)N2CCC(F)(F)CC2)cn1]

From 2-chloro-3-fluorobenzoic acid and 2-(4,4-difluoropiperidin-1-yl)-2-(2-methylpyridin-5-yl)ethanamine LCMS (MH$^+$): m/z=412.2, $t_R$ (minutes, Method F)=1.69. $[\alpha]_D^{20}$=13.24 (c=3.4 mg/mL, CHCl$_3$).

Example 3p1

(−)2-chloro-3-fluoro-N-(2-(4,4-difluoropiperidin-1-yl)-2-(2-methylpyridin-5-yl)ethyl)benzamide LCMS (MH$^+$): m/z=412.2, $t_R$ (minutes, Method F)=1.70. $[\alpha]_D^{20}$=−13.71 (c=3.5 mg/mL, CHCl$_3$).

Example 3q1

(+)2-chloro-N-(2-(4,4-difluoropiperidin-1-yl)-2-(6-methylpyridin-3-yl)ethyl)-6-fluorobenzamide

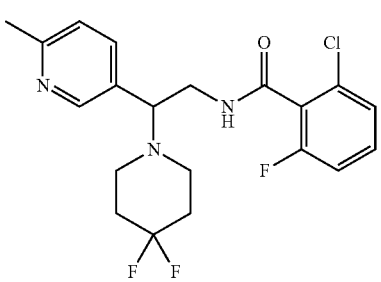 [SMILES: Cc1ccc(C(CNC(=O)c2c(F)cccc2Cl)N2CCC(F)(F)CC2)cn1]

From 2-chloro-6-fluorobenzoic acid and 2-(4,4-difluoropiperidin-1-yl)-2-(2-methylpyridin-5-yl)ethanamine LCMS (MH$^+$): m/z=412.2, $t_R$ (minutes, Method F)=1.64. $[\alpha]_D^{20}$=15.79 (c=3.8 mg/mL, CHCl$_3$).

Example 3r1

(−)2-chloro-N-(2-(4,4-difluoropiperidin-1-yl)-2-(6-methylpyridin-3-yl)ethyl)-6-fluorobenzamide LCMS (MH+): m/z=412.2, $t_R$ (minutes, Method F)=1.64. $[\alpha]_D^{20}$=−15.14 (c=3.5 mg/mL, CHCl$_3$).

Example 3s1

(+)2-chloro-N-(2-(4,4-difluoropiperidin-1-yl)-2-(2-(trifluoromethyl)pyridin-5-yl)ethyl)-3-fluorobenzamide

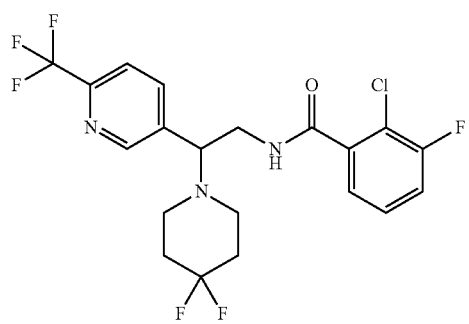 [SMILES: O=C(NCC(c1ccc(C(F)(F)F)nc1)N1CCC(F)(F)CC1)c1cccc(F)c1Cl]

From 2-chloro-3-fluorobenzoic acid and 2-(4,4-difluoropiperidin-1-yl)-2-(2-(trifluoromethyl)pyridin-5-yl)ethanamine LCMS (MH+): m/z=466.1, $t_R$ (minutes, Method F)=2.29. $[\alpha]_D^{20}$=10.97 (c=3.1 mg/mL, CHCl$_3$).

Example 3t1

(−)2-chloro-N-(2-(4,4-difluoropiperidin-1-yl)-2-(2-(trifluoromethyl)pyridin-5-yl)ethyl)-3-fluorobenzamide LCMS (MH+): m/z=466.1, $t_R$ (minutes, Method F)=2.30. $[\alpha]_D^{20}$=−9.69 (c=3.2 mg/mL, CHCl$_3$).

Example 3u1

(+)2-chloro-6-fluoro-N-(2-(4,4-difluoropiperidin-1-yl)-2-(2-(trifluoromethyl)pyridin-5-yl)ethyl)benzamide

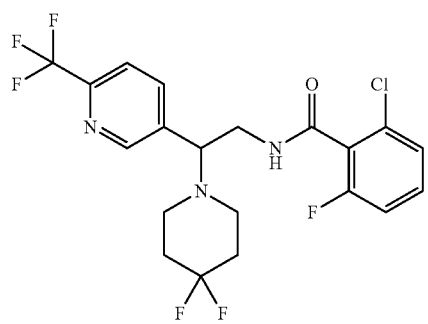 [SMILES: O=C(NCC(c1ccc(C(F)(F)F)nc1)N1CCC(F)(F)CC1)c1c(F)cccc1Cl]

From 2-chloro-6-fluorobenzoic acid and 2-(4,4-difluoropiperidin-1-yl)-2-(2-(trifluoromethyl)pyridin-5-yl)ethanamine LCMS (MH+): m/z=466.1, $t_R$ (minutes, Method F)=2.27. $[\alpha]_D^{20}$=12.14 (c=2.8 mg/mL, CHCl$_3$).

Example 3v1

(−)2-chloro-6-fluoro-N-(2-(4,4-difluoropiperidin-1-yl)-2-(2-(trifluoromethyl)pyridin-5-yl)ethyl)benzamide LCMS (MH+): m/z=466.1, $t_R$ (minutes, Method F)=2.27. $[\alpha]_D^{20}$=−12.96 (c=2.7 mg/mL, CHCl$_3$).

Example 3x1

(+)2-chloro-3-methoxy-N-(2-morpholino-2-(2-(trifluoromethyl)pyrimidin-5-yl)ethyl)benzamide

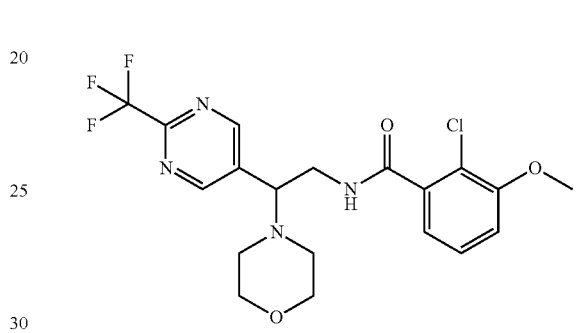

From 2-chloro-3-methoxybenzoic acid and 2-morpholino-2-(2-(trifluoromethyl)pyrimidin-5-yl)ethanamine LCMS (MH+): m/z=445.1, $t_R$ (minutes, Method F)=1.91. $[\alpha]_D^{20}$=6.4 (c=4.2 mg/mL, CHCl$_3$).

Example 3z1

(−)2-chloro-3-methoxy-N-(2-morpholino-2-(2-(trifluoromethyl)pyrimidin-5-yl)ethyl)benzamide LCMS (MH+): m/z=445.1, $t_R$ (minutes, Method F)=1.91. $[\alpha]_D^{20}$=−8.25 (c=4.0 mg/mL, CHCl$_3$).

Example 3a2

(+)2-chloro-3-methoxy-N-(2-morpholino-2-(2-(trifluoromethyl)pyridin-5-yl)ethyl)benzamide

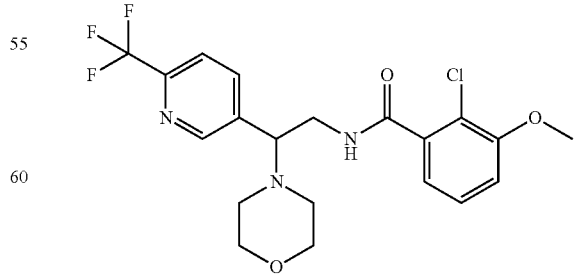

From 2-chloro-3-methoxybenzoic acid and 2-morpholino-2-(2-(trifluoromethyl)pyridin-5-yl)ethanamine LCMS (MH$^+$): m/z=424.2, $t_R$ (minutes, Method F)=1.84. [α]$_D^{20}$=5.3 (c=8.6 mg/mL, CHCl$_3$).

Example 3h2

(−)2-chloro-3-methoxy-N-(2-morpholino-2-(2-(trifluoromethyl)pyridin-5-yl)ethyl)benzamide LCMS (MH$^+$): m/z=424.2, $t_R$ (minutes, Method F)=1.85. [α]$_D^{20}$=−4.3 (c=7.9 mg/mL, CHCl$_3$).

Example 3c2

(+)2-chloro-N-(2-(4-chlorophenyl)-2-morpholinoethyl)-3-methoxybenzamide

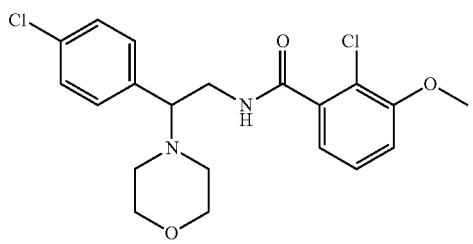 [SMILES: COc1cccc(C(=O)NCC(c2ccc(Cl)cc2)N2CCOCC2)c1Cl]

From 2-chloro-3-methoxybenzoic acid and 2-(4-chlorophenyl)-2-morpholinoethanamine
LCMS (MH$^+$): m/z=409.1, $t_R$ (minutes, Method F)=1.79. [α]$_D^{20}$=11.5 (c=7.2 mg/mL, CHCl$_3$).

Example 3d2

(−)2-chloro-N-(2-(4-chlorophenyl)-2-morpholinoethyl)-3-methoxybenzamide

LCMS (MH$^+$): m/z=409.1, $t_R$ (minutes, Method F)=1.78. [α]$_D^{20}$=−12.2 (c=6.6 mg/mL, CHCl$_3$).

Example 3e2

(+)2-chloro-N-(2-(4,4-difluoropiperidin-1-yl)-2-(4-fluorophenyl)ethyl)-3-methoxybenzamide

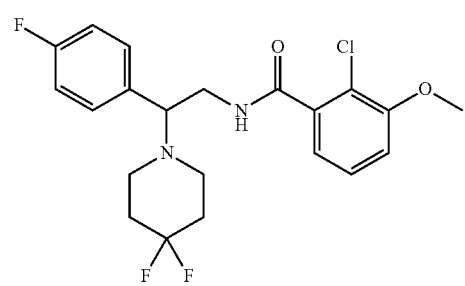 [SMILES: COc1cccc(C(=O)NCC(c2ccc(F)cc2)N2CCC(F)(F)CC2)c1Cl]

From 2-chloro-3-methoxybenzoic acid and 2-(4,4-difluoropiperidin-1-yl)-2-(4-fluorophenyl)ethanamine LCMS (MH$^+$): m/z=427.1, $t_R$ (minutes, Method F)=1.55. [α]$_D^{20}$=9.1 (c=8.1 mg/mL, CHCl$_3$).

Example 3f2

(−)2-chloro-N-(2-(4,4-difluoropiperidin-1-yl)-2-(4-fluorophenyl)ethyl)-3-methoxybenzamide LCMS (MH$^+$): m/z=427.2, $t_R$ (minutes, Method F)=1.58. [α]$_D^{20}$=−10.8 (c=7.9 mg/mL, CHCl$_3$).

Example 3g2

(+)2,3-dichloro-N-(2-(3,3-difluoropiperidin-1-yl)-2-(2-methylpyrimidin-5-yl)ethyl)benzamide

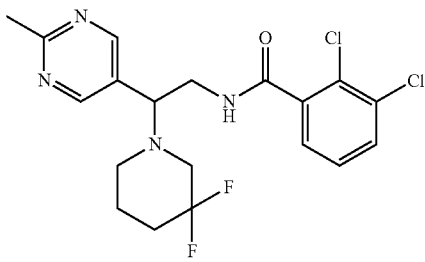 [SMILES: Cc1ncc(C(CNC(=O)c2cccc(Cl)c2Cl)N2CCCC(F)(F)C2)cn1]

From 2,3-dichlorobenzoic acid and 2-(3,3-difluoropiperidin-1-yl)-2-(2-methylpyrimidin-5-yl)ethanamine
LCMS (MH$^+$): m/z=429.0, $t_R$ (minutes, Method F)=2.52. [α]$_D^{20}$=7.0 (c=4.8 mg/mL, CHCl$_3$).

Example 3h2

(−)2,3-dichloro-N-(2-(3,3-difluoropiperidin-1-yl)-2-(2-methylpyrimidin-5-yl)ethyl)benzamide LCMS (MH$^+$): m/z=429.0, $t_R$ (minutes, Method F)=2.52. [α]$_D^{20}$=−7.6 (c=6.0 mg/mL, CHCl$_3$).

Example 3g2

(+)2-chloro-N-(2-(3,3-difluoropiperidin-1-yl)-2-(2-methylpyrimidin-5-yl)ethyl)benzamide

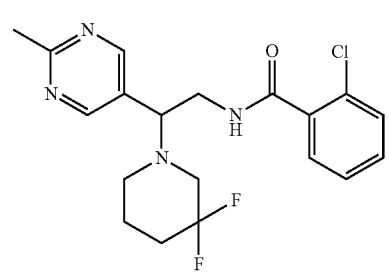 [SMILES: Cc1ncc(C(CNC(=O)c2ccccc2Cl)N2CCCC(F)(F)C2)cn1]

From 2-chlorobenzoic acid and 2-(3,3-difluoropiperidin-1-yl)-2-(2-methylpyrimidin-5-yl)ethanamine LCMS (MH+): m/z=395.1, $t_R$ (minutes, Method F)=2.32. $[\alpha]_D^{20}$=7.8 (c=5.0 mg/mL, CHCl$_3$).

Example 3h2

(−)2-chloro-N-(2-(3,3-difluoropiperidin-1-yl)-2-(2-methylpyrimidin-5-yl)ethyl)benzamide LCMS (MH+): m/z=395.1, $t_R$ (minutes, Method F)=2.32. $[\alpha]_D^{20}$=−7.0 (c=5.1 mg/mL, CHCl$_3$).

Example 3g2

(+)2-chloro-3-fluoro-N-(2-(3,3-difluoropiperidin-1-yl)-2-(2-methylpyrimidin-5-yl)ethyl)benzamide

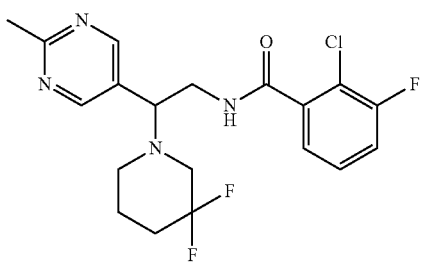 [SMILES: Cc1ncc(C(CNC(=O)c2cccc(F)c2Cl)N2CCCC(F)(F)C2)cn1]

From 2-chloro-3-fluorobenzoic acid and 2-(3,3-difluoropiperidin-1-yl)-2-(2-methylpyrimidin-5-yl)ethanamine LCMS (MH+): m/z=413.1, $t_R$ (minutes, Method F)=2.41. $[\alpha]_D^{20}$=8.4 (c=5.0 mg/mL, CHCl$_3$).

Example 3h2

(−)2-chloro-3-fluoro-N-(2-(3,3-difluoropiperidin-1-yl)-2-(2-methylpyrimidin-5-yl)ethyl)benzamide LCMS (MH+): m/z=413.1, $t_R$ (minutes, Method F)=2.42. $[\alpha]_D^{20}$=−7.8 (c=4.6 mg/mL, CHCl$_3$).

Example 3g2

(+)2-chloro-6-fluoro-N-(2-(3,3-difluoropiperidin-1-yl)-2-(2-methylpyrimidin-5-yl)ethyl)benzamide

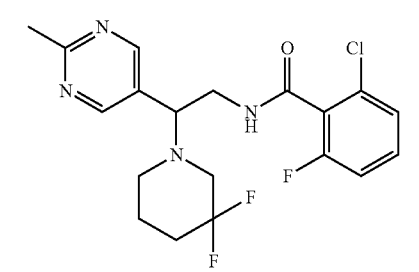 [SMILES: Cc1ncc(C(CNC(=O)c2c(F)cccc2Cl)N2CCCC(F)(F)C2)cn1]

From 2-chloro-6-fluorobenzoic acid and 2-(3,3-difluoropiperidin-1-yl)-2-(2-methylpyrimidin-5-yl)ethanamine LCMS (MH+): m/z=413.1, $t_R$ (minutes, Method F)=2.33. $[\alpha]_D^{20}$=10.5 (c=5.4 mg/mL, CHCl$_3$).

Example 3h2

(−)2-chloro-6-fluoro-N-(2-(3,3-difluoropiperidin-1-yl)-2-(2-methylpyrimidin-5-yl)ethyl)benzamide LCMS (MH+): m/z=413.1, $t_R$ (minutes, Method F)=2.33. $[\alpha]_D^{20}$=−9.5 (c=4.3 mg/mL, CHCl$_3$).

Example 3i2

(+)2-chloro-N-(2-(4-fluoropiperidin-1-yl)-2-(2-methylpyrimidin-5-yl)ethyl)benzamide

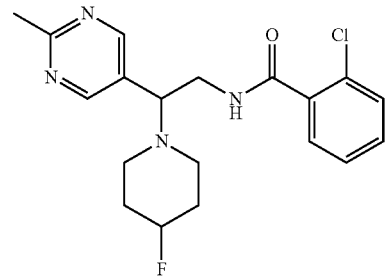 [SMILES: Cc1ncc(C(CNC(=O)c2ccccc2Cl)N2CCC(F)CC2)cn1]

From 2-chlorobenzoic acid and 2-(4-fluoropiperidin-1-yl)-2-(2-methylpyrimidin-5-yl)ethanamine LCMS (MH+): m/z=377.1, $t_R$ (minutes, Method F)=1.64. $[\alpha]_D^{20}$=3.0 (c=6.0 mg/mL, CHCl$_3$).

Example 3j2

(−)2-chloro-N-(2-(4-fluoropiperidin-1-yl)-2-(2-methylpyrimidin-5-yl)ethyl)benzamide LCMS (MH+): m/z=377.1, $t_R$ (minutes, Method F)=1.63. $[\alpha]_D^{20}$=−3.06 (c=6.2 mg/mL, CHCl$_3$).

Example 3k2

(+)2,3-dichloro-N-(2-(4-fluoropiperidin-1-yl)-2-(2-methylpyrimidin-5-yl)ethyl)benzamide

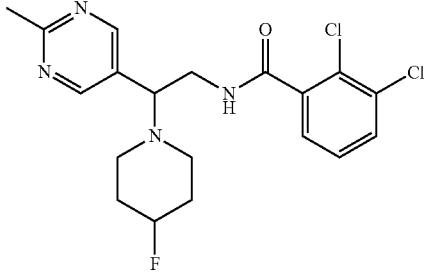

From 2,3-dichlorobenzoic acid and 2-(4-fluoropiperidin-1-yl)-2-(2-methylpyrimidin-5-yl)ethanamine LCMS (MH⁺): m/z=411.1, $t_R$ (minutes, Method F)=1.85. $[\alpha]_D^{20}$=3.14 (c=5.73 mg/mL, CHCl₃).

Example 3l2

(−)2,3-dichloro-N-(2-(4-fluoropiperidin-1-yl)-2-(2-methylpyrimidin-5-yl)ethyl)benzamide LCMS (MH⁺): m/z=411.1, $t_R$ (minutes, Method F)=1.85. $[\alpha]_D^{20}$=−3.32 (c=6.03 mg/mL, CHCl₃).

Example 3m2

(+)2,6-dichloro-N-(2-(4-fluoropiperidin-1-yl)-2-(2-methylpyrimidin-5-yl)ethyl)benzamide

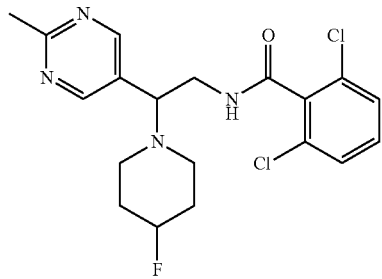 [SMILES: Cc1ncc(C(CNC(=O)c2c(Cl)cccc2Cl)N2CCC(F)CC2)cn1]

From 2,6-dichlorobenzoic acid and 2-(4-fluoropiperidin-1-yl)-2-(2-methylpyrimidin-5-yl)ethanamine
LCMS (MH⁺): m/z=411.1, $t_R$ (minutes, Method F)=1.70. $[\alpha]_D^{20}$=9.83 (c=6.0 mg/mL, CHCl₃).

Example 3n2

(−)2,6-dichloro-N-(2-(4-fluoropiperidin-1-yl)-2-(2-methylpyrimidin-5-yl)ethyl)benzamide LCMS (MH⁺): m/z=411.1, $t_R$ (minutes, Method F)=1.69. $[\alpha]_D^{20}$=−10.0 (c=5.1 mg/mL, CHCl₃).

Example 3o2

(+)2-chloro-N-(2-(4-fluoropiperidin-1-yl)-2-(2-(trifluoromethyl)pyrimidin-5-yl)ethyl)benzamide

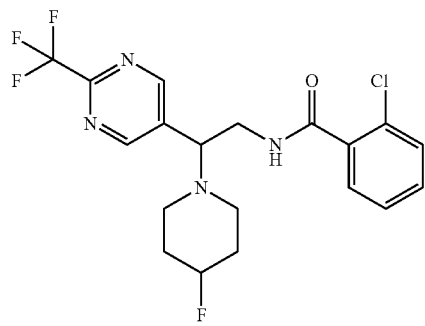 [SMILES: O=C(NCC(c1cnc(C(F)(F)F)nc1)N1CCC(F)CC1)c1ccccc1Cl]

From 2-chlorobenzoic acid and 2-(4-fluoropiperidin-1-yl)-2-(2-(trifluoromethyl)pyrimidin-5-yl)ethanamine LCMS (MH⁺): m/z=431.1, $t_R$ (minutes, Method F)=1.90. $[\alpha]_D^{20}$=13.1 (c=2.6 mg/mL, CHCl₃).

Example 3p2

(−)2-chloro-N-(2-(4-fluoropiperidin-1-yl)-2-(2-(trifluoromethyl)pyrimidin-5-yl)ethyl)benzamide LCMS (MH⁺): m/z=431.1, $t_R$ (minutes, Method F)=1.91. $[\alpha]_D^{20}$=−11.5 (c=2.7 mg/mL, CHCl₃).

Example 3q2

(+)2,3-dichloro-N-(2-(4-fluoropiperidin-1-yl)-2-(2-(trifluoromethyl)pyrimidin-5-yl)ethyl)benzamide

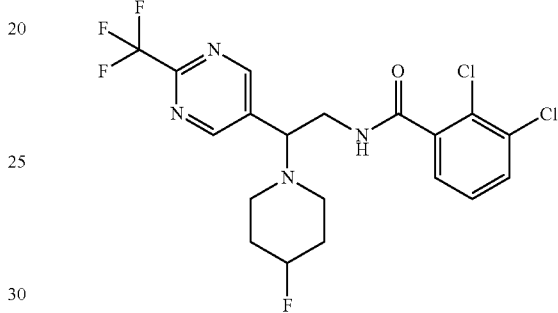

From 2,3-dichlorobenzoic acid and 2-(4-fluoropiperidin-1-yl)-2-(2-(trifluoromethyl)pyrimidin-5-yl)ethanamine
LCMS (MH⁺): m/z=465.0, $t_R$ (minutes, Method F)=2.39. $[\alpha]_D^{20}$=6.4 (c=2.8 mg/mL, CHCl₃).

Example 3r2

(−)2,3-dichloro-N-(2-(4-fluoropiperidin-1-yl)-2-(2-(trifluoromethyl)pyrimidin-5-yl)ethyl)benzamide LCMS (MH⁺): m/z=465.1, $t_R$ (minutes, Method F)=2.10. $[\alpha]_D^{20}$=−6.6 (c=3.8 mg/mL, CHCl₃).

Example 3s2

(+)2,6-dichloro-N-(2-(4-fluoropiperidin-1-yl)-2-(2-(trifluoromethyl)pyrimidin-5-yl)ethyl)benzamide

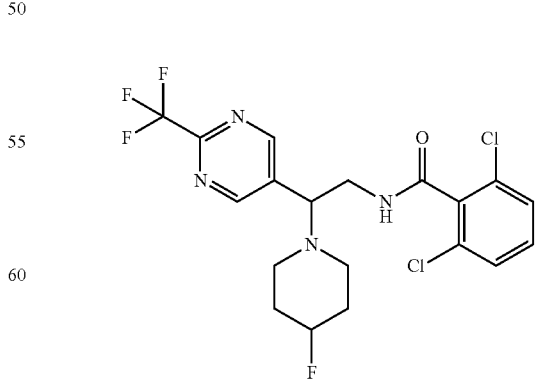

From 2,6-dichlorobenzoic acid and 2-(4-fluoropiperidin-1-yl)-2-(2-(trifluoromethyl)pyrimidin-5-yl)ethanamine LCMS (MH$^+$): m/z=465.1, $t_R$ (minutes, Method F)=2.00. $[\alpha]_D^{20}$=12.2 (c=2.3 mg/mL, CHCl$_3$).

Example 3t2

(−)2,6-dichloro-N-(2-(4-fluoropiperidin-1-yl)-2-(2-(trifluoromethyl)pyrimidin-5-yl)ethyl)benzamide LCMS (MH$^+$): m/z=465.1, $t_R$ (minutes, Method F)=1.99. $[\alpha]_D^{20}$=−12.7 (c=1.5 mg/mL, CHCl$_3$).

Example 3u2

(+)2-chloro-N-(2-(4,4-difluoropiperidin-1-yl)-2-(1-methyl-1H-pyrazol-4-yl)ethyl)benzamide

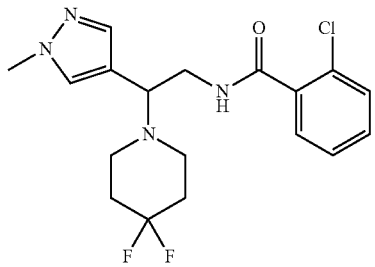 [SMILES: Cn1cc(C(CNC(=O)c2ccccc2Cl)N2CCC(F)(F)CC2)cn1]

From 2-chlorobenzoic acid and 2-(4,4-difluoropiperidin-1-yl)-2-(1-methyl-1H-pyrazol-4-yl)ethanamine LCMS (MH$^+$): m/z=383.1, $t_R$ (minutes, Method F)=1.70. $[\alpha]_D^{20}$=8.6 (c=1.8 mg/mL, CHCl$_3$).

Example 3v2

(−)2-chloro-N-(2-(4,4-difluoropiperidin-1-yl)-2-(1-methyl-1H-pyrazol-4-yl)ethyl)benzamide LCMS (MH$^+$): m/z=383.1, $t_R$ (minutes, Method F)=1.70. $[\alpha]_D^{20}$=−7.1 (c=1.8 mg/mL, CHCl$_3$).

Example 3u2

(+)2,3-dichloro-N-(2-(4,4-difluoropiperidin-1-yl)-2-(1-methyl-1H-pyrazol-4-yl)ethyl)benzamide

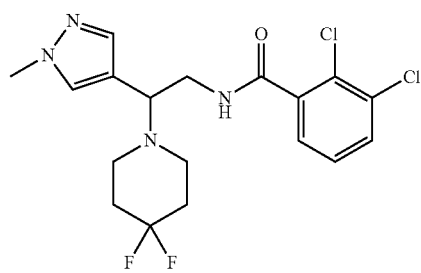 [SMILES: Cn1cc(C(CNC(=O)c2cccc(Cl)c2Cl)N2CCC(F)(F)CC2)cn1]

From 2,3-dichlorobenzoic acid and 2-(4,4-difluoropiperidin-1-yl)-2-(1-methyl-1H-pyrazol-4-yl)ethanamine LCMS (MH$^+$): m/z=417.0, $t_R$ (minutes, Method F)=1.91. $[\alpha]_D^{20}$=11.1 (c=2.4 mg/mL, CHCl$_3$).

Example 3v2

(−)2,3-dichloro-N-(2-(4,4-difluoropiperidin-1-yl)-2-(1-methyl-1H-pyrazol-4-yl)ethyl)benzamide LCMS (MH$^+$): m/z=417.0, $t_R$ (minutes, Method F)=1.91. $[\alpha]_D^{20}$=−11.5 (c=2.3 mg/mL, CHCl$_3$).

Example 3u2

(+)2,6-dichloro-N-(2-(4,4-difluoropiperidin-1-yl)-2-(1-methyl-1H-pyrazol-4-yl)ethyl)benzamide

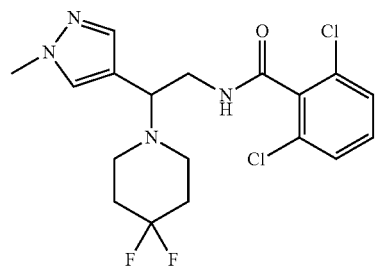 [SMILES: Cn1cc(C(CNC(=O)c2c(Cl)cccc2Cl)N2CCC(F)(F)CC2)cn1]

From 2,6-dichlorobenzoic acid and 2-(4,4-difluoropiperidin-1-yl)-2-(1-methyl-1H-pyrazol-4-yl)ethanamine LCMS (MH$^+$): m/z=417.0, $t_R$ (minutes, Method F)=1.75. $[\alpha]_D^{20}$=7.9 (c=4.9 mg/mL, CHCl$_3$).

Example 3v2

(−)2,6-dichloro-N-(2-(4,4-difluoropiperidin-1-yl)-2-(1-methyl-1H-pyrazol-4-yl)ethyl)benzamide LCMS (MH$^+$): m/z=417.0, $t_R$ (minutes, Method F)=1.76. $[\alpha]_D^{20}$=−8.7 (c=4.0 mg/mL, CHCl$_3$).

Example 3u2

(+)2,3-dichloro-5-fluoro-N-(2-(4,4-difluoropiperidin-1-yl)-2-(1-methyl-1H-pyrazol-4-yl)ethyl)benzamide

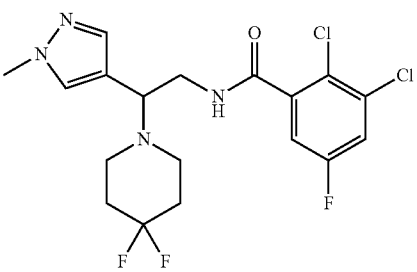 [SMILES: Cn1cc(C(CNC(=O)c2cc(F)cc(Cl)c2Cl)N2CCC(F)(F)CC2)cn1]

From 2,3-dichloro-5-fluorobenzoic acid and 2-(4,4-difluoropiperidin-1-yl)-2-(1-methyl-1H-pyrazol-4-yl)ethanamine LCMS (MH$^+$): m/z=435.0, $t_R$ (minutes, Method F)=1.97. $[\alpha]_D^{20}$=12.7 (c=3.7 mg/mL, CHCl$_3$).

Example 3v2

(−)2,3-dichloro-5-fluoro-N-(2-(4,4-difluoropiperidin-1-yl)-2-(1-methyl-1H-pyrazol-4-yl)ethyl)benzamide LCMS (MH$^+$): m/z=435.0, $t_R$ (minutes, Method F)=1.97. $[\alpha]_D^{20}$=−11.3 (c=3.7 mg/mL, CHCl$_3$).

Example 3x2

(+)2-chloro-N-(2-(4,4-difluoropiperidin-1-yl)-2-(2-(trifluoromethyl)pyrimidin-5-yl)ethyl)-3-methoxybenzamide

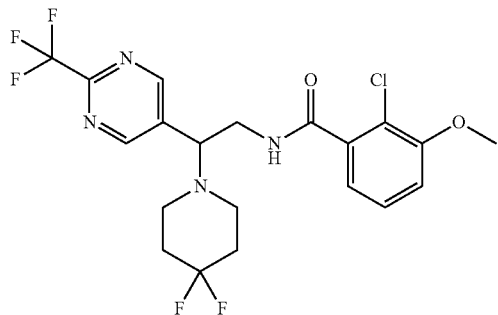 [SMILES: COc1cccc(C(=O)NCC(c2cnc(C(F)(F)F)nc2)N2CCC(F)(F)CC2)c1Cl]

From 2-chloro-3-methoxybenzoic acid and 2-(4,4-difluoropiperidin-1-yl)-2-(2-(trifluoromethyl)pyrimidin-5-yl)ethanamine LCMS (MH$^+$): m/z=479.1, $t_R$ (minutes, Method F)=2.73. $[\alpha]_D^{20}$=4.22 (c=3.0 mg/mL, CHCl$_3$).

Example 3y2

(−)2-chloro-N-(2-(4,4-difluoropiperidin-1-yl)-2-(2-(trifluoromethyl)pyrimidin-5-yl)ethyl)-3-methoxybenzamide LCMS (MH$^+$): m/z=479.1, $t_R$ (minutes, Method F)=2.73. $[\alpha]_D^{20}$=−3.95 (c=3.8 mg/mL, CHCl$_3$).

Example 3z2

(+)2,6-dichloro-N-(2-(4,4-difluoropiperidin-1-yl)-2-(2-(trifluoromethyl)pyrimidin-5-yl)ethyl)benzamide

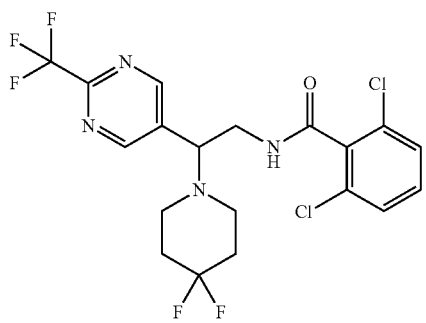

From 2,6-dichlorobenzoic acid and 2-(4,4-difluoropiperidin-1-yl)-2-(2-(trifluoromethyl)pyrimidin-5-yl)ethanamine LCMS (MH$^+$): m/z=483.0, $t_R$ (minutes, Method F)=2.88. $[\alpha]_D^{20}$=4.85 (c=2.2 mg/mL, CHCl$_3$).

Example 3a3

(−)2,6-dichloro-N-(2-(4,4-difluoropiperidin-1-yl)-2-(2-(trifluoromethyl)pyrimidin-5-yl)ethyl)benzamide LCMS (MH$^+$): m/z=483.0, $t_R$ (minutes, Method F)=2.85. $[\alpha]_D^{20}$=−5.76 (c=2.2 mg/mL, CHCl$_3$).

Example 3b3

(+)2,6-dichloro-5-fluoro-N-(2-(4,4-difluoropiperidin-1-yl)-2-(2-(trifluoromethyl)pyrimidin-5-yl)ethyl)benzamide

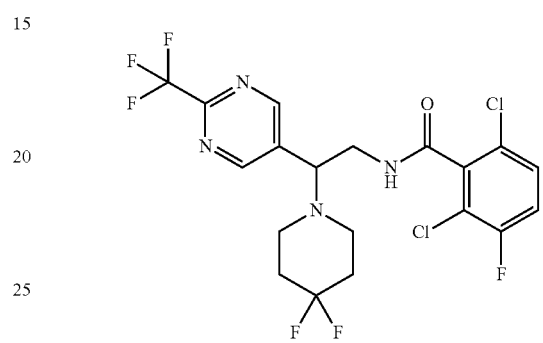

From 2,6-dichloro-5-fluorobenzoic acid and 2-(4,4-difluoropiperidin-1-yl)-2-(2-(trifluoromethyl)pyrimidin-5-yl)ethanamine LCMS (MH$^+$): m/z=501.0, $t_R$ (minutes, Method F)=295. $[\alpha]_D^{20}$=6.33 (c=2.0 mg/mL, CHCl$_3$).

Example 3c3

(−)2,6-dichloro-5-fluoro-N-(2-(4,4-difluoropiperidin-1-yl)-2-(2-(trifluoromethyl)pyrimidin-5-yl)ethyl)benzamide LCMS (MH$^+$): m/z=501.0, $t_R$ (minutes, Method F)=2.95. $[\alpha]_D^{20}$=−8.0 (c=2.0 mg/mL, CHCl$_3$).

Example 3d3

(+)2,3-dichloro-5-fluoro-N-(2-(4,4-difluoropiperidin-1-yl)-2-(2-(trifluoromethyl)pyrimidin-5-yl)ethyl)benzamide

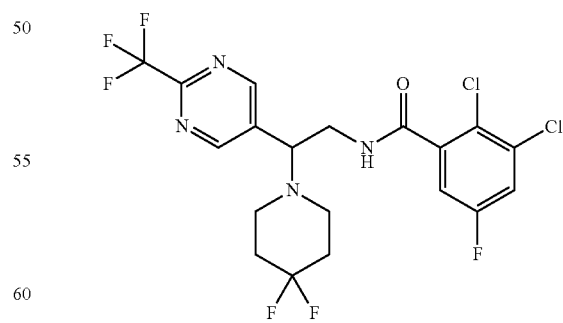

From 2,3-dichloro-5-fluorobenzoic acid and 2-(4,4-difluoropiperidin-1-yl)-2-(2-(trifluoromethyl)pyrimidin-5-yl)ethanamine LCMS (MH$^+$): m/z=501.1, $t_R$ (minutes, Method F)=2.75. $[\alpha]_D^{20}$=2.94 (c=4.2 mg/mL, CHCl$_3$).

Example 3e3

(−)2,3-dichloro-5-fluoro-N-(2-(4,4-difluoropiperidin-1-yl)-2-(2-(trifluoromethyl)pyrimidin-5-yl)ethyl)benzamide LCMS (MH$^+$): m/z=501.1, $t_R$ (minutes, Method F)=2.75. $[\alpha]_D^{20}$=−3.33 (c=3.8 mg/mL, CHCl$_3$).

Example 3f3

(+)2-chloro-N-(2-(2-methylpyrimidin-5-yl)-2-(piperidin-1-yl)ethyl)benzamide

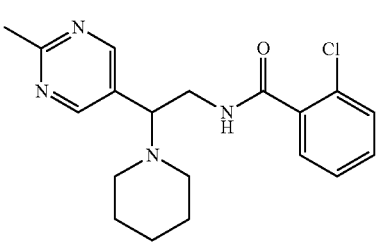 [SMILES: Cc1ncc(C(CNC(=O)c2ccccc2Cl)N2CCCCC2)cn1]

From 2-chlorobenzoic acid and 2-(piperidin-1-yl)-2-(2-methylpyrimidin-5-yl)ethanamine LCMS (MH$^+$): m/z=359.2, $t_R$ (minutes, Method F)=1.47. $[\alpha]_D^{20}$=6.67 (c=2.8 mg/mL, CHCl$_3$).

Example 3g3

(−)2-chloro-N-(2-(2-methylpyrimidin-5-yl)-2-(piperidin-1-yl)ethyl)benzamide

LCMS (MH$^+$): m/z=359.2, $t_R$ (minutes, Method F)=1.47. $[\alpha]_D^{20}$=−5.04 (c=2.38 mg/mL, CHCl$_3$).

Example 3h3

(+2,3-dichloro-N-(2-(2-methylpyrimidin-5-yl)-2-(piperidin-1-yl)ethyl)benzamide

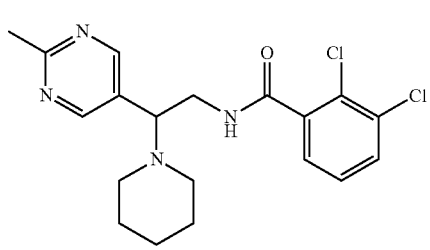 [SMILES: Cc1ncc(C(CNC(=O)c2cccc(Cl)c2Cl)N2CCCCC2)cn1]

From 2,3-dichlorobenzoic acid and 2-(piperidin-1-yl)-2-(2-methylpyrimidin-5-yl)ethanamine LCMS (MH$^+$): m/z=393.2, $t_R$ (minutes, Method F)=1.68. $[\alpha]_D^{20}$=5.70 (c=4.21 mg/mL, CHCl$_3$).

Example 3i3

(−)2,3-dichloro-N-(2-(2-methylpyrimidin-5-yl)-2-(piperidin-1-yl)ethyl)benzamide

LCMS (MH$^+$): m/z=393.1, $t_R$ (minutes, Method F)=1.69. $[\alpha]_D^{20}$=−2.48 (c=4.56 mg/mL, CHCl$_3$).

Example 3j3

(+)2,3-dichloro-N-(2-(4,4-difluoropiperidin-1-yl)-2-(2-methylpyrimidin-5-yl)ethyl)benzamide

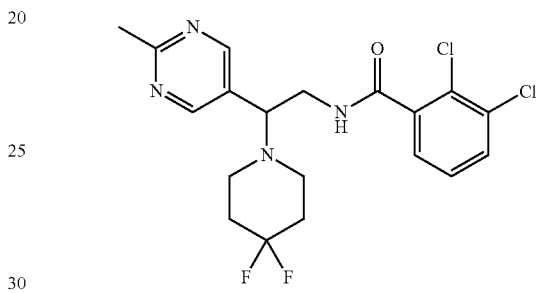

From 2,3-dichlorobenzoic acid and 2-(4,4-difluoropiperidin-1-yl)-2-(2-methylpyrimidin-5-yl)ethanamine LCMS (MH$^+$): m/z=429.1, $t_R$ (minutes, Method F)=2.19. $[\alpha]_D^{20}$=7.18 (c=4.32 mg/mL, CHCl$_3$).

Example 3k3

(−)2,3-dichloro-N-(2-(4,4-difluoropiperidin-1-yl)-2-(2-methylpyrimidin-5-yl)ethyl)benzamide LCMS (MH$^+$): m/z=429.1, $t_R$ (minutes, Method F)=2.20. $[\alpha]_D^{20}$=−8.18 (c=4.89 mg/mL, CHCl$_3$).

Example 3l3

(+)2,6-dichloro-N-(2-(4,4-difluoropiperidin-1-yl)-2-(2-methylpyrimidin-5-yl)ethyl)benzamide

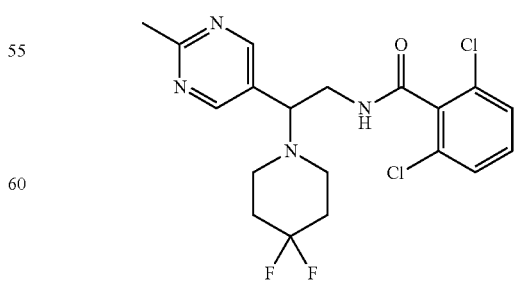

From 2,6-dichlorobenzoic acid and 2-(4,4-difluoropiperidin-1-yl)-2-(2-methylpyrimidin-5-yl)ethanamine LCMS (MH⁺): m/z=429.1, $t_R$ (minutes, Method F)=2.30. $[\alpha]_D^{20}$=10.73 (c=8.0 mg/mL, CHCl₃).

Example 3m3

(−)2,6-dichloro-N-(2-(4,4-difluoropiperidin-1-yl)-2-(2-methylpyrimidin-5-yl)ethyl)benzamide LCMS (MH⁺): m/z=429.1, $t_R$ (minutes, Method F)=2.31. $[\alpha]_D^{20}$=−7.1 (c=5.5 mg/mL, CHCl₃).

Example 3n3

(+)2,3-dichloro-5-fluoro-N-(2-(4,4-difluoropiperidin-1-yl)-2-(2-methylpyrimidin-5-yl)ethyl)benzamide

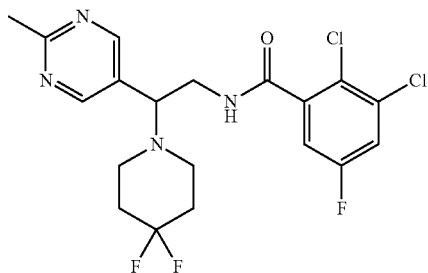 [SMILES: Cc1ncc(C(CNC(=O)c2cc(F)cc(Cl)c2Cl)N2CCC(F)(F)CC2)cn1]

From 2,3-dichloro-5-fluorobenzoic acid and 2-(4,4-difluoropiperidin-1-yl)-2-(2-methylpyrimidin-5-yl)ethanamine LCMS (MH⁺): m/z=447.1, $t_R$ (minutes, Method F)=2.54. $[\alpha]_D^{20}$=6.7 (c=3.2 mg/mL, CHCl₃).

Example 3o3

(−)2,3-dichloro-5-fluoro-N-(2-(4,4-difluoropiperidin-1-yl)-2-(2-methylpyrimidin-5-yl)ethyl)benzamide LCMS (MH⁺): m/z=447.1, $t_R$ (minutes, Method F)=2.53. $[\alpha]_D^{20}$=−5.5 (c=3.4 mg/mL, CHCl₃).

Example 3p3

(+)2,6-dichloro-5-fluoro-N-(2-(4,4-difluoropiperidin-1-yl)-2-(2-methylpyrimidin-5-yl)ethyl)benzamide

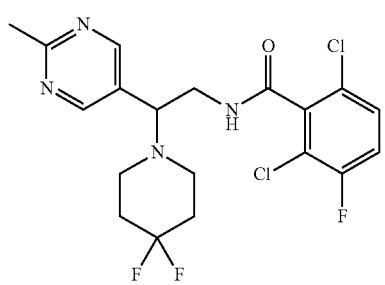 [SMILES: Cc1ncc(C(CNC(=O)c2c(Cl)ccc(F)c2Cl)N2CCC(F)(F)CC2)cn1]

From 2,6-dichloro-5-fluorobenzoic acid and 2-(4,4-difluoropiperidin-1-yl)-2-(2-methylpyrimidin-5-yl)ethanamine LCMS (MH⁺): m/z=447.0, $t_R$ (minutes, Method F)=2.18. $[\alpha]_D^{20}$=5.63 (c=3.2 mg/mL, CHCl₃).

Example 3q3

(−)2,6-dichloro-5-fluoro-N-(2-(4,4-difluoropiperidin-1-yl)-2-(2-methylpyrimidin-5-yl)ethyl)benzamide LCMS (MH⁺): m/z=447.0, $t_R$ (minutes, Method F)=2.17. $[\alpha]_D^{20}$=−3.96 (c=3.2 mg/mL, CHCl₃).

Example 3r3

(+)2-chloro-3-methoxy-N-(2-(4,4-difluoropiperidin-1-yl)-2-(2-methylpyrimidin-5-yl)ethyl)benzamide

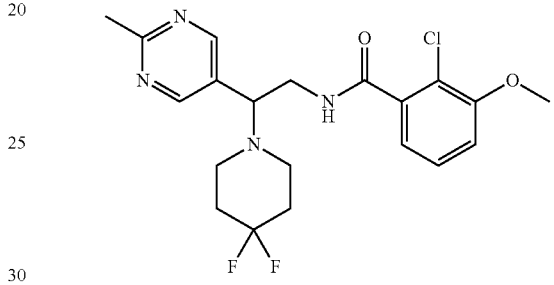

From 2-chloro-3-methoxybenzoic acid and 2-(4,4-difluoropiperidin-1-yl)-2-(2-methylpyrimidin-5-yl)ethanamine LCMS (MH⁺): m/z=425.1, $t_R$ (minutes, Method F)=1.99. $[\alpha]_D^{20}$=8.56 (c=4.4 mg/mL, CHCl₃).

Example 3s3

(−)2-chloro-3-methoxy-N-(2-(4,4-difluoropiperidin-1-yl)-2-(2-methylpyrimidin-5-yl)ethyl)benzamide LCMS (MH⁺): m/z=425.1, $t_R$ (minutes, Method F)=1.83. $[\alpha]_D^{20}$=−7.8 (c=4.4 mg/mL, CHCl₃).

Example 3t3

(+)2-chloro-3-(difluoromethoxy)-N-(2-(4,4-difluoropiperidin-1-yl)-2-(2-methylpyrimidin-5-yl)ethyl)benzamide

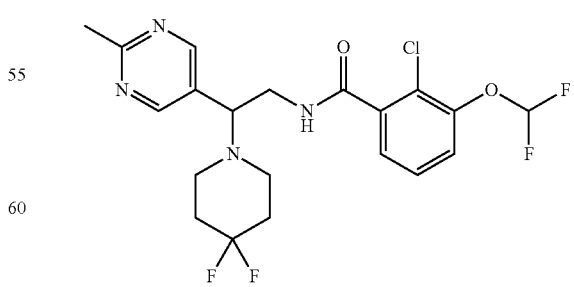

From 2-chloro-3-(difluoromethoxy)benzoic acid and 2-(4,4-difluoropiperidin-1-yl)-2-(2-methylpyrimidin-5-yl)ethanamine LCMS (MH+): m/z=461.2, $t_R$ (minutes, Method F)=2.44. $[\alpha]_D^{20}$=25.19 (c=2.62 mg/mL, CHCl$_3$).

Example 3u3

(−)2-chloro-3-(difluoromethoxy)-N-(2-(4,4-difluoropiperidin-1-yl)-2-(2-methylpyrimidin-5-yl)ethyl)benzamide LCMS (MH+): m/z=461.1, $t_R$ (minutes, Method F)=2.44. $[\alpha]_D^{20}$=−23.23 (c=1.65 mg/mL, CHCl$_3$).

Example 3v3

(+)2,3-dichloro-N-(2-(2-(difluoromethyl)pyrimidin-5-yl)-2-morpholinoethyl)benzamide

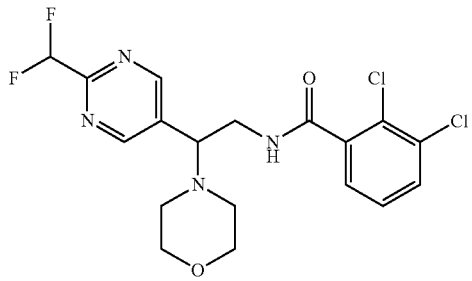 [SMILES: O=C(NCC(c1cnc(C(F)F)nc1)N1CCOCC1)c1cccc(Cl)c1Cl]

From 2,3-dichlorobenzoic acid and 2-(2-(difluoromethyl)pyrimidin-5-yl)-2-morpholinoethanamine
LCMS (MH+): m/z=431.1, $t_R$ (minutes, Method F)=2.36. $[\alpha]_D^{20}$=14.88 (c=2.71 mg/mL, CHCl$_3$).

Example 3x3

(−)2,3-dichloro-N-(2-(2-(difluoromethyl)pyrimidin-5-yl)-2-morpholinoethyl)benzamide LCMS (MH+): m/z=431.1, $t_R$ (minutes, Method F)=2.37. $[\alpha]_D^{20}$=−11.93 (c=2.85 mg/mL, CHCl$_3$).

Example 3y3

(+)2-chloro-N-(2-(2-(difluoromethyl)pyrimidin-5-yl)-2-morpholinoethyl)benzamide

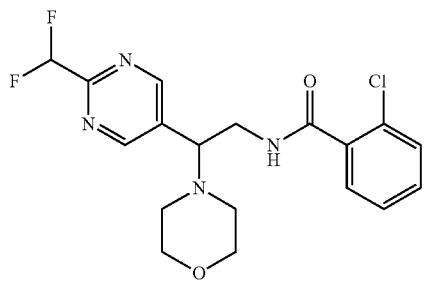 [SMILES: O=C(NCC(c1cnc(C(F)F)nc1)N1CCOCC1)c1ccccc1Cl]

From 2-chlorobenzoic acid and 2-(2-(difluoromethyl)pyrimidin-5-yl)-2-morpholinoethanamine LCMS (MH+): m/z=397.1, $t_R$ (minutes, Method F)=1.90. $[\alpha]_D^{20}$=12.72 (c=1.73 mg/mL, CHCl$_3$).

Example 3z3

(−)2-chloro-N-(2-(2-(difluoromethyl)pyrimidin-5-yl)-2-morpholinoethyl)benzamide

LCMS (MH+): m/z=397.1, $t_R$ (minutes, Method F)=1.90. $[\alpha]_D^{20}$=−11.70 (c=1.68 mg/mL, CHCl$_3$).

Example 3a4

(+)2-chloro-3-fluoro-N-(2-(2-(difluoromethyl)pyrimidin-5-yl)-2-morpholinoethyl)benzamide

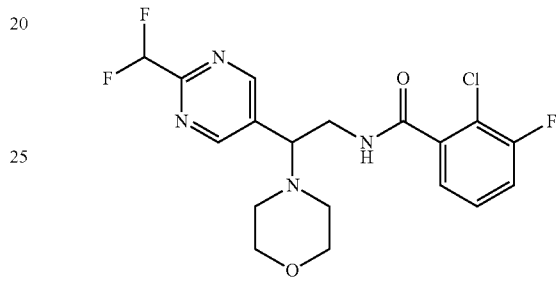

From 2-chloro-3-fluorobenzoic acid and 2-(2-(difluoromethyl)pyrimidin-5-yl)-2-morpholinoethanamine
LCMS (MH+): m/z=415.1, $t_R$ (minutes, Method F)=2.24. $[\alpha]_D^{20}$=16.38 (c=3.54 mg/mL, CHCl$_3$).

Example 3b4

(−)2-chloro-3-fluoro-N-(2-(2-(difluoromethyl)pyrimidin-5-yl)-2-morpholinoethyl)benzamide LCMS (MH+): m/z=415.1, $t_R$ (minutes, Method F)=2.23. $[\alpha]_D^{20}$=−13.82 (c=4.56 mg/mL, CHCl$_3$).

Example 3c4

(+)2-chloro-N-(2-(2-cyclopropylpyrimidin-5-yl)-2-(4,4-difluoropiperidin-1-yl)ethyl)benzamide

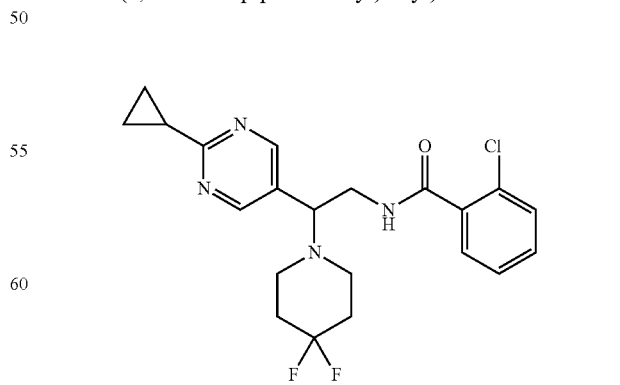

From 2-chlorobenzoic acid and 2-(2-cyclopropylpyrimidin-5-yl)-2-(4,4-difluoropiperidin-1-yl)ethanamine LCMS (MH⁺): m/z=421.2, t$_R$ (minutes, Method F)=2.36. [α]$_D^{20}$=26.88 (c=6.2 mg/mL, CHCl₃).

Example 3d4

(−)2-chloro-N-(2-(2-cyclopropylpyrimidin-5-yl)-2-(4,4-difluoropiperidin-1-yl)ethyl)benzamide LCMS (MH⁺): m/z=421.2, t$_R$ (minutes, Method F)=2.35. [α]$_D^{20}$=−28.02 (c=4.7 mg/mL, CHCl₃).

Example 3e4

(+)2,3-dichloro-N-(2-(2-cyclopropylpyrimidin-5-yl)-2-(4,4-difluoropiperidin-1-yl)ethyl)benzamide

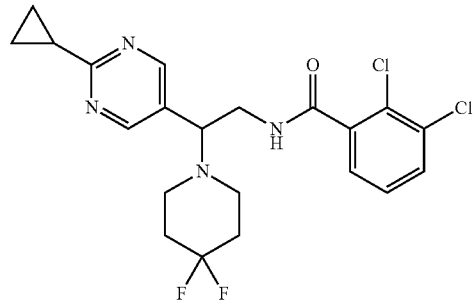 [SMILES: O=C(NCC(c1cnc(C2CC2)nc1)N1CCC(F)(F)CC1)c1cccc(Cl)c1Cl]

From 2,3-dichlorobenzoic acid and 2-(2-cyclopropylpyrimidin-5-yl)-2-(4,4-difluoropiperidin-1-yl)ethanamine
LCMS (MH⁺): m/z=455.1, t$_R$ (minutes, Method F)=2.41. [α]$_D^{20}$=27.06 (c=11.0 mg/mL, CHCl₃).

Example 3f4

(−)2,3-dichloro-N-(2-(2-cyclopropylpyrimidin-5-yl)-2-(4,4-difluoropiperidin-1-yl)ethyl)benzamide LCMS (MH⁺): m/z=455.1, t$_R$ (minutes, Method F)=2.42. [α]$_D^{20}$=−28.03 (c=10.0 mg/mL, CHCl₃).

Example 3g4

(+)2,6-dichloro-N-(2-(2-cyclopropylpyrimidin-5-yl)-2-(4,4-difluoropiperidin-1-yl)ethyl)benzamide

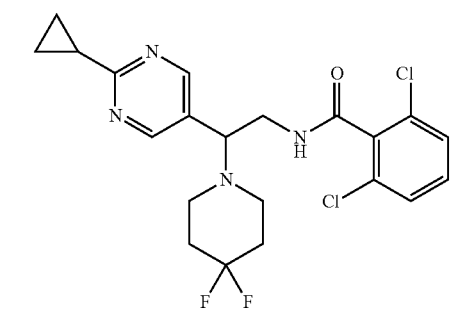 [SMILES: O=C(NCC(c1cnc(C2CC2)nc1)N1CCC(F)(F)CC1)c1c(Cl)cccc1Cl]

From 2,6-dichlorobenzoic acid and 2-(2-cyclopropylpyrimidin-5-yl)-2-(4,4-difluoropiperidin-1-yl)ethanamine LCMS (MH⁺): m/z=455.0, t$_R$ (minutes, Method F)=2.31. [α]$_D^{20}$=25.50 (c=6.6 mg/mL, CHCl₃).

Example 3h4

(−)2,6-dichloro-N-(2-(2-cyclopropylpyrimidin-5-yl)-2-(4,4-difluoropiperidin-1-yl)ethyl)benzamide LCMS (MH⁺): m/z=455.1, t$_R$ (minutes, Method F)=2.30. [α]$_D^{20}$=−27.65 (c=5.8 mg/mL, CHCl₃).

Example 3i4

(+)2-chloro-6-fluoro-N-(2-(2-cyclopropylpyrimidin-5-yl)-2-(4,4-difluoropiperidin-1-yl)ethyl)benzamide

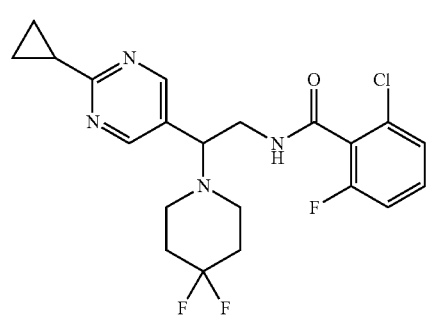 [SMILES: O=C(NCC(c1cnc(C2CC2)nc1)N1CCC(F)(F)CC1)c1c(F)cccc1Cl]

From 2-chloro-6-fluorobenzoic acid and 2-(2-cyclopropylpyrimidin-5-yl)-2-(4,4-difluoropiperidin-1-yl)ethanamine
LCMS (MH⁺): m/z=439.2, t$_R$ (minutes, Method F)=2.40. [α]$_D^{20}$=27.66 (c=7.1 mg/mL, CHCl₃).

Example 3j4

(−)2-chloro-6-fluoro-N-(2-(2-cyclopropylpyrimidin-5-yl)-2-(4,4-difluoropiperidin-1-yl)ethyl)benzamide LCMS (MH⁺): m/z=439.1, t$_R$ (minutes, Method F)=2.40. [α]$_D^{20}$=−26.27 (c=7.0 mg/mL, CHCl₃).

Example 3k4

(+)2-chloro-N-(2-(4,4-difluoropiperidin-1-yl)-2-(2-ethylpyrimidin-5-yl)ethyl)benzamide

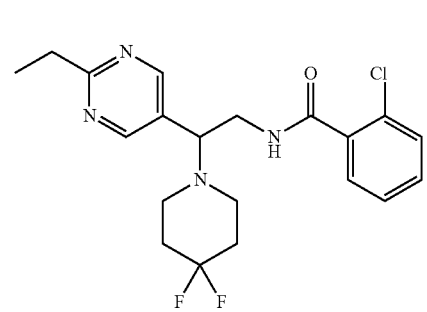 [SMILES: CCc1ncc(C(CNC(=O)c2ccccc2Cl)N2CCC(F)(F)CC2)cn1]

From 2-chlorobenzoic acid and 2-(4,4-difluoropiperidin-1-yl)-2-(2-ethylpyrimidin-5-yl)ethanamine LCMS (MH+): m/z=409.2, $t_R$ (minutes, Method F)=2.34. $[\alpha]_D^{20}$=20.94 (c=7.21 mg/mL, CHCl$_3$).

Example 314

(−)2-chloro-N-(2-(4,4-difluoropiperidin-1-yl)-2-(2-ethylpyrimidin-5-yl)ethyl)benzamide LCMS (MH+): m/z=409.2, $t_R$ (minutes, Method F)=2.34. $[\alpha]_D^{20}$=−19.15 (c=7.99 mg/mL, CHCl$_3$).

Example 3m4

(+)2,3-dichloro-N-(2-(4,4-difluoropiperidin-1-yl)-2-(2-ethylpyrimidin-5-yl)ethyl)benzamide

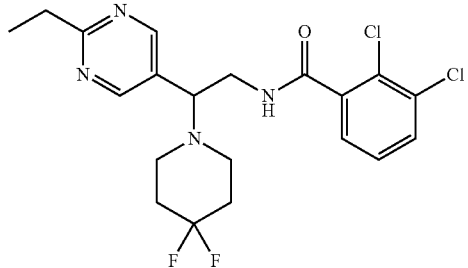 [SMILES: CCc1ncc(C(CNC(=O)c2cccc(Cl)c2Cl)N2CCC(F)(F)CC2)cn1]

From 2,3-dichlorobenzoic acid and 2-(4,4-difluoropiperidin-1-yl)-2-(2-ethylpyrimidin-5-yl)ethanamine
LCMS (MH+): m/z=443.1, $t_R$ (minutes, Method F)=2.56. $[\alpha]_D^{20}$=23.67 (c=7.73 mg/mL, CHCl$_3$).

Example 3n4

(−)2,3-dichloro-N-(2-(4,4-difluoropiperidin-1-yl)-2-(2-ethylpyrimidin-5-yl)ethyl)benzamide LCMS (MH+): m/z=443.1, $t_R$ (minutes, Method F)=2.55. $[\alpha]_D^{20}$=−23.24 (c=7.4 mg/mL, CHCl$_3$).

Example 3o4

(+)2,6-dichloro-N-(2-(4,4-difluoropiperidin-1-yl)-2-(2-ethylpyrimidin-5-yl)ethyl)benzamide

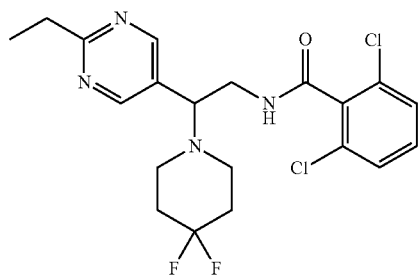 [SMILES: CCc1ncc(C(CNC(=O)c2c(Cl)cccc2Cl)N2CCC(F)(F)CC2)cn1]

From 2,6-dichlorobenzoic acid and 2-(4,4-difluoropiperidin-1-yl)-2-(2-ethylpyrimidin-5-yl)ethanamine
LCMS (MH+): m/z=443.1, $t_R$ (minutes, Method F)=2.44. $[\alpha]_D^{20}$=17.52 (c=6.45 mg/mL, CHCl$_3$).

Example 3p4

(−)2,6-dichloro-N-(2-(4,4-difluoropiperidin-1-yl)-2-(2-ethylpyrimidin-5-yl)ethyl)benzamide LCMS (MH+): m/z=443.1, $t_R$ (minutes, Method F)=2.44. $[\alpha]_D^{20}$=−18.95 (c=6.28 mg/mL, CHCl$_3$).

Example 3q4

(+)2-chloro-6-fluoro-N-(2-(4,4-difluoropiperidin-1-yl)-2-(2-ethylpyrimidin-5-yl)ethyl)benzamide

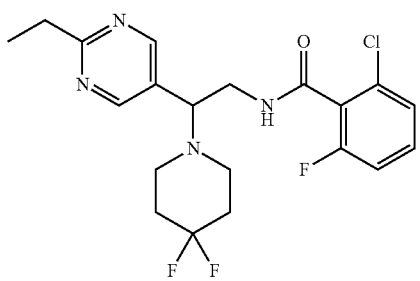 [SMILES: CCc1ncc(C(CNC(=O)c2c(F)cccc2Cl)N2CCC(F)(F)CC2)cn1]

From 2-chloro-6-fluorobenzoic acid and 2-(4,4-difluoropiperidin-1-yl)-2-(2-ethylpyrimidin-5-yl)ethanamine
LCMS (MH+): m/z=427.2, $t_R$ (minutes, Method F)=2.37. $[\alpha]_D^{20}$=21.82 (c=7.15 mg/mL, CHCl$_3$).

Example 3r4

(−)2-chloro-6-fluoro-N-(2-(4,4-difluoropiperidin-1-yl)-2-(2-ethylpyrimidin-5-yl)ethyl)benzamide LCMS (MH+): m/z=427.2, $t_R$ (minutes, Method F)=2.38. $[\alpha]_D^{20}$=−21.79 (c=7.02 mg/mL, CHCl$_3$).

Example 3s4

(+)2,4-dichloro-N-(2-(4,4-difluoropiperidin-1-yl)-2-(2-(trifluoromethyl)pyrimidin-5-yl)ethyl)benzamide

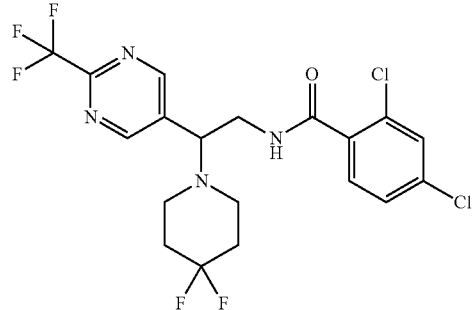 [SMILES: O=C(NCC(c1cnc(C(F)(F)F)nc1)N1CCC(F)(F)CC1)c1ccc(Cl)cc1Cl]

From 2,4-dichlorobenzoic acid and 2-(4,4-difluoropiperidin-1-yl)-2-(2-(trifluoromethyl)pyrimidin-5-yl)ethanamine
LCMS (MH+): m/z=483.1, $t_R$ (minutes, Method F)=2.95. $[\alpha]_D^{20}$=11.6 (c=3.7 mg/mL, CHCl$_3$).

Example 3t4

(−)2,4-dichloro-N-(2-(4,4-difluoropiperidin-1-yl)-2-(2-(trifluoromethyl)pyrimidin-5-yl)ethyl)benzamide LCMS (MH$^+$): m/z=483.1, t$_R$ (minutes, Method F)=2.95. [α]$_D^{20}$=−14.4 (c=4.0 mg/mL, CHCl$_3$).

Example 3u4

(+)2-chloro-1-methoxy-N-(2-(4,4-difluoropiperidin-1-yl)-2-(2-(trifluoromethyl)pyrimidin-5-yl)ethyl)benzamide

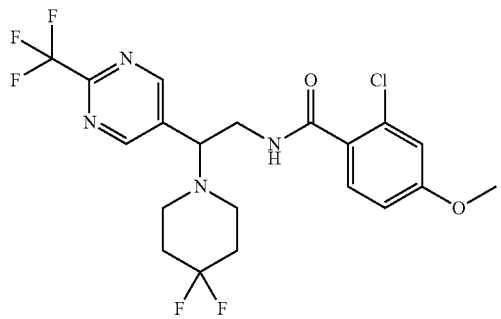 [SMILES: COc1ccc(C(=O)NCC(c2cnc(C(F)(F)F)nc2)N2CCC(F)(F)CC2)c(Cl)c1]

From 2-chloro-4-methoxybenzoic acid and 2-(4,4-difluoropiperidin-1-yl)-2-(2-(trifluoromethyl)pyrimidin-5-yl)ethanamine LCMS (MH$^+$): m/z=479.2, t$_R$ (minutes, Method F)=3.03. [α]$_D^{20}$=11.1 (c=3.0 mg/mL, CHCl$_3$).

Example 3v4

(−)2-chloro-4-methoxy-N-(2-(4,4-difluoropiperidin-1-yl)-2-(2-(trifluoromethyl)pyrimidin-5-yl)ethyl)benzamide LCMS (MH$^+$): m/z=479.1, t$_R$ (minutes, Method F)=3.04. [α]$_D^{20}$=−13.6 (c=3.0 mg/mL, CHCl$_3$).

Example 3x4

(+)2,4-dichloro-6-fluoro-N-(2-(4,4-difluoropiperidin-1-yl)-2-(2-(trifluoromethyl)pyrimidin-5-yl)ethyl)benzamide From 2,4-dichloro-6-fluorobenzoic acid and 2-(4,4-difluoropiperidin-1-yl)-2-(2-(trifluoromethyl)pyrimidin-5-yl)ethanamine LCMS (MH$^+$): m/z=501.0, t$_R$ (minutes, Method F)=3.01. [α]$_D^{20}$=22.8 (c=3.2 mg/mL, CHCl$_3$).

Example 3y4

(−)2,4-dichloro-6-fluoro-N-(2-(4,4-difluoropiperidin-1-yl)-2-(2-(trifluoromethyl)pyrimidin-5-yl)ethyl)benzamide LCMS (MH$^+$): m/z=501.0, t$_R$ (minutes, Method F)=3.01. [α]$_D^{20}$=−23.4 (c=3.0 mg/mL, CHCl$_3$).

Example 3z4

(+)2-chloro-3,4-dimethoxy-N-(2-(4,4-difluoropiperidin-1-yl)-2-(2-(trifluoromethyl)pyrimidin-5-yl)ethyl)benzamide

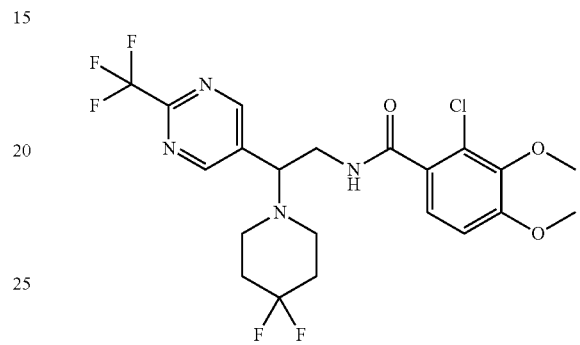

From 2-chloro-3,4-dimethoxybenzoic acid and 2-(4,4-difluoropiperidin-1-yl)-2-(2-(trifluoromethyl)pyrimidin-5-yl)ethanamine LCMS (MH$^+$): m/z=509.1, t$_R$ (minutes, Method F)=2.77. [α]$_D^{20}$=23.3 (c=3.6 mg/mL, CHCl$_3$).

Example 3a5

(−)2-chloro-3,4-dimethoxy-N-(2-(4,4-difluoropiperidin-1-yl)-2-(2-(trifluoromethyl)pyrimidin-5-yl)ethyl)benzamide LCMS (MH$^+$): m/z=509.1, t$_R$ (minutes, Method F)=2.78. [α]$_D^{20}$=−19.2 (c=3.5 mg/mL, CHCl$_3$).

Example 3b5

(+)2,6-dichloro-4-fluoro-N-(2-(4,4-difluoropiperidin-1-yl)-2-(2-(trifluoromethyl)pyrimidin-5-yl)ethyl)benzamide

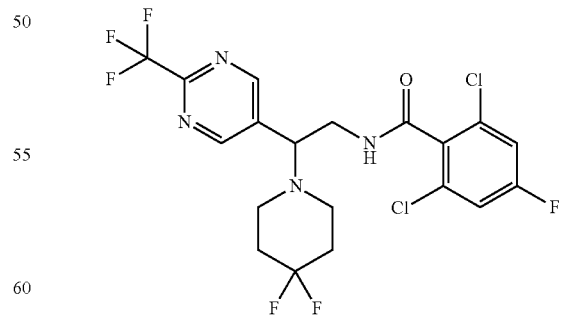

From 2,6-dichloro-4-fluorobenzoic acid and 2-(4,4-difluoropiperidin-1-yl)-2-(2-(trifluoromethyl)pyrimidin-5-yl)ethanamine LCMS (MH$^+$): m/z=501.1, t$_R$ (minutes, Method F)=3.17. [α]$_D^{20}$=19.64 (c=2.24 mg/mL, CHCl$_3$).

Example 3c5

(−)2,6-dichloro-4-fluoro-N-(2-(4,4-difluoropiperidin-1-yl)-2-(2-(trifluoromethyl)pyrimidin-5-yl)ethyl)benzamide LCMS (MH$^+$): m/z=501.1, t$_R$ (minutes, Method F)=3.17. [α]$_D^{20}$=−19.73 (c=2.23 mg/mL, CHCl$_3$).

Example 3d5

(+)2-chloro-4,6-difluoro-N-(2-(4,4-difluoropiperidin-1-yl)-2-(2-(trifluoromethyl)pyrimidin-5-yl)ethyl)benzamide

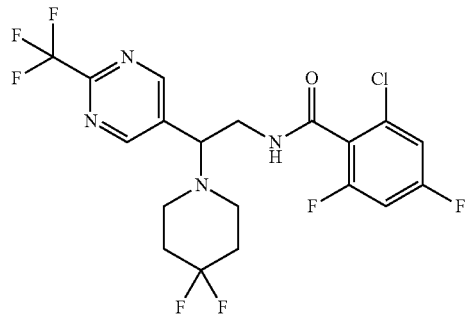 [SMILES: O=C(NCC(c1cnc(C(F)(F)F)nc1)N1CCC(F)(F)CC1)c1c(F)cc(F)cc1Cl]

From 2-chloro-4,6-difluorobenzoic acid and 2-(4,4-difluoropiperidin-1-yl)-2-(2-(trifluoromethyl)pyrimidin-5-yl)ethanamine
LCMS (MH$^+$): m/z=485.1, t$_R$ (minutes, Method F)=3.12. [α]$_D^{20}$=14.40 (c=2.43 mg/mL, CHCl$_3$).

Example 3e5

(−)2-chloro-4,6-difluoro-N-(2-(4,4-difluoropiperidin-1-yl)-2-(2-(trifluoromethyl)pyrimidin-5-yl)ethyl)benzamide LCMS (MH$^+$): m/z=485.1, t$_R$ (minutes, Method F)=3.12. [α]$_D^{20}$=−12.21 (c=2.13 mg/mL, CHCl$_3$).

Example 3f5

(+)2-chloro-N-(2-(4,4-difluoropiperidin-1-yl)-2-(2-(trifluoromethyl)pyrimidin-5-yl)ethyl)-6-fluoro-3-methoxybenzamide

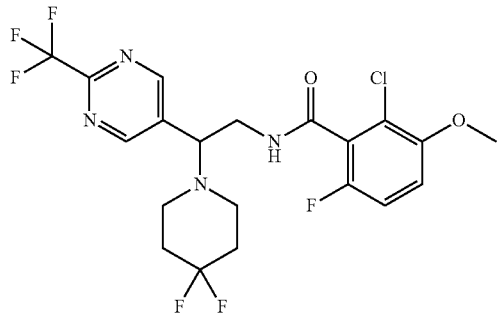 [SMILES: COc1ccc(F)c(C(=O)NCC(c2cnc(C(F)(F)F)nc2)N2CCC(F)(F)CC2)c1Cl]

From 2-chloro-3-methoxy-6-fluorobenzoic acid and 2-(4,4-difluoropiperidin-1-yl)-2-(2-(trifluoromethyl)pyrimidin-5-yl)ethanamine
LCMS (MH$^+$): m/z=497.1, t$_R$ (minutes, Method F)=3.05. [α]$_D^{20}$=18.30 (c=4.48 mg/mL, CHCl$_3$).

Example 3g5

(−)2-chloro-N-(2-(4,4-difluoropiperidin-1-yl)-2-(2-(trifluoromethyl)pyrimidin-5-yl)ethyl)-6-fluoro-3-methoxybenzamide LCMS (MH$^+$): m/z=497.1, t$_R$ (minutes, Method F)=3.05. [α]$_D^{20}$=−16.07 (c=4.48 mg/mL, CHCl$_3$).

Example 3h5

(+)2-chloro-N-(2-(4,4-difluoropiperidin-1-yl)-2-(2-methylpyrimidin-5-yl)ethyl)-3-(trifluoromethoxy)benzamide

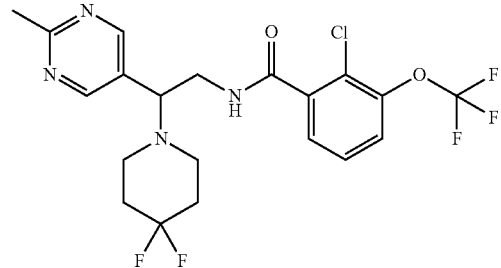 [SMILES: Cc1ncc(C(CNC(=O)c2cccc(OC(F)(F)F)c2Cl)N2CCC(F)(F)CC2)cn1]

From 2-chloro-3-(trifluoromethoxy)benzoic acid and 2-(4,4-difluoropiperidin-1-yl)-2-(2-methylpyrimidin-5-yl)ethanamine
LCMS (MH$^+$): m/z=479.1, t$_R$ (minutes, Method F)=2.63. [α]$_D^{20}$=16.0 (c=6.0 mg/mL, CHCl$_3$).

Example 3i5

(−)2-chloro-N-(2-(4,4-difluoropiperidin-1-yl)-2-(2-methylpyrimidin-5-yl)ethyl)-3-(trifluoromethoxy)benzamide LCMS (MH$^+$): m/z=479.1, t$_R$ (minutes, Method F)=2.63. [α]$_D^{20}$=−13.3 (c=4.9 mg/mL, CHCl$_3$).

Example 3j5

(+)2-chloro-N-(2-(2-(difluoromethyl)pyridin-5-yl)-2-(4,4-difluoropiperidin-1-yl)ethyl)benzamide

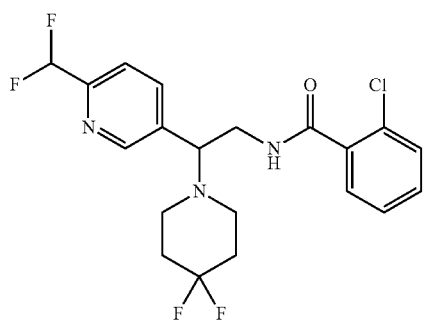 [SMILES: O=C(NCC(c1ccc(C(F)F)nc1)N1CCC(F)(F)CC1)c1ccccc1Cl]

From 2-chlorobenzoic acid and 2-(4,4-difluoropiperidin-1-yl)-2-(2-(difluoromethyl)pyridin-5-yl)ethanamine
LCMS (MH$^+$): m/z=430.1, t$_R$ (minutes, Method F)=2.45. [α]$_D^{20}$=4.10 (c=1.95 mg/mL, CHCl$_3$).

Example 3k5

(−)2-chloro-N-(2-(2-(difluoromethyl)pyridin-5-yl)-2-(4,4-difluoropiperidin-1-yl)ethyl)benzamide LCMS (MH$^+$): m/z=430.1, $t_R$ (minutes, Method F)=2.45. $[\alpha]_D^{20}$=−6.06 (c=1.98 mg/mL, CHCl$_3$).

Example 3l5

(+)2,3-dichloro-N-(2-(2-(difluoromethyl)pyridin-5-yl)-2-(4,4-difluoropiperidin-1-yl)ethyl)benzamide

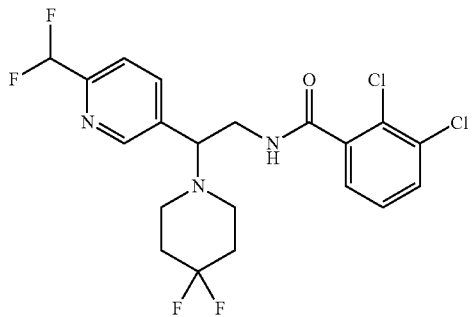

From 2,3-dichlorobenzoic acid and 2-(4,4-difluoropiperidin-1-yl)-2-(2-(difluoromethyl)pyridin-5-yl)ethanamine LCMS (MH$^+$): m/z=464.1, $t_R$ (minutes, Method F)=2.65. $[\alpha]_D^{20}$=3.06 (c=3.27 mg/mL, CHCl$_3$).

Example 3m5

(−)2,3-dichloro-N-(2-(2-(difluoromethyl)pyridin-5-yl)-2-(4,4-difluoropiperidin-1-yl)ethyl)benzamide LCMS (MH$^+$): m/z=464.1, $t_R$ (minutes, Method F)=2.65. $[\alpha]_D^{20}$=−4.71 (c=2.76 mg/mL, CHCl$_3$).

Example 3n5

(+)2,6-dichloro-N-(2-(2-(difluoromethyl)pyridin-5-yl)-2-(4,4-difluoropiperidin-1-yl)ethyl)benzamide

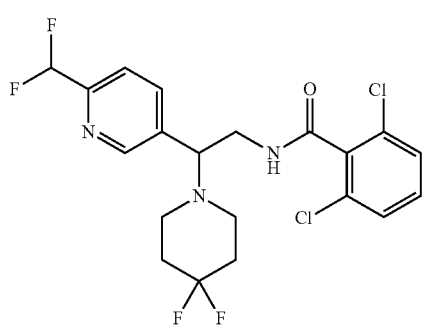

From 2,6-dichlorobenzoic acid and 2-(4,4-difluoropiperidin-1-yl)-2-(2-(difluoromethyl)pyridin-5-yl)ethanamine LCMS (MH$^+$): m/z=464.1, $t_R$ (minutes, Method F)=2.57. $[\alpha]_D^{20}$=12.02 (c=2.08 mg/mL, CHCl$_3$).

Example 3o5

(−)2,6-dichloro-N-(2-(2-(difluoromethyl)pyridin-5-yl)-2-(4,4-difluoropiperidin-1-yl)ethyl)benzamide LCMS (MH$^+$): m/z=464.1, $t_R$ (minutes, Method F)=2.57. $[\alpha]_D^{20}$=−11.47 (c=2.18 mg/mL, CHCl$_3$).

Example 3p5

(+)2,4-dichloro-N-(2-(2-(difluoromethyl)pyridin-5-yl)-2-(4,4-difluoropiperidin-1-yl)ethyl)benzamide

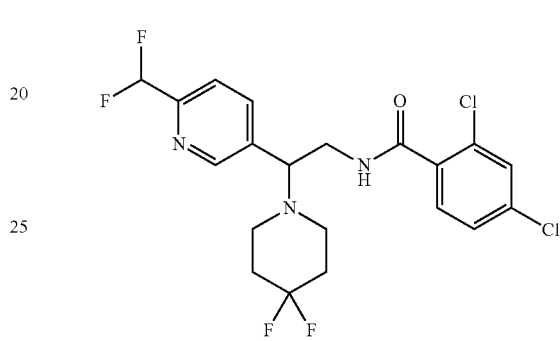

From 2,4-dichlorobenzoic acid and 2-(4,4-difluoropiperidin-1-yl)-2-(2-(difluoromethyl)pyridin-5-yl)ethanamine LCMS (MH$^+$): m/z=464.1, $t_R$ (minutes, Method F)=2.69. $[\alpha]_D^{20}$=11.56 (c=1.47 mg/mL, CHCl$_3$).

Example 3q5

(−)2,4-dichloro-N-(2-(2-(difluoromethyl)pyridin-5-yl)-2-(4,4-difluoropiperidin-1-yl)ethyl)benzamide LCMS (MH$^+$): m/z=464.1, $t_R$ (minutes, Method F)=2.70. $[\alpha]_D^{20}$=−11.90 (c=2.52 mg/mL, CHCl$_3$).

Example 3r5

(+)2-chloro-3-methoxy-N-(2-(2-(difluoromethyl)pyridin-5-yl)-2-(4,4-difluoropiperidin-1-yl)ethyl)benzamide

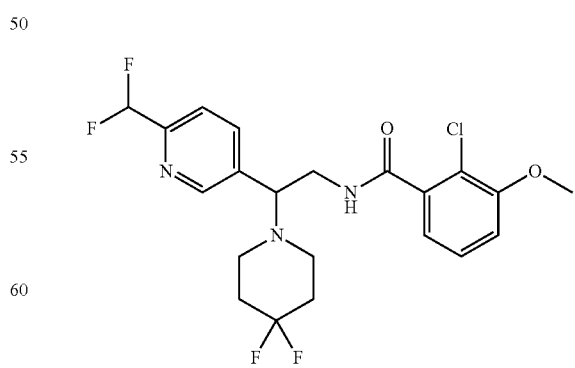

From 2-chloro-3-methoxybenzoic acid and 2-(4,4-difluoropiperidin-1-yl)-2-(2-(difluoromethyl)pyridin-5-yl)ethanamine LCMS (MH⁺): m/z=460.1, $t_R$ (minutes, Method F)=2.45. [α]$_D^{20}$=4.07 (c=2.95 mg/mL, CHCl₃).

Example 3s5

(−)2-chloro-3-methoxy-N-(2-(2-(difluoromethyl)pyridin-5-yl)-2-(4,4-difluoropiperidin-1-yl)ethyl)benzamide LCMS (MH⁺): m/z=460.1, $t_R$ (minutes, Method F)=2.45. [α]$_D^{20}$=−5.07 (c=2.96 mg/mL, CHCl₃).

Example 3t5

(+)2-chloro-3-fluoro-N-(2-(2-(difluoromethyl)pyridin-5-yl)-2-(4,4-difluoropiperidin-1-yl)ethyl)benzamide

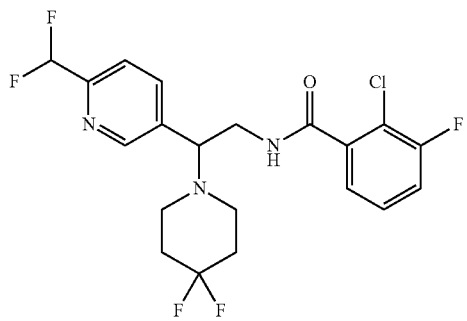 [SMILES: O=C(NCC(c1ccc(C(F)F)nc1)N1CCC(F)(F)CC1)c1cccc(F)c1Cl]

From 2-chloro-3-fluorobenzoic acid and 2-(4,4-difluoropiperidin-1-yl)-2-(2-(difluoromethyl)pyridin-5-yl)ethanamine LCMS (MH⁺): m/z=448.1, $t_R$ (minutes, Method F)=2.54. [α]$_D^{20}$=10.75 (c=1.86 mg/mL, CHCl₃).

Example 3u5

(−)2-chloro-3-fluoro-N-(2-(2-(difluoromethyl)pyridin-5-yl)-2-(4,4-difluoropiperidin-1-yl)ethyl)benzamide LCMS (MH⁺): m/z=448.1, $t_R$ (minutes, Method F)=2.54. [α]$_D^{20}$=−13.72 (c=2.55 mg/mL, CHCl₃).

Example 3v5

(+)2-chloro-N-(2-(2-(difluoromethyl)pyrimidin-5-yl)-2-(4,4-difluoropiperidin-1-yl)ethyl)benzamide

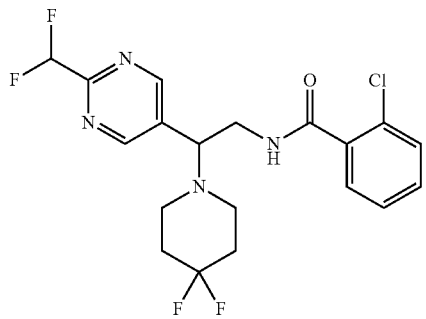 [SMILES: O=C(NCC(c1cnc(C(F)F)nc1)N1CCC(F)(F)CC1)c1ccccc1Cl]

From 2-chlorobenzoic acid and 2-(4,4-difluoropiperidin-1-yl)-2-(2-(difluoromethyl)pyrimidin-5-yl)ethanamine LCMS (MH⁺): m/z=431.1, $t_R$ (minutes, Method F)=2.53. [α]$_D^{20}$=17.6 (c=3.5 mg/mL, CHCl₃).

Example 3x5

(−)2-chloro-N-(2-(2-(difluoromethyl)pyrimidin-5-yl)-2-(4,4-difluoropiperidin-1-yl)ethyl)benzamide LCMS (MH⁺): m/z=431.1, $t_R$ (minutes, Method I)=2.23. [α]$_D^{20}$=−17.0 (c=3.7 mg/mL, CHCl₃).

Example 3y5

(+)2,3-dichloro-N-(2-(2-(difluoromethyl)pyrimidin-5-yl)-2-(4,4-difluoropiperidin-1-yl)ethyl)benzamide

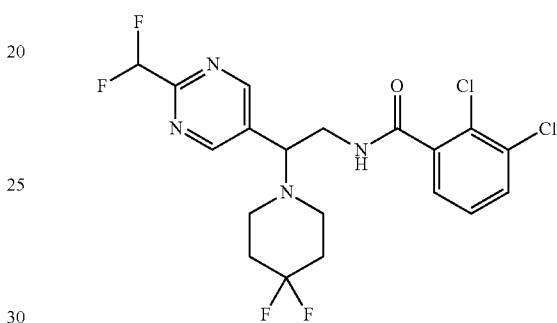

From 2,3-dichlorobenzoic acid and 2-(4,4-difluoropiperidin-1-yl)-2-(2-(difluoromethyl)pyrimidin-5-yl)ethanamine LCMS (MH⁺): m/z=465.1, $t_R$ (minutes, Method F)=2.74. [α]$_D^{20}$=17.7 (c=3.7 mg/mL, CHCl₃).

Example 3z5

(−)2,3-dichloro-N-(2-(2-(difluoromethyl)pyrimidin-5-yl)-2-(4,4-difluoropiperidin-1-yl)ethyl)benzamide LCMS (MH⁺): m/z=465.1, $t_R$ (minutes, Method F)=2.74. [α]$_D^{20}$=−17.9 (c=4.5 mg/mL, CHCl₃).

Example 3a6

(+)2,6-dichloro-N-(2-(2-(difluoromethyl)pyrimidin-5-yl)-2-(4,4-difluoropiperidin-1-yl)ethyl)benzamide

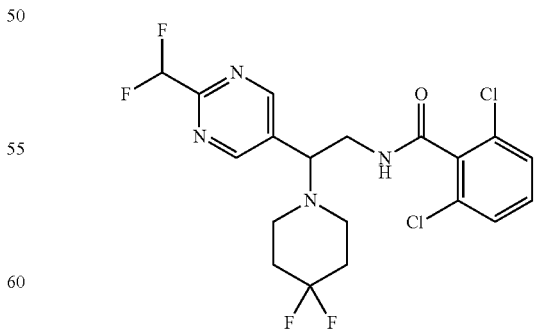

From 2,6-dichlorobenzoic acid and 2-(4,4-difluoropiperidin-1-yl)-2-(2-(difluoromethyl)pyrimidin-5-yl)ethanamine LCMS (MH⁺): m/z=465.1, $t_R$ (minutes, Method I)=2.36. [α]$_D^{20}$=19.5 (c=3.6 mg/mL, CHCl₃).

Example 3b6

(−)2,6-dichloro-N-(2-(2-(difluoromethyl)pyrimidin-5-yl)-2-(4,4-difluoropiperidin-1-yl)ethyl)benzamide LCMS (MH⁺): m/z=465.1, $t_R$ (minutes, Method I)=2.36. $[\alpha]_D^{20}$=−18.3 (c=3.8 mg/mL, CHCl$_3$).

Example 3c6

(+)2,4-dichloro-N-(2-(2-(difluoromethyl)pyrimidin-5-yl)-2-(4,4-difluoropiperidin-1-yl)ethyl)benzamide

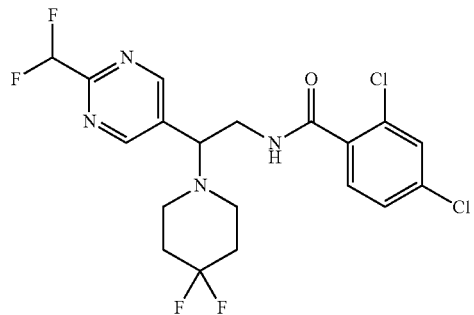 [SMILES: O=C(NCC(c1cnc(C(F)F)nc1)N1CCC(F)(F)CC1)c1ccc(Cl)cc1Cl]

From 2,4-dichlorobenzoic acid and 2-(4,4-difluoropiperidin-1-yl)-2-(2-(difluoromethyl)pyrimidin-5-yl)ethanamine LCMS (MH⁺): m/z=465.1, $t_R$ (minutes, Method G)=2.16. $[\alpha]_D^{20}$=18.9 (c=3.6 mg/mL, CHCl$_3$).

Example 3d6

(−)2,4-dichloro-N-(2-(2-(difluoromethyl)pyrimidin-5-yl)-2-(4,4-difluoropiperidin-1-yl)ethyl)benzamide LCMS (MH⁺): m/z=465.1, $t_R$ (minutes, Method G)=2.16. $[\alpha]_D^{20}$=−16.5 (c=4.0 mg/mL, CHCl$_3$).

Example 3e6

(+)2-chloro-3-methoxy-N-(2-(2-(difluoromethyl)pyrimidin-5-yl)-2-(4,4-difluoropiperidin-1-yl)ethyl)benzamide

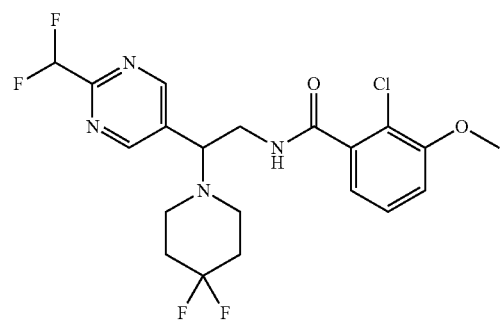 [SMILES: COc1cccc(C(=O)NCC(c2cnc(C(F)F)nc2)N2CCC(F)(F)CC2)c1Cl]

From 2-chloro-3-methoxybenzoic acid and 2-(4,4-difluoropiperidin-1-yl)-2-(2-(difluoromethyl)pyrimidin-5-yl)ethanamine LCMS (MH⁺): m/z=461.1, $t_R$ (minutes, Method I)=2.26. $[\alpha]_D^{20}$=19.6 (c=3.7 mg/mL, CHCl$_3$).

Example 3f6

(−)2-chloro-3-methoxy-N-(2-(2-(difluoromethyl)pyrimidin-5-yl)-2-(4,4-difluoropiperidin-1-yl)ethyl)benzamide LCMS (MH⁺): m/z=461.1, $t_R$ (minutes, Method I)=2.26. $[\alpha]_D^{20}$=−20.2 (c=4.0 mg/mL, CHCl$_3$).

Example 3g6

(+)2-chloro-3-fluoro-N-(2-(2-(difluoromethyl)pyrimidin-5-yl)-2-(4,4-difluoropiperidin-1-yl)ethyl)benzamide

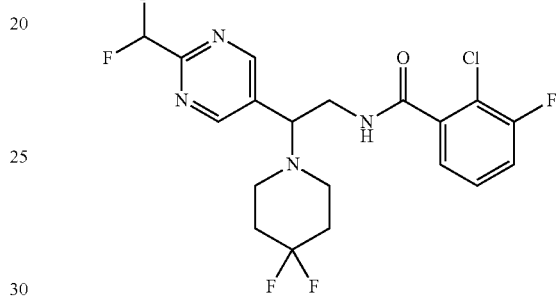

From 2-chloro-3-fluorobenzoic acid and 2-(4,4-difluoropiperidin-1-yl)-2-(2-(difluoromethyl)pyrimidin-5-yl)ethanamine LCMS (MH⁺): m/z=449.1, $t_R$ (minutes, Method E)=2.62. $[\alpha]_D^{20}$=16.4 (c=3.8 mg/mL, CHCl$_3$).

Example 3h6

(−)2-chloro-3-fluoro-N-(2-(2-(difluoromethyl)pyrimidin-5-yl)-2-(4,4-difluoropiperidin-1-yl)ethyl)benzamide LCMS (MH⁺): m/z=449.1, $t_R$ (minutes, Method E)=2.63. $[\alpha]_D^{20}$=−14.1 (c=3.8 mg/mL, CHCl$_3$).

Example 3i6

(+)2-chloro-N-(2-(2-(difluoromethyl)pyrimidin-5-yl)-2-morpholinoethyl)-3-methoxybenzamide

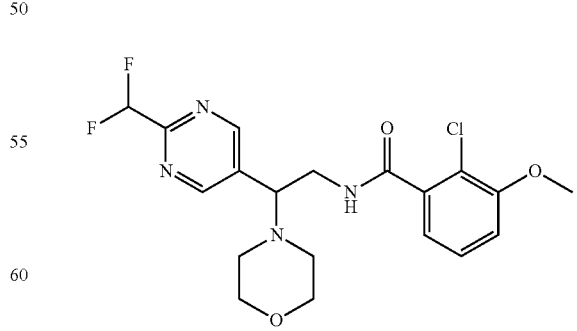

From 2-chloro-3-methoxybenzoic acid and 2-(2-(difluoromethyl)pyrimidin-5-yl)-2-morpholinoethanamine LCMS (MH⁺): m/z=427.1, $t_R$ (minutes, Method E)=2.06. $[\alpha]_D^{20}$=11.11 (c=1.8 mg/mL, CHCl$_3$).

Example 3j6

(−)2-chloro-N-(2-(2-(difluoromethyl)pyrimidin-5-yl)-2-morpholinoethyl)-3-methoxybenzamide LCMS (MH+): m/z=427.1, $t_R$ (minutes, Method E)=2.05. $[\alpha]_D^{20}$=−10.78 (c=1.67 mg/mL, CHCl$_3$).

Example 3k6

(+)2,4-dichloro-N-(2-(2-(difluoromethyl)pyrimidin-5-yl)-2-morpholinoethyl)benzamide

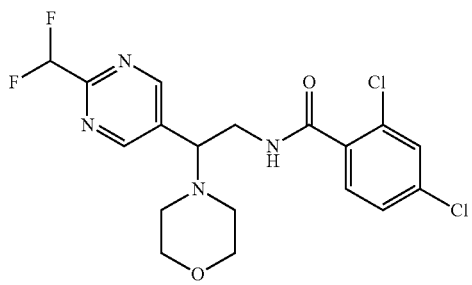 [SMILES: O=C(NCC(c1cnc(C(F)F)nc1)N1CCOCC1)c1ccc(Cl)cc1Cl]

From 2,4-dichlorobenzoic acid and 2-(2-(difluoromethyl)pyrimidin-5-yl)-2-morpholinoethanamine LCMS (MH+): m/z=431.1, $t_R$ (minutes, Method F)=2.32. $[\alpha]_D^{20}$=15.0 (c=1.0 mg/mL, CHCl$_3$).

Example 3l6

(−)2,4-dichloro-N-(2-(2-(difluoromethyl)pyrimidin-5-yl)-2-morpholinoethyl)benzamide LCMS (MH+): m/z=431.1, $t_R$ (minutes, Method E)=2.31. $[\alpha]_D^{20}$=−15.74 (c=1.08 mg/mL, CHCl$_3$).

Example 3m6

(+)2-chloro-N-(2-(2-(difluoromethyl)pyrimidin-5-yl)-2-morpholinoethyl)-3-(trifluoromethyl)benzamide

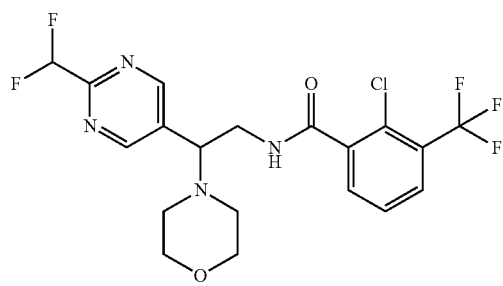 [SMILES: O=C(NCC(c1cnc(C(F)F)nc1)N1CCOCC1)c1cccc(C(F)(F)F)c1Cl]

From 2-chloro-3-(trifluoromethyl)benzoic acid and 2-(2-(difluoromethyl)pyrimidin-5-yl)-2-morpholinoethanamine LCMS (MH+): m/z=465.1, $t_R$ (minutes, Method E)=2.42. $[\alpha]_D^{20}$=17.0 (c=1.0 mg/mL, CHCl$_3$).

Example 3n6

(−)2-chloro-N-(2-(2-(difluoromethyl)pyrimidin-5-yl)-2-morpholinoethyl)-3-(trifluoromethyl)benzamide LCMS (MH+): m/z=465.1, $t_R$ (minutes, Method E)=2.42. $[\alpha]_D^{20}$=−19.42 (c=1.03 mg/mL, CHCl$_3$).

Example 4

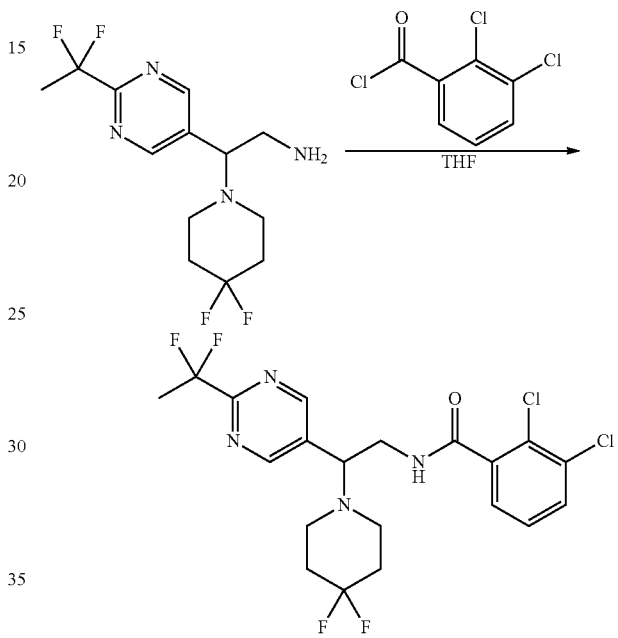

2-(2-(1,1-Difluoroethyl)pyrimidin-5-yl)-2-(4,4-difluoropiperidin-1-yl)ethanamine (34 mg, 0.044 mmol, 40% pure) and 2,3-dichlorobenzoyl chloride (65 mg, 0.31 mmol), was dissolved in anhydrous THF (4400 mg, 5 ml, 61.0 mmol), DIPEA (111 mg, 0.15 ml, 0.859 mmol) was added and stirred over night. The solution was concentrated and purified by column chromatography on silica gel (petroleum ether: EtOAc=1:0 to 0:1) followed by HPLC, to afford 2,3-dichloro-N-(2-(2-(1,1-difluoroethyl)pyrimidin-5-yl)-2-(4,4-difluoropiperidin-1-yl)ethyl)benzamide (10 mg, 47% yield).

LCMS (MH+): m/z=479.3, $t_R$ (minutes, Method D)=0.71.

Example 5

2,3-Dichloro-N-(2-(2-methylpyrimidin-5-yl)-2-(4-oxopiperidin-1-yl)ethyl)benzamide

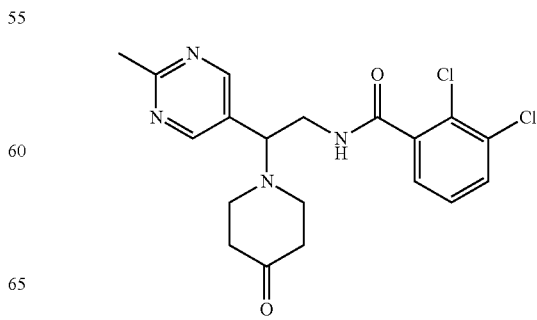

To a solution of 2,3-dichloro-N-(2-(4-hydroxypiperidin-1-yl)-2-(2-methylpyrimidin-5-yl)ethyl)benzamide (130 mg, 0.32 mmol) in DCM (5 mL) was added 4 Å molecular sieves (1.3 g), NMO (205 mg, 1.75 mmol) and TPAP (2.2 mg). The mixture was stirred at room temperature overnight. The resulting mixture was filtered. The filtrate was washed with water, dried over Na2SO4 and concentrated. The residue was purified by preparative TLC (EtOAc:MeOH=100:3) to give 2,3-dichloro-N-(2-(2-methylpyrimidin-5-yl)-2-(4-oxopiperidin-1-yl)ethyl)benzamide (31 mg, yield: 24%) as a white solid. $^1$HNMR (CDCl$_3$, 400 MHz): δ8.59 (s, 2H), 7.56 (dd, J=8.0 Hz, 1.6 Hz, 1H), 7.49 (dd, J=7.6 Hz, 1.6 Hz, 1H), 7.34-7.27 (m, 1H), 6.63 (br, 1H), 4.08-3.82 (m, 3H), 2.95-2.82 (m, 2H), 2.79-2.65 (m, 5H), 2.55-2.40 (m, 4H). LCMS (MH+): m/z=425.0, $t_R$ (minutes, Method F)=1.75

The following compounds were synthesized Ma similar way:

Example 51

2,4-dichloro-N-(2-(2-methylpyrimidin-5-yl)-2-(-1-yl)ethyl)benzamide

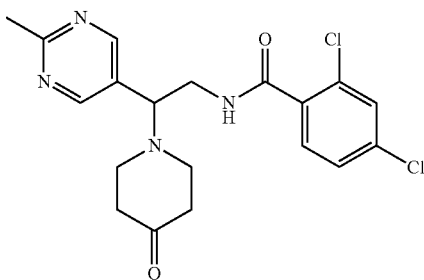 [SMILES: Cc1ncc(C(CNC(=O)c2ccc(Cl)cc2Cl)N2CCC(=O)CC2)cn1]

From 2,4-dichlorobenzoic acid and 2-(4-oxopiperidin-1-yl)-2-(2-methylpyrimidin-5-yl)ethanamine.
LCMS (MH+): m/z=425.1, $t_R$ (minutes, Method F)=2.01

Example 6

P2X$_7$ Binding Assay

This example illustrates representative assays for use in evaluating the test compounds for antagonist activity. Compounds of the present invention were tested in vitro for their ability to act as antagonists to the P2X$_7$ receptor.

Screening assays to determine P2X$_7$ receptor antagonism are well known to the person skilled in the art. Functional assays, such as second messenger assays, and cytokine measurement assays done in vitro are also well known in the art and may be used to assess the specific binding and cellular activity of P2X$_7$ receptor compounds.

In Vitro Assay Example

Cell culture: 293 HEK cells, stably transfected with plasmids capable of expressing human P2X$_7$ receptor, were cultured by standard methods. Cells were plated to cell density of approximately 15,000 cells/well in 384-well assay plates (50 μl/well) with 1.5% low serum media (DMEM, 1.5% BCS, 1% L-glut (2 mM), 1% P/S).

293 HEK cells, stably transfected with plasmids capable of expressing rat or mouse P2X$_7$ receptor, were cultured by standard methods. Cells were plated to cell density of approximately 15,000 cells/well in 384-well assay plates (50 μl/well) with 1.5% low serum media (DMEM, 1.5% FBS, 1% L-glut (2 mM), 10 mM HEPES, 1% P/S). Cells were plated 24 hours prior to assay. Cells expressing human, rat or mouse P2X$_7$ receptor were assayed in the following manner.

Fluorescent Imaging Plate Reader (FLIPR) assay: Briefly, 293-human or mouse P2X$_7$ stable cells were incubated in sucrose buffer, pH 7.4 [KCl (5 mM), NaH$_2$PO$_4$.2H$_2$O (9.6 mM), HEPES (25 mM), sucrose (280 mM), glucose (5 mM), CaCl$_2$ (0.5 mM), and probenecid (0.1425 g in 3 mL 1N NaOH was added for 500 mL solution)] in 384-well plates.

293-rat P2X$_7$ stable cells were incubated in HHPB (pH 7.4) [consisting of Hank's BSS (1X); HEPES (pH 7.4) (20 mM) (Sigma); probenecid (0.710 g15 mL 1N NaOH) (Sigma); and BSA (0.05%) (Roche) which was added after the pH had been adjusted] in 384-well plates. Fluo-4 NW dye mix (Molecular Probes, Inc., Eugene, Oreg., USA) was prepared in buffer (see manufacturer's instructions). Cell plates were removed from the 37° C. incubator, the media discarded and then 30 μL of dye was added to each well. Plates were placed in the 37° C., non-CO$_2$ incubator for 30 minutes and then room temperature for 30 minutes.

Two sets of drug plates were prepared: A) Mixtures of compound plus agonist were prepared as follows, in order to determine close response: BzATP: 11 point ½ log, diluted in buffer, starting from 1 mM. Testing compounds: 11 point ½ log, diluted in 2% DMSO buffer starting from 10 μM. B) Agonist only mixture was prepared with BzATP at a single concentration in buffer (concentration determined by dose response).

Compound mixtures (A) were added to assay plates containing cells and placed at room temperature for 30 minutes, then BzATP (B) was added. Fluorescence was read using the Tetra FLIPR® (Molecular Devices, Inc., Sunnyvale, Calif., USA) and IC$_{50}$ values were calculated by standard methods to determine antagonist activity.

Assay for stimulating IL1β release from THP-1 cells: THP-1 cells (The Global Bioresource Center; ATCC #: TIB-202™) were differentiated by incubation with 10 ng/mL IFN-gamma (Sigma, Cat#: 13265) in T150 plates, at a cell density of 0.5 E$^6$cells/mL, in RPMI1640 media (ATCC, Cat#30-2001) with 10% FBS and 1% P/S for 48 hours. The cells then were stimulated with 100 ng/mL LPS (Sigma, Cat#: L4516) in serum free CTL Test media (Sigma Cat#: CTLT-005), without L-glutamine and antibiotics, for 3 hours. Test compounds (antagonists) were added and incubated for 30 minutes. BzATP (at final concentration of 1 mM) was added and incubated for 30 minutes.

Cell plates were centrifuged at 3000 rpm for 5 minutes and the supernatants were immediately collected for AlphaL-ISA® immunoassay (PerkinElmer Inc., Waltham, Mass., USA; Catalog No. AL220C) or aliquoted and stored at <-20 C. The AlphaLISA® immunoassay was performed according to the manufacturer's instructions.

TABLE 1

Exemplified IC$_{50}$ values of compounds of the invention:

| Chemical name | P2X7 IC$_{50}$ (nM) |
|---|---|
| 2-Chloro-5-methyl-N-(2-morpholin-4-yl-2-pyridin-3-yl-ethyl)-benzamide | 3000 |
| 2-Chloro-5-methyl-N-(2-morpholin-4-yl-2-pyridin-4-yl-ethyl)-benzamide | 2700 |
| 2,3-Dichloro-N-(2-morpholin-4-yl-2-pyridin-3-yl-ethyl)-benzamide | 1100 |

TABLE 1-continued

Exemplified IC$_{50}$ values of compounds of the invention:

| Chemical name | P2X7 IC$_{50}$ (nM) |
|---|---|
| 2,3-Dichloro-N-(2-morpholin-4-yl-2-pyridin-4-yl-ethyl)-benzamide | 750 |
| 2,3-Dimethyl-N-(2-morpholin-4-yl-2-pyridin-3-yl-ethyl)-benzamide | 2700 |
| 2,3-Dimethyl-N-(2-morpholin-4-yl-2-pyridin-4-yl-ethyl)-benzamide | 1400 |
| 2,3-Dichloro-N-[2-(4-fluoro-phenyl)-2-morpholin-4-yl-ethyl]benzamide | 11 |
| 2,3-Dichloro-N-[2-(4-methoxy-phenyl)-2-piperidin-1-yl-ethyl]benzamide | 350 |
| 2,3-Dichloro-N-[2-(4-methoxy-phenyl)-2-morpholin-4-yl-ethyl]benzamide | 13 |
| N-[2-(4-Fluoro-phenyl)-2-morpholin-4-yl-ethyl]-2,3-dimethyl-benzamide | 20 |
| N-[2-(4-Methoxy-phenyl)-2-piperidin-1-yl-ethyl]-2,3-dimethyl-benzamide | 420 |
| N-[2-(4-Methoxy-phenyl)-2-morpholin-4-yl-ethyl]-2,3-dimethyl-benzamide | 47 |
| 2-Chloro-N-[2-(4-fluoro-phenyl)-2-morpholin-4-yl-ethyl]-5-methyl-benzamide | 21 |
| 2-Chloro-N-[2-(4-methoxy-phenyl)-2-piperidin-1-yl-ethyl]-5-methyl-benzamide | 650 |
| 2-Chloro-N-[2-(4-methoxy-phenyl)-2-morpholin-4-yl-ethyl]-5-methyl-benzamide | 59 |
| N-[2-(4-Fluoro-phenyl)-2-morpholin-4-yl-ethyl]-2-methyl-benzamide | 110 |
| N-[2-(4-Methoxy-phenyl)-2-piperidin-1-yl-ethyl]-2-methyl-benzamide | 3900 |
| N-[2-(4-Methoxy-phenyl)-2-morpholin-4-yl-ethyl]-2-methyl-benzamide | 500 |
| 2-Chloro-5-methyl-N-(2-morpholin-4-yl-2-p-tolyl-ethyl)-benzamide | 38 |
| N-[2-(4-Chloro-phenyl)-2-(4,4-difluoro-piperidin-1-yl)-ethyl]-2-methyl-benzamide | 2 |
| N-[2-(4-Chloro-phenyl)-2-(4,4-difluoro-piperidin-1-yl)-ethyl]-2,3-dimethyl-benzamide | 3.6 |
| 2,3-Dichloro-N-[2-(4-chloro-phenyl)-2-(4,4-difluoro-piperidin-1-yl)-ethyl]-benzamide | 46 |
| 2,3-Dichloro-N-[(S)-2-(4-chloro-phenyl)-2-morpholin-4-yl-ethyl]benzamide | 0.62 |
| 2,3-Dichloro-N-[2-(6-cyclopropyl-pyridin-3-yl)-2-morpholin-4-yl-ethyl]-benzamide | 8.2 |
| N-[(S)-2-(4-Chloro-phenyl)-2-morpholin-4-yl-ethyl]-2-methyl-benzamide | 9.3 |
| 2,3-dichloro-N-[2-morpholino-2-[6-(trifluoromethyl)-3-pyridyl]ethyl]benzamide | 4.6 |
| 2-Chloro-N-[(S)-2-(4-chloro-phenyl)-2-morpholin-4-yl-ethyl]-3-methyl-benzamide | 0.53 |
| 2,3-dichloro-N-[2-(6-chloro-3-pyridyl)-2-morpholino-ethyl]benzamide | 3.9 |
| 2,3-dichloro-N-(2-morpholino-2-pyrimidin-5-yl-ethyl)benzamide | 28 |
| 2,3-dichloro-N-[2-(2-methylpyrimidin-5-yl)-2-morpholino-ethyl]benzamide | 21 |
| 2,3-dichloro-N-[2-morpholino-2-[2-(trifluoromethyl)pyrimidin-5-yl]ethyl]benzamide | 8.2 |
| 2,3-Dichloro-N-[2-(4,4-difluoro-piperidin-1-yl)-2-(4-fluoro-phenyl)-ethyl]-benzamide | 0.33 |
| (−)2-chloro-N-[2-morpholino-2-[6-(trifluoromethyl)-3-pyridyl]ethyl]-3-(trifluoromethyl)benzamide | 12 |
| (+)2-chloro-N-[2-morpholino-2-[6-(trifluoromethyl)-3-pyridyl]ethyl]-3-(trifluoromethyl)benzamide | 24 |
| (−)2,3-dichloro-N-[2-morpholino-2-[2-(trifluoromethyl)pyrimidin-5-yl]ethyl]benzamide | 3.2 |
| (+)2,3-dichloro-N-[2-morpholino-2-[2-(trifluoromethyl)pyrimidin-5-yl]ethyl]benzamide | 4.8 |
| (−)2-chloro-N-[2-morpholino-2-[2-(trifluoromethyl)pyrimidin-5-yl]ethyl]-3-(trifluoromethyl)benzamide | 9.9 |
| (+)2-chloro-N-[2-morpholino-2-[2-(trifluoromethyl)pyrimidin-5-yl]ethyl]-3-(trifluoromethyl)benzamide | 17 |
| (−)2,3-dichloro-N-[2-morpholino-2-[6-(trifluoromethyl)-3-pyridyl]ethyl]benzamide | 2 |
| (+)2,3-dichloro-N-[2-morpholino-2-[6-(trifluoromethyl)-3-pyridyl]ethyl]benzamide | 5.5 |
| 2,3-dichloro-N-[2-(4,4-difluoro-1-piperidyl)-2-(4-methoxyphenyl)ethyl]benzamide | 0.6 |
| 2,3-dichloro-N-[2-(4,4-difluoro-1-piperidyl)-2-(6-fluoro-3-pyidyl)ethyl]benzamide | 0.89 |
| 2-chloro-N-[2-(4,4-difluoro-1-piperidyl)-2-(6-fluoro-3-pyridyl)ethyl]benzamide | 4 |
| 2,3-dichloro-N-[2-(4,4-difluoro-1-piperidyl)-2-[6-(trifluoromethyl)-3-pyridyl]ethyl]benzamide | 1.3 |
| 2-chloro-N-[2-(4,4-difluoro-1-piperidyl)-2-[6-(trifluoromethyl)-3-pyridyl]ethyl]benzamide | 1.8 |
| (−)2-chloro-N-[2-morpholino-2-[2-(trifluoromethyl)pyrimidin-5-yl]ethyl]benzamide | 15 |
| (+)2-chloro-N-[2-morpholino-2-[2-(trifluoromethyl)pyrimidin-5-yl]ethyl]benzamide | 30 |
| (−)2-fluoro-N-[2-morpholino-2-[2-(trifluoromethyl)pyrimidin-5-yl]ethyl]benzamide | 44 |
| (+)2,3-dichloro-N-[2-(6-methyl-3-pyridyl)-2-morpholino-ethyl]benzamide | 44 |
| 2,3-Dichloro-N-[2-(4-chloro-phenyl)-2-[1,4]oxazepan-4-yl-ethyl]-benzamide | 17 |
| (−)2-chloro-3-methoxy-N-(2-morpholino-2-(6-(trifluoromethyl)pyridin-3-yl)ethyl)benzamide | 3.5 |
| (+)2-chloro-3-methoxy-N-[2-morpholino-2-[6-(trifluoromethyl)-3-pyridyl]ethyl]benzamide | 14 |
| (−)2-chloro-6-fluoro-N-(2-morpholino-2-(6-(trifluoromethyl)pyridin-3-yl)ethyl)benzamide | 6.1 |
| (+)2-chloro-6-fluoro-N-[2-morpholino-2-[6-(trifluoromethyl)-3-pyridyl]ethyl]benzamide | 32 |
| (−)2-chloro-N-[2-(2-methylpyrimidin-5-yl)-2-morpholino-ethyl]benzamide | 110 |
| (+)2-chloro-N-[2-(2-methylpyrimidin-5-yl)-2-morpholino-ethyl]benzamide | 630 |
| (−)2,3-dichloro-N-[2-(2-methylpyrimidin-5-yl)-2-morpholino-ethyl]benzamide | 27 |
| (+)2,3-dichloro-N-[2-(2-methylpyrimidin-5-yl)-2-morpholino-ethyl]benzamide | 69 |
| (−)2,6-difluoro-N-[2-morpholino-2-[6-(trifluoromethyl)-3-pyridyl]ethyl]benzamide | 480 |
| (+)2,6-difluoro-N-[2-morpholino-2-[6-(trifluoromethyl)-3-pyridyl]ethyl]benzamide | 29 |
| (−)2-chloro-5-methylsulfonyl-N-[2-morpholino-2-[6-(trifluoromethyl)-3-pyridyl]ethyl]benzamide | 51 |
| (+)2-chloro-5-methylsulfonyl-N-[2-morpholino-2-[6-(trifluoromethyl)-3-pyridyl]ethyl]benzamide | 71 |
| (+)2-chloro-N-[2-(4-chlorophenyl)-2-morpholino-ethyl]-5-methylsulfonyl-benzamide | 180 |
| (−)2-chloro-N-[2-(4-chlorophenyl)-2-morpholino-ethyl]-5-methylsulfonyl-benzamide | 65 |
| 2,3-Dichloro-N-[2-(4-chloro-phenyl)-2-pyrrolidin-1-yl-ethyl]-benzamide | 1800 |
| (−)2-methoxy-N-[2-morpholino-2-[6-(trifluoromethyl)-3-pyridyl]ethyl]benzamide | 21 |
| (+)-2-methoxy-N-(2-morpholino-2-(6-(trifluoromethyl)pyridin-3-yl)ethyl)benzamide | 98 |
| (+)2-chloro-N-[2-(4-chlorophenyl)-2-morpholino-ethyl]-5-cyano-benzamide | 23 |
| (−)2-chloro-N-[2-(4-chlorophenyl)-2-morpholino-ethyl]-5-cyano-benzamide | 110 |

TABLE 1-continued

Exemplified IC$_{50}$ values of compounds of the invention:

| Chemical name | P2X7 IC$_{50}$ (nM) |
|---|---|
| 2,3-dichloro-N-[2-(4,4-difluoro-1-piperidyl)-2-[2-(trifluoromethyl)pyrimidin-5-yl]ethyl]benzamide | 0.65 |
| 2-chloro-N-[2-(4,4-difluoro-1-piperidyl)-2-[2-(trifluoromethyl)pyrimidin-5-yl]ethyl]benzamide | 2.8 |
| 2,3-dichloro-N-[2-(4,4-difluoro-1-piperidyl)-2-(2-methylpyrimidin-5-yl)ethyl]benzamide | 4.3 |
| (−)2-chloro-N-[2-(4-chlorophenyl)-2-morpholino-ethyl]-5-isopropylsulfonyl-benzamide | 47 |
| 2-Chloro-3-fluoro-N-[2-(2-methyl-pyrimidin-5-yl)-2-morpholin-4-yl-ethyl]-benzamide | 1200 |
| 2,6-dichloro-N-(2-(2-methylpyrimidin-5-yl)-2-morpholinoethyl)benzamide | 120 |
| 2-chloro-6-fluoro-N-(2-(2-methylprimidin-5-yl)-2-morpholinoethyl)benzamide | 590 |
| (+)2-chloro-N-[2-(4,4-difluoro-1-piperidyl)-2-(2-methylpyrimidin-5-yl)ethyl]benzamide | 13 |
| (−)2-chloro-N-[2-(4,4-difluoro-1-piperidyl)-2-(2-methylpyrimidin-5-yl)ethyl]benzamide | 24 |
| (+)2-chloro-N-[2-(4,4-difluoro-1-piperidyl)-2-[6-(trifluoromethyl)-3-pyridyl]ethyl]-3-fluoro-benzamide | 1.7 |
| (−)2-chloro-N-[2-(4,4-difluoro-1-piperidyl)-2-[6-(trifluoromethyl)-3-pyridyl]ethyl]-3-fluoro-benzamide | 5.7 |
| (+)2-chloro-N-[2-(4,4-difluoro-1-piperidyl)-2-[6-(trifluoromethyl)-3-pyridyl]ethyl]-6-fluoro-benzamide | 0.62 |
| (−)2-chloro-N-[2-(4,4-difluoro-1-piperidyl)-2-[6-(trifluoromethyl)-3-pyridyl]ethyl]-6-fluoro-benzamide | 3 |
| (+)2-chloro-N-[2-(4,4-difluoro-1-piperidyl)-2-(6-methyl-3-pyridyl)ethyl]-3-fluoro-benzamide | 33 |
| (−)2-chloro-N-[2-(4,4-difluoro-1-piperidyl)-2-(6-methyl-3-pridyl)ethyl]-3-fluoro-benzamide | 21 |
| (+)2-chloro-N-[2-(4,4-difluoro-1-piperidyl)-2-(6-methyl-3-pyridyl)ethyl]-6-fluoro-benzamide | 110 |
| (−)2-chloro-N-[2-(4,4-difluoro-1-piperidyl)-2-(6-methyl-3-pyridyl)ethyl]-6-fluoro-benzamide | 22 |
| 2,6-difluoro-N-(2-(2-methylpyrimidin-5-yl)-2-morpholinoethyl)benzamide | 1100 |
| (+)2-chloro-N-[2-(4,4-difluoro-1-piperidyl)-2-(2-methylpyrimidin-5-yl)ethyl]-3-fluoro-benzamide | 15 |
| (−)2-chloro-N-[2-(4,4-difluoro-1-piperidyl)-2-(2-methylpyrimidin-5-yl)ethyl]-3-fluoro-benzamide | 19 |
| (+)2-chloro-N-[2-(4,4-difluoro-1-piperidyl)-2-(2-methylpyrimidin-5-yl)ethyl]-6-fluoro-benzamide | 19 |
| (−)2-chloro-N-[2-(4,4-difluoro-1-piperidyl)-2-(2-methylpyrimidin-5-yl)ethyl]-6-fluoro-benzamide | 32 |
| (+)2-chloro-N-[2-(4,4-difluoro-1-piperidyl)-2-[2-(trifluoromethyl)pyrimidin-5-yl]ethyl]-6-fluoro-benzamide | 8.3 |
| (−)2-chloro-N-[2-(4,4-difluoro-1-piperidyl)-2-[2-(trifluoromethyl)pyrimidin-5-yl]ethyl]-6-fluoro-benzamide | 8.2 |
| (+)2-chloro-N-[2-(4,4-difluoro-1-piperidyl)-2-[2-(trifluoromethyl)pyrimidin-5-yl]ethyl]-3-fluoro-benzamide | 1.7 |
| (−)2-chloro-N-[2-(4,4-difluoro-1-piperidyl)-2-[2-(trifluoromethyl)pyrimidin-5-yl]ethyl]-3-fluoro-benzamide | 4.2 |
| 2,3-dichloro-N-[2-(4,4-dimethyl-1-piperidyl)-2-[2-(trifluoromethyl)pyrimidin-5-yl]ethyl]benzamide | 2500 |
| 2-chloro-N-[2-(4,4-dimethyl-1-piperidyl)-2-[2-(trifluoromethyl)pyrimidin-5-yl]ethyl]-3-fluoro-benzamide | 3600 |
| 2,3-dichloro-N-(2-(2-methylpyrimidin-5-yl)-2-(1,4-oxazepan-4-yl)ethyl)benzamide | 29 |
| 2,6-dichloro-N-(2-(2-methylpyrimidin-5-yl)-2-(1,4-oxazepan-4-yl)ethyl)benzamide | 740 |
| 2-chloro-6-fluoro-N-(2-(2-methylpyrimidin-5-yl)-2-(1,4-oxazepan-4-yl)ethyl)benzamide | 820 |
| 2-chloro-N-(2-(2-methylpyrimidin-5-yl)-2-(1,4-oxazepan-4-yl)ethyl)benzamide | 680 |
| 2-chloro-3-fluoro-N-(2-(2-methylpyrimidin-5-yl)-2-(1,4-oxazepan-4-yl)ethyl)benzamide | 330 |
| (−)2-chloro-3-methoxy-N-[2-morpholino-2-[2-(trifluoromethyl)pyrimidin-5-yl]ethyl]benzamide | 8.2 |
| (+)2-chloro-3-methoxy-N-[2-morpholino-2-[2-(trifluoromethyl)pyrimidin-5-yl]ethyl]benzamide | 16 |
| (−)3-methoxy-2-methyl-N-[2-morpholino-2-[6-(trifluoromethyl)-3-pyridyl]ethyl]benzamide | 16 |
| (+)3-methoxy-2-methyl-N-[2-morpholino-2-[6-(trifluoromethyl)-3-pyridyl]ethyl]benzamide | 13 |
| (−)2-chloro-N-[2-(4,4-difluoro-1-piperidyl)-2-(4-fluorophenyl)ethyl]-3-methoxy-benzamide | 2.6 |
| (+)2-chloro-N-[2-(4,4-difluoro-1-piperidyl)-2-(4-fluorophenyl)ethyl]-3-methoxy-benzamide | 2.6 |
| 2,3-dichloro-N-(2-(2-methylpyrimidin-5-yl)-2-(3-methylpyrrolidin-1-yl)ethyl)benzamide | 1000 |
| 2,3-dichloro-N-(2-(2-methylpyrimidin-5-yl)-2-(3,3,4,4-tetrafluoropyrrolidin-1-yl)ethyl)benzamide | 2.6 |
| (−)2-chloro-N-[2-(4-chlorophenyl)-2-morpholino-ethyl]-3-methoxy-benzamide | 1.5 |
| (+)2-chloro-N-[2-(4-chlorophenyl)-2-morpholino-ethyl]-3-methoxy-benzamide | 4.2 |
| (+)2-chloro-N-[2-(3,3-difluoro-1-piperidyl)-2-(2-methylpyrimidin-5-yl)ethyl]-6-fluoro-benzamide | 53 |
| (−)2-chloro-N-[2-(3,3-difluoro-1-piperidyl)-2-(2-methylpyrimidin-5-yl)ethyl]-6-fluoro-benzamide | 280 |
| (+)2-chloro-N-[2-(3,3-difluoro-1-piperidyl)-2-(2-methylpyrimidin-5-yl)ethyl]-3-fluoro-benzamide | 100 |
| (−)2-chloro-N-[2-(3,3-difluoro-1-piperidyl)-2-(2-methylpyrimidin-5-yl)ethyl]-3-fluoro-benzamide | 41 |
| (+)2,3-dichloro-N-[2-(3,3-difluoro-1-piperidyl)-2-(2-methylpyrimidin-5-yl)ethyl]benzamide | 14 |
| (+)2-chloro-N-[2-(3,3-difluoro-1-piperidyl)-2-(2-methylpyrimidin-5-yl)ethyl]benzamide | 85 |
| (−)2-chloro-N-[2-(3,3-difluoro-1-piperidyl)-2-(2-methylpyrimidin-5-yl)ethyl]benzamide | 28 |
| (+)2-chloro-N-[2-(4-fluoro-1-piperidyl)-2-[2-(trifluoromethyl)pyrimidin-5-yl]ethyl]benzamide | 15 |
| (−)2-chloro-N-[2-(4-fluoro-1-piperidyl)-2-[2-(trifluoromethyl)pyrimidin-5-yl]ethyl]benzamide | 13 |
| (+)2,6-dichloro-N-[2-(4-fluoro-1-piperidyl)-2-[2-(trifluoromethyl)pyrimidin-5-yl]ethyl]benzamide | 6.1 |
| (−)2,6-dichloro-N-[2-(4-fluoro-1-piperidyl)-2-[2-(trifluoromethyl)pyrimidin-5-yl]ethyl]benzamide | 15 |
| (+)2,3-dichloro-N-[2-(4-fluoro-1-piperidyl)-2-[2-(trifluoromethyl)pyrimidin-5-yl]ethyl]benzamide | 3.5 |
| (−)2,3-dichloro-N-[2-(4-fluoro-1-piperidyl)-2-[2-(trifluoromethyl)pyrimidin-5-yl]ethyl]benzamide | 4.7 |

TABLE 1-continued

Exemplified $IC_{50}$ values of compounds of the invention:

| Chemical name | P2X7 $IC_{50}$ (nM) |
|---|---|
| (+)2,6-dichloro-N-[2-(4-fluoro-1-piperidyl)-2-(2-methylpyrimidin-5-yl)ethyl]benzamide | 9.6 |
| (−)2,6-dichloro-N-[2-(4-fluoro-1-piperidyl)-2-(2-methylpyrimidin-5-yl)ethyl]benzamide | 53 |
| (+)2,3-dichloro-N-[2-(4-fluoro-1-piperidyl)-2-(2-methylpyrimidin-5-yl)ethyl]benzamide | 6.5 |
| (−)2,3-dichloro-N-[2-(4-fluoro-1-piperidyl)-2-(2-methylpyrimidin-5-yl)ethyl]benzamide | 14 |
| (+)2-chloro-N-[2-(4-fluoro-1-piperidyl)-2-(2-methylpyrimidin-5-yl)ethyl]benzamide | 50 |
| (−)2-chloro-N-[2-(4-fluoro-1-piperidyl)-2-(2-methylpyrimidin-5-yl)ethyl]benzamide | 45 |
| 2,4-dichloro-N-(2-morpholino-2-(2-(trifluoromethyl)pyrimidin-5-yl)ethyl)benzamide | 12 |
| (−)2,3-dichloro-N-[2-(4,4-difluoro-1-piperidyl)-2-(1-methylpyrazol-4-yl)ethyl]benzamide | 25 |
| (+)2,3-dichloro-N-[2-(4,4-difluoro-1-piperidyl)-2-(1-methylpyrazol-4-yl)ethyl]benzamide | 12 |
| (−)2,3-dichloro-N-[2-(4,4-difluoro-1-piperidyl)-2-(1-methylpyrazol-4-yl)ethyl]-5-fluoro-benzamide | 26 |
| (+)2,3-dichloro-N-[2-(4,4-difluoro-1-piperidyl)-2-(1-methylpyrazol-4-yl)ethyl]-5-fluoro-benzamide | 34 |
| (−)2-chloro-N-[2-(4,4-difluoro-1-piperidyl)-2-(1-methylpyrazol-4-yl)ethyl]benzamide | 230 |
| (+)2-chloro-N-[2-(4,4-difluoro-1-piperidyl)-2-(1-methylpyrazol-4-yl)ethyl]benzamide | 180 |
| (−)2-chloro-N-[2-(4,4-difluoro-1-piperidyl)-2-[2-(trifluoromethyl)pyrimidin-5-yl]ethyl]-3-methoxy-benzamide | 4.8 |
| (+)2-chloro-N-[2-(4,4-difluoro-1-piperidyl)-2-[2-(trifluoromethyl)pyrimidin-5-yl]ethyl]-3-methoxy-benzamide | 3.6 |
| (−)2,6-dichloro-N-[2-(4,4-difluoro-1-piperidyl)-2-[2-(trifluoromethyl)pyrimidin-5-yl]ethyl]benzamide | 6.9 |
| (+)2,6-dichloro-N-[2-(4,4-difluoro-1-piperidyl)-2-[2-(trifluoromethyl)pyrimidin-5-yl]ethyl]benzamide | 4.7 |
| (−)2,6-dichloro-N-[2-(4,4-difluoro-1-piperidyl)-2-[2-(trifluoromethyl)pyrimidin-5-yl]ethyl]-3-fluoro-benzamide | 4.9 |
| (+)2,6-dichloro-N-[2-(4,4-difluoro-1-piperidyl)-2-[2-(trifluoromethyl)pyrimidin-5-yl]ethyl]-3-fluoro-benzamide | 7.1 |
| (−)2-chloro-N-[2-(2-methylpyrimidin-5-yl)-2-(1-piperidyl)ethyl]benzamide | 120 |
| (+)2-chloro-N-[2-(2-methylpyrimidin-5-yl)-2-(1-piperidyl)ethyl]benzamide | 59 |
| (−)2,3-dichloro-N-[2-(2-methylpyrimidin-5-yl)-2-(1-piperidyl)ethyl]benzamide | 21 |
| (+)2,3-dichloro-N-[2-(2-methylpyrimidin-5-yl)-2-(1-piperidyl)ethyl]benzamide | 8.9 |
| (−)2,3-dichloro-N-[2-(4,4-difluoro-1-piperidyl)-2-[2-(trifluoromethyl)pyrimidin-5-yl]ethyl]-5-fluoro-benzamide | 2.2 |
| (+)2,3-dichloro-N-[2-(4,4-difluoro-1-piperidyl)-2-[2-(trifluoromethyl)pyrimidin-5-yl]ethyl]-5-fluoro-benzamide | 4.9 |
| (−)2,6-dichloro-N-[2-(4,4-difluoro-1-piperidyl)-2-(1-methylpyrazol-4-yl)ethyl]benzamide | 44 |
| (+)2,6-dichloro-N-[2-(4,4-difluoro-1-piperidyl)-2-(1-methylpyrazol-4-yl)ethyl]benzamide | 56 |
| (−)2-chloro-N-[2-[2-(difluoromethyl)pyrimidin-5-yl]-2-morpholino-ethyl]benzamide | 15 |
| (+)2-chloro-N-[2-[2-(difluoromethyl)pyrimidin-5-yl]-2-morpholino-ethyl]benzamide | 60 |
| (−)2-chloro-N-[2-(4,4-difluoro-1-piperidyl)-2-(2-methylpyrimidin-5-yl)ethyl]-3-methoxy-benzamide | 11 |
| (+)2-chloro-N-[2-(4,4-difluoro-1-piperidyl)-2-(2-methylpyrimidin-5-yl)ethyl]-3-methoxy-benzamide | 12 |
| (−)2,6-dichloro-N-[2-(4,4-difluoro-1-piperidyl)-2-(2-methylpyrimidin-5-yl)ethyl]-3-fluoro-benzamide | 37 |
| (+)2,6-dichloro-N-[2-(4,4-difluoro-1-piperidyl)-2-(2-methylpyrimidin-5-yl)ethyl]-3-fluoro-benzamide | 25 |
| (−)2,6-dichloro-N-[2-(4,4-difluoro-1-piperidyl)-2-(2-methylpyrimidin-5-yl)ethyl]benzamide | 22 |
| (+)2,6-dichloro-N-[2-(4,4-difluoro-1-piperidyl)-2-(2-methylpyrimidin-5-yl)ethyl]benzamide | 19 |
| (−)2,3-dichloro-N-[2-(4,4-difluoro-1-piperidyl)-2-(2-methylpyrimidin-5-yl)ethyl]-5-fluoro-benzamide | 14 |
| (+)2,3-dichloro-N-[2-(4,4-difluoro-1-piperidyl)-2-(2-methylpyrimidin-5-yl)ethyl]-5-fluoro-benzamide | 5.1 |
| (−)2,3-dichloro-N-[2-(4,4-difluoro-1-piperidyl)-2-(2-methylpyrimidin-5-yl)ethyl]benzamide | 5.8 |
| (+)2,3-dichloro-N-[2-(4,4-difluoro-1-piperidyl)-2-(2-methylpyrimidin-5-yl)ethyl]benzamide | 3.2 |
| (−)2,3-dichloro-N-[2-[2-(difluoromethyl)pyrimidin-5-yl]-2-morpholino-ethyl]benzamide | 9.6 |
| (+)2,3-dichloro-N-[2-[2-(difluoromethyl)pyrimidin-5-yl]-2-morpholino-ethyl]benzamide | 3.9 |
| (−)2-chloro-N-[2-[2-(difluoromethyl)pyrimidin-5-yl]-2-morpholino-ethyl]-3-fluoro-benzamide | 38 |
| (+)2-chloro-N-[2-[2-(difluoromethyl)pyrimidin-5-yl]-2-morpholino-ethyl]-3-fluoro-benzamide | 4.8 |
| (−)2-chloro-N-[2-(2-cyclopropylpyrimidin-5-yl)-2-(4,4-difluoro-1-piperidyl)ethyl]benzamide | 7.6 |
| (+)2-chloro-N-[2-(2-cyclopropylpyrimidin-5-yl)-2-(4,4-difluoro-1-piperidyl)ethyl]benzamide | 3 |
| (−)2,6-dichloro-N-[2-(2-cyclopropylpyrimidin-5-yl)-2-(4,4-difluoro-1-piperidyl)ethyl]benzamide | 5.8 |
| (+)2,6-dichloro-N-[2-(2-cyclopropylpyrimidin-5-yl)-2-(4,4-difluoro-1-piperidyl)ethyl]benzamide | 5.3 |
| (−)2-chloro-N-[2-(4,4-difluoro-1-piperidyl)-2-(2-ethylpyrimidin-5-yl)ethyl]benzamide | 17 |
| (+)2-chloro-N-[2-(4,4-difluoro-1-piperidyl)-2-(2-ethylpyrimidin-5-yl)ethyl]benzamide | 12 |
| (−)2,6-dichloro-N-[2-(4,4-difluoro-1-piperidyl)-2-(2-ethylpyrimidin-5-yl)ethyl]benzamide | 27 |
| (+)2,6-dichloro-N-[2-(4,4-difluoro-1-piperidyl)-2-(2-ethylpyrimidin-5-yl)ethyl]benzamide | 15 |
| (−)2-chloro-3-(difluoromethoxy)-N-[2-(4,4-difluoro-1-piperidyl)-2-(2-methylpyrimidin-5-yl)ethyl]benzamide | 37 |
| (+)2-chloro-3-(difluoromethoxy)-N-[2-(4,4-difluoro-1-piperidyl)-2-(2-methylpyrimidin-5-yl)ethyl]benzamide | 7 |
| (−)2,3-dichloro-N-[2-(4,4-difluoro-1-piperidyl)-2-(2-ethylpyrimidin-5-yl)ethyl]benzamide | 4.9 |
| (+)2,3-dichloro-N-[2-(4,4-difluoro-1-piperidyl)-2-(2-ethylpyrimidin-5-yl)ethyl]benzamide | 2.6 |

TABLE 1-continued

Exemplified IC$_{50}$ values of compounds of the invention:

| Chemical name | P2X7 IC$_{50}$ (nM) |
|---|---|
| (−)2-chloro-N-[2-(4,4-difluoro-1-piperidyl)-2-(2-ethylpyrimidin-5-yl)ethyl]-6-fluoro-benzamide | 36 |
| (+)2-chloro-N-[2-(4,4-difluoro-1-piperidyl)-2-(2-ethylpyrimidin-5-yl)ethyl]-6-fluoro-benzamide | 14 |
| (−)2,3-dichloro-N-[2-(2-cyclopropylpyrimidin-5-yl)-2-(4,4-difluoro-1-piperidyl)ethyl]benzamide | 3.5 |
| (+)2,3-dichloro-N-[2-(2-cyclopropylpyrimidin-5-yl)-2-(4,4-difluoro-1-piperidyl)ethyl]benzamide | 4.3 |
| (−)2-chloro-N-[2-(2-cyclopropylpyrimidin-5-yl)-2-(4,4-difluoro-1-piperidyl)ethyl]-6-fluoro-benzamide | 11 |
| (+)2-chloro-N-[2-(2-cyclopropylpyrimidin-5-yl)-2-(4,4-difluoro-1-piperidyl)ethyl]-6-fluoro-benzamide | 9.9 |
| 2,4-dichloro-N-(2-(4,4-difluoropiperidin-1-yl)-2-(2-methylpyrimidin-5-yl)ethyl)benzamide | 44 |
| 2,3-dichloro-N-(2-(3-methylpiperidin-1-yl)-2-(2-methylpyrimidin-5-yl)ethyl)benzamide | 170 |
| (−)2-chloro-N-[2-(4,4-difluoro-1-piperidyl)-2-[2-(trifluoromethyl)pyrimidin-5-yl]ethyl]-4,6-difluoro-benzamide | 31 |
| (+)2-chloro-N-[2-(4,4-difluoro-1-piperidyl)-2-[2-(trifluoromethyl)pyrimidin-5-yl]ethyl]-4,6-difluoro-benzamide | 9.4 |
| (−)2-chloro-N-[2-(4,4-difluoro-1-piperidyl)-2-[2-(trifluoromethyl)pyrimidin-5-yl]ethyl]-6-fluoro-3-methoxy-benzamide | 31 |
| (+)2-chloro-N-[2-(4,4-difluoro-1-piperidyl)-2-[2-(tifluoromethyl)pyrimidin-5-yl]ethyl]-6-fluoro-3-methoxy-benzamide | 8.9 |
| 2,3-dichloro-N-(2-(2-isopropylpiperidin-1-yl)-2-(2-methylpyrimidin-5-yl)ethyl)benzamide | 1900 |
| 2,3-dichloro-N-(2-(4,4-difluoropiperidin-1-yl)-2-(2-(dimethylamino)pyrimidin-5-yl)ethyl)benzamide | 6.6 |
| N-(2-(2-azabicyclo[2.2.1]heptan-2-yl)-2-(2-methylpyrimidin-5-yl)ethyl)-2,3-dichlorobenzamide | 3200 |
| 2,3-dichloro-N-(2-(2-methylpiperidin-1-yl)-2-(2-methylpyrimidin-5-yl)ethyl)benzamide | 310 |
| (−)2,4-dichloro-N-[2-(4,4-difluoro-1-piperidyl)-2-[2-(trifluoromethyl)pyrimidin-5-yl]ethyl]benzamide | 6.4 |
| (+)2,4-dichloro-N-[2-(4,4-difluoro-1-piperidyl)-2-[2-(trifluoromethyl)pyrimidin-5-yl]ethyl]benzamide | 5.6 |
| (−)2,4-dichloro-N-[2-(4,4-difluoro-1-piperidyl)-2-[2-(trifluoromethyl)pyrimidin-5-yl]ethyl]-6-fluoro-benzamide | 6.5 |
| (+)2,4-dichloro-N-[2-(4,4-difluoro-1-piperidyl)-2-[2-(trifluoromethyl)pyrimidin-5-yl]ethyl]-6-fluoro-benzamide | 4.7 |
| (−)2-chloro-N-[2-(4,4-difluoro-1-piperidyl)-2-[2-(trifluoromethyl)pyrimidin-5-yl]ethyl]-4-methoxy-benzamide | 2.2 |
| (+)2-chloro-N-[2-(4,4-difluoro-1-piperidyl)-2-[2-(trifluoromethyl)pyrimidin-5-yl]ethyl]-4-methoxy-benzamide | 4.3 |
| (−)2-chloro-N-[2-(4,4-difluoro-1-piperidyl)-2-[2-(trifluoromethyl)pyrimidin-5-yl]ethyl]-3,4-dimethoxy-benzamide | 7.8 |
| (+)2-chloro-N-[2-(4,4-difluoro-1-piperidyl)-2-[2-(trifluoromethyl)pyrimidin-5-yl]ethyl]-3,4-dimethoxy-benzamide | 14 |
| 2,3-dichloro-N-[2-(4-methoxy-1-piperidyl)-2-(2-methylpyrimidin-5-yl)ethyl]benzamide | 3800 |
| (−)2,6-dichloro-N-[2-(4,4-difluoro-1-piperidyl)-2-[2-(trifluoromethyl)pyrimidin-5-yl]ethyl]-4-fluoro-benzamide | 15 |
| (+)2,6-dichloro-N-[2-(4,4-difluoro-1-piperidyl)-2-[2-(trifluoromethyl)pyrimidin-5-yl]ethyl]-4-fluoro-benzamide | 7.5 |
| (−)2-chloro-N-[2-(4,4-difluoro-1-piperidyl)-2-(2-methylpyrimidin-5-yl)ethyl]-3-(trifluoromethoxy)benzamide | 40 |
| (+)2-chloro-N-[2-(4,4-difluoro-1-piperidyl)-2-(2-methylpyrimidin-5-yl)ethyl]-3-(trifluoromethoxy)benzamide | 21 |
| 2,3-dichloro-N-[2-(2-methylpyrimidin-5-yl)-2-(4-oxo-1-piperidyl)ethyl]benzamide | 19 |
| 2,4-dichloro-N-[2-(2-methylpyrimidin-5-yl)-2-(4-oxo-1-piperidyl)ethyl]benzamide | 970 |
| 2,3-dichloro-N-[2-(4-chloro-1-piperidyl)-2-(2-methylpyrimidin-5-yl)ethyl]benzamide | 5.7 |
| 2,4-dichloro-N-[2-(4-chloro-1-piperidyl)-2-(2-methylpyrimidin-5-yl)ethyl]benzamide | 280 |
| 2-chloro-3-fluoro-N-(2-morpholino-2-(2-(trifluoromethyl)pyrimidin-5-yl)ethyl)benzamide | 11 |
| (+)2-chloro-N-[2-[6-(difluoromethyl)-3-pyridyl]-2-(4,4-difluoro-1-piperidyl)ethyl]benzamide | 9 |
| (−)2-chloro-N-[2-[6-(difluoromethyl)-3-pyridyl]-2-(4,4-difluoro-1-piperidyl)ethyl]benzamide | 12 |
| (+)2,3-dichloro-N-[2-[6-(difluoromethyl)-3-pyridyl]-2-(4,4-difluoro-1-piperidyl)ethyl]benzamide | 2.4 |
| (−)2,3-dichloro-N-[2-[6-(difluoromethyl)-3-pyridyl]-2-(4,4-difluoro-1-piperidyl)ethyl]benzamide | 4.2 |
| (+)2,6-dichloro-N-[2-[6-(difluoromethyl)-3-pyridyl]-2-(4,4-difluoro-1-piperidyl)ethyl]benzamide | 8.7 |
| (−)2,6-dichloro-N-[2-[6-(difluoromethyl)-3-pyridyl]-2-(4,4-difluoro-1-piperidyl)ethyl]benzamide | 5.5 |
| (+)2-chloro-N-[2-[6-(difluoromethyl)-3-pyridyl]-2-(4,4-difluoro-1-piperidyl)ethyl]-3-methoxy-benzamide | 2.3 |
| (−)2-chloro-N-[2-[6-(difluoromethyl)-3-pyridyl]-2-(4,4-difluoro-1-piperidyl)ethyl]-3-methoxy-benzamide | 1.9 |
| 2,3-Dichloro-N-[2-(4-chloro-phenyl)-2-morpholin-4-yl-ethyl]-benzamide | 0.6 |

What is claimed:
1. A compound of formula I

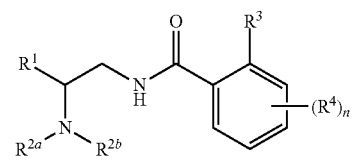

wherein R$^1$ is pyrimidyl optionally substituted with one or more C$_{1-6}$ alkyl, halogen, hydroxy, C$_{1-4}$ fluoroalkyl, C$_{3-6}$ cycloalkyl, C$_{1-6}$alkoxy, C$_{1-6}$ fluoroalkoxy, cyano or —SO$_2$R$^7$;
wherein R$^{2a}$ and R$^{2b}$ combine with the nitrogen to which they are attached to form piperazinyl, piperidinyl, morpholinyl, pyrrolidinyl, pyrrolo, imidazo, azetidinyl, 6 to 10 membered spiro(heterocyclyl), homomorpholinyl, homopiperidinyl or homopiperazinyl each of which is optionally substituted with one or more C$_{1-6}$ alkyl, C$_{1-6}$ alkenyl, C$_{3-6}$-cycloalkyl, C$_{1-6}$alkoxy, oxo, —NR$^5$R$^6$ or fluorines;

wherein R³ is halogen, $C_{1-4}$ fluoroalkyl, cyano, cyclopropyl, $C_{1-4}$alkyloxy, $C_{1-4}$fluoroalkyloxy, —SO$_2$R⁷, —NR⁵R⁶ or $C_{1-6}$alkyl;

wherein R⁴ is halogen, $C_{1-6}$ alkyl, $C_{1-4}$ fluoroalkyl, cyano, —SO$_2$R⁸, —NR⁵R⁶, $C_{1-6}$ alkoxy, $C_{1-4}$ fluoroalkoxy or $C_{3-6}$-cycloalkyl;

wherein R⁵ and R⁶ independently of each other are hydrogen or $C_{1-6}$ alkyl;

wherein R⁷ is $C_{1-6}$ alkyl, $C_{3-6}$ cycloalkyl, $C_{1-4}$fluoroalkyl and wherein n is 0-3; or a pharmaceutically acceptable salt thereof.

2. The compound of claim 1, wherein R²ᵃ and R²ᵇ combine with the nitrogen to which they are attached to form optionally substituted piperazinyl.

3. The compound of claim 1, wherein R²ᵃ and R²ᵇ combine with the nitrogen to which they are attached to form optionally substituted piperidinyl.

4. The compound of claim 1, wherein R²ᵃ and R²ᵇ combine with the nitrogen to which they are attached to form optionally substituted morpholinyl.

5. The compound of claim 1, wherein R²ᵃ and R²ᵇ combine with the nitrogen to which they are attached to form optionally substituted pyrrolidinyl.

6. The compound of claim 1, wherein R²ᵃ and R²ᵇ combine with the nitrogen to which they are attached to form optionally substituted pyrrolo.

7. The compound of claim 1, wherein R²ᵃ and R²ᵇ combine with the nitrogen to which they are attached to form optionally substituted imidazo.

8. The compound of claim 1, wherein R²ᵃ and R²ᵇ combine with the nitrogen to which they are attached to form optionally substituted 6 to 10 membered spiro(heterocyclyl).

9. The compound of claim 1, wherein R²ᵃ and R²ᵇ combine with the nitrogen to which they are attached to form optionally substituted homomorpholinyl.

10. The compound of claim 1, wherein R²ᵃ and R²ᵇ combine with the nitrogen to which they are attached to form optionally substituted homopiperidinyl.

11. The compound of claim 1, wherein R²ᵃ and R²ᵇ combine with the nitrogen to which they are attached to form optionally substituted homopiperazinyl.

12. The compound of claim 1, wherein R²ᵃ and R²ᵇ combine with the nitrogen to which they are attached to form optionally substituted azetidinyl.

13. The compound of claim 1, wherein R³ is chlorine, methyl or trifluoromethyl.

14. The compound of claim 1, wherein n is 0.

15. The compound of claim 1, wherein n is 1.

16. The compound of claim 1, wherein n is 2.

17. The compound of claim 1, wherein R⁴ is fluorine, chlorine, $C_{1-3}$ alkyl, $C_{1-4}$fluoroalkyl, cyano, $C_{1-3}$ alkoxy or $C_{1-4}$fluoroalkoxy.

18. A pharmaceutical composition comprising a compound of claim 1.

19. The compound of claim 1 wherein the compound is selected from the group consisting of:
- (−)2-chloro-N-[2-morpholino-2-[2-(trifluoromethyl)pyrimidin-5-yl]ethyl]benzamide;
- (+)2-chloro-N-[2-morpholino-2-[2-(trifluoromethyl)pyrimidin-5-yl]ethyl]benzamide;
- (−)2-fluoro-N-[2-morpholino-2-[2-(trifluoromethyl)pyrimidin-5-yl]ethyl]benzamide;
- (−)2-chloro-N-[2-(2-methylpyrimidin-5-yl)-2-morpholino-ethyl]benzamide;
- (+)2-chloro-N-[2-(2-methylpyrimidin-5-yl)-2-morpholino-ethyl]benzamide;
- (−)2,3-dichloro-N-[2-(2-methylpyrimidin-5-yl)-2-morpholino-ethyl]benzamide;
- (+)2,3-dichloro-N-[2-(2-methylpyrimidin-5-yl)-2-morpholino-ethyl]benzamide;
- 2,3-dichloro-N-[2-(4,4-difluoro-1-piperidyl)-2-[2-(trifluoromethyl)pyrimidin-5-yl]ethyl]benzamide;
- 2-chloro-N-[2-(4,4-difluoro-1-piperidyl)-2-[2-(trifluoromethyl)pyrimidin-5-yl]ethyl]benzamide;
- 2,3-dichloro-N-[2-(4,4-difluoro-1-piperidyl)-2-(2-methylpyrimidin-5-yl)ethyl]benzamide;
- 2-Chloro-3-fluoro-N-[2-(2-methyl-pyrimidin-5-yl)-2-morpholin-4-yl-ethyl]-benzamide;
- 2,6-dichloro-N-(2-(2-methylpyrimidin-5-yl)-2-morpholinoethyl)benzamide;
- 2-chloro-6-fluoro-N-(2-(2-methylpyrimidin-5-yl)-2-morpholinoethyl)benzamide;
- (+)2-chloro-N-[2-(4,4-difluoro-1-piperidyl)-2-(2-methylpyrimidin-5-yl)ethyl]benzamide;
- (−)2-chloro-N-[2-(4,4-difluoro-1-piperidyl)-2-(2-methylpyrimidin-5-yl)ethyl]benzamide;
- 2,6-difluoro-N-(2-(2-methylpyrimidin-5-yl)-2-morpholinoethyl)benzamide;
- (+)2-chloro-N-[2-(4,4-difluoro-1-piperidyl)-2-(2-methylpyrimidin-5-yl)ethyl]-3-fluoro-benzamide;
- (−)2-chloro-N-[2-(4,4-difluoro-1-piperidyl)-2-(2-methylpyrimidin-5-yl)ethyl]-3-fluoro-benzamide;
- (+)2-chloro-N-[2-(4,4-difluoro-1-piperidyl)-2-(2-methylpyrimidin-5-yl)ethyl]-6-fluoro-benzamide; and
- (−)2-chloro-N-[2-(4,4-difluoro-1-piperidyl)-2-(2-methylpyrimidin-5-yl)ethyl]-6-fluoro-benzamide;

or a pharmaceutically acceptable salt thereof.

20. The compound of claim 1 wherein the compound is selected from the group consisting of:
- (+)2-chloro-N-[2-(4,4-difluoro-1-piperidyl)-2-[2-(trifluoromethyl)pyrimidin-5-yl]ethyl]-6-fluoro-benzamide;
- (−)2-chloro-N-[2-(4,4-difluoro-1-piperidyl)-2-[2-(trifluoromethyl)pyrimidin-5-yl]ethyl]-6-fluoro-benzamide;
- (+)2-chloro-N-[2-(4,4-difluoro-1-piperidyl)-2-[2-(trifluoromethyl)pyrimidin-5-yl]ethyl]-3-fluoro-benzamide;
- (−)2-chloro-N-[2-(4,4-difluoro-1-piperidyl)-2-[2-(trifluoromethyl)pyrimidin-5-yl]ethyl]-3-fluoro-benzamide;
- 2,3-dichloro-N-[2-(4,4-dimethyl-1-piperidyl)-2-[2-(trifluoromethyl)pyrimidin-5-yl]ethyl]benzamide;
- 2-chloro-N-[2-(4,4-dimethyl-1-piperidyl)-2-[2-(trifluoromethyl)pyrimidin-5-yl]ethyl]-3-fluoro-benzamide;
- 2,3-dichloro-N-(2-(2-methylpyrimidin-5-yl)-2-(1,4-oxazepan-4-yl)ethyl)benzamide;
- 2,6-dichloro-N-(2-(2-methylpyrimidin-5-yl)-2-(1,4-oxazepan-4-yl)ethyl)benzamide;
- 2-chloro-6-fluoro-N-(2-(2-methylpyrimidin-5-yl)-2-(1,4-oxazepan-4-yl)ethyl)benzamide;
- 2-chloro-N-(2-(2-methylpyrimidin-5-yl)-2-(1,4-oxazepan-4-yl)ethyl)benzamide;
- 2-chloro-3-fluoro-N-(2-(2-methylpyrimidin-5-yl)-2-(1,4-oxazepan-4-yl)ethyl)benzamide;
- (−)2-chloro-3-methoxy-N-[2-morpholino-2-[2-(trifluoromethyl)pyrimidin-5-yl]ethyl]benzamide;
- (+)2-chloro-3-methoxy-N-[2-morpholino-2-[2-(trifluoromethyl)pyrimidin-5-yl]ethyl]benzamide;
- 2,3-dichloro-N-(2-(2-methylpyrimidin-5-yl)-2-(3-methylpyrrolidin-1-yl)ethyl)benzamide; and
- 2,3-dichloro-N-(2-(2-methylpyrimidin-5-yl)-2-(3,3,4,4-tetrafluoropyrrolidin-1-yl)ethyl)benzamide;

or a pharmaceutically acceptable salt thereof.

21. The compound of claim 1 wherein the compound is selected from the group consisting of:

(+)2-chloro-N-[2-(3,3-difluoro-1-piperidyl)-2-(2-methylpyrimidin-5-yl)ethyl]-6-fluoro-benzamide;
(−)2-chloro-N-[2-(3,3-difluoro-1-piperidyl)-2-(2-methylpyrimidin-5-yl)ethyl]-6-fluoro-benzamide;
(+)2-chloro-N-[2-(3,3-difluoro-1-piperidyl)-2-(2-methylpyrimidin-5-yl)ethyl]-3-fluoro-benzamide;
(−)2-chloro-N-[2-(3,3-difluoro-1-piperidyl)-2-(2-methylpyrimidin-5-yl)ethyl]-3-fluoro-benzamide;
(+)2,3-dichloro-N-[2-(3,3-difluoro-1-piperidyl)-2-(2-methylpyrimidin-5-yl)ethyl]benzamide;
(+)2-chloro-N-[2-(3,3-difluoro-1-piperidyl)-2-(2-methylpyrimidin-5-yl)ethyl]benzamide;
(−)2-chloro-N-[2-(3,3-difluoro-1-piperidyl)-2-(2-methylpyrimidin-5-yl)ethyl]benzamide;
(+)2-chloro-N-[2-(4-fluoro-1-piperidyl)-2-[2-(trifluoromethyl)pyrimidin-5-yl]ethyl]benzamide;
(−)2-chloro-N-[2-(4-fluoro-1-piperidyl)-2-[2-(trifluoromethyl)pyrimidin-5-yl]ethyl]benzamide;
(+)2,6-dichloro-N-[2-(4-fluoro-1-piperidyl)-2-[2-(trifluoromethyl)pyrimidin-5-yl]ethyl]benzamide;
(−)2,6-dichloro-N-[2-(4-fluoro-1-piperidyl)-2-[2-(trifluoromethyl)pyrimidin-5-yl]ethyl]benzamide;
(+)2,3-dichloro-N-[2-(4-fluoro-1-piperidyl)-2-[2-(trifluoromethyl)pyrimidin-5-yl]ethyl]benzamide;
(−)2,3-dichloro-N-[2-(4-fluoro-1-piperidyl)-2-[2-(trifluoromethyl)pyrimidin-5-yl]ethyl]benzamide;
(+)2,6-dichloro-N-[2-(4-fluoro-1-piperidyl)-2-(2-methylpyrimidin-5-yl)ethyl]benzamide;
(−)2,6-dichloro-N-[2-(4-fluoro-1-piperidyl)-2-(2-methylpyrimidin-5-yl)ethyl]benzamide;
(+)2,3-dichloro-N-[2-(4-fluoro-1-piperidyl)-2-(2-methylpyrimidin-5-yl)ethyl]benzamide;
(−)2,3-dichloro-N-[2-(4-fluoro-1-piperidyl)-2-(2-methylpyrimidin-5-yl)ethyl]benzamide;
(+)2-chloro-N-[2-(4-fluoro-1-piperidyl)-2-(2-methylpyrimidin-5-yl)ethyl]benzamide;
(−)2-chloro-N-[2-(4-fluoro-1-piperidyl)-2-(2-methylpyrimidin-5-yl)ethyl]benzamide; and
2,4-dichloro-N-(2-morpholino-2-(2-(trifluoromethyl)pyrimidin-5-yl)ethyl)benzamide;
or a pharmaceutically acceptable salt thereof.

22. The compound of claim 1 wherein the compound is selected from the group consisting of:
(−)2-chloro-N-[2-(4,4-difluoro-1-piperidyl)-2-[2-(trifluoromethyl)pyrimidin-5-yl]ethyl]-3-methoxy-benzamide;
(+)2-chloro-N-[2-(4,4-difluoro-1-piperidyl)-2-[2-(trifluoromethyl)pyrimidin-5-yl]ethyl]-3-methoxy-benzamide;
(−)2,6-dichloro-N-[2-(4,4-difluoro-1-piperidyl)-2-[2-(trifluoromethyl)pyrimidin-5-yl]ethyl]benzamide;
(+)2,6-dichloro-N-[2-(4,4-difluoro-1-piperidyl)-2-[2-(trifluoromethyl)pyrimidin-5-yl]ethyl]benzamide;
(−)2,6-dichloro-N-[2-(4,4-difluoro-1-piperidyl)-2-[2-(trifluoromethyl)pyrimidin-5-yl]ethyl]-3-fluoro-benzamide;
(+)2,6-dichloro-N-[2-(4,4-difluoro-1-piperidyl)-2-[2-(trifluoromethyl)pyrimidin-5-yl]ethyl]-3-fluoro-benzamide;
(−)2-chloro-N-[2-(2-methylpyrimidin-5-yl)-2-(1-piperidyl)ethyl]benzamide;
(+)2-chloro-N-[2-(2-methylpyrimidin-5-yl)-2-(1-piperidyl)ethyl]benzamide;
(−)2,3-dichloro-N-[2-(2-methylpyrimidin-5-yl)-2-(1-piperidyl)ethyl]benzamide;
(+)2,3-dichloro-N-[2-(2-methylpyrimidin-5-yl)-2-(1-piperidyl)ethyl]benzamide;
(−)2,3-dichloro-N-[2-(4,4-difluoro-1-piperidyl)-2-[2-(trifluoromethyl)pyrimidin-5-yl]ethyl]-5-fluoro-benzamide;
(+)2,3-dichloro-N-[2-(4,4-difluoro-1-piperidyl)-2-[2-(trifluoromethyl)pyrimidin-5-yl]ethyl]-5-fluoro-benzamide;
(−)2-chloro-N-[2-[2-(difluoromethyl)pyrimidin-5-yl]-2-morpholino-ethyl]benzamide;
(+)2-chloro-N-[2-[2-(difluoromethyl)pyrimidin-5-yl]-2-morpholino-ethyl]benzamide; and
(−)2-chloro-N-[2-(4,4-difluoro-1-piperidyl)-2-(2-methylpyrimidin-5-yl)ethyl]-3-methoxy-benzamide;
or a pharmaceutically acceptable salt thereof.

23. The compound of claim 1 wherein the compound is selected from the group consisting of:
(+)2-chloro-N-[2-(4,4-difluoro-1-piperidyl)-2-(2-methylpyrimidin-5-yl)ethyl]-3-methoxy-benzamide;
(−)2,6-dichloro-N-[2-(4,4-difluoro-1-piperidyl)-2-(2-methylpyrimidin-5-yl)ethyl]-3-fluoro-benzamide;
(+)2,6-dichloro-N-[2-(4,4-difluoro-1-piperidyl)-2-(2-methylpyrimidin-5-yl)ethyl]-3-fluoro-benzamide;
(−)2,6-dichloro-N-[2-(4,4-difluoro-1-piperidyl)-2-(2-methylpyrimidin-5-yl)ethyl]benzamide;
(+)2,6-dichloro-N-[2-(4,4-difluoro-1-piperidyl)-2-(2-methylpyrimidin-5-yl)ethyl]benzamide;
(−)2,3-dichloro-N-[2-(4,4-difluoro-1-piperidyl)-2-(2-methylpyrimidin-5-yl)ethyl]-5-fluoro-benzamide;
(+)2,3-dichloro-N-[2-(4,4-difluoro-1-piperidyl)-2-(2-methylpyrimidin-5-yl)ethyl]-5-fluoro-benzamide;
(−)2,3-dichloro-N-[2-(4,4-difluoro-1-piperidyl)-2-(2-methylpyrimidin-5-yl)ethyl]benzamide;
(+)2,3-dichloro-N-[2-(4,4-difluoro-1-piperidyl)-2-(2-methylpyrimidin-5-yl)ethyl]benzamide;
(−)2,3-dichloro-N-[2-[2-(difluoromethyl)pyrimidin-5-yl]-2-morpholino-ethyl]benzamide;
(+)2,3-dichloro-N-[2-[2-(difluoromethyl)pyrimidin-5-yl]-2-morpholino-ethyl]benzamide;
(−)2-chloro-N-[2-[2-(difluoromethyl)pyrimidin-5-yl]-2-morpholino-ethyl]-3-fluoro-benzamide;
(+)2-chloro-N-[2-[2-(difluoromethyl)pyrimidin-5-yl]-2-morpholino-ethyl]-3-fluoro-benzamide;
(−)2-chloro-N-[2-(2-cyclopropylpyrimidin-5-yl)-2-(4,4-difluoro-1-piperidyl)ethyl]benzamide;
(+)2-chloro-N-[2-(2-cyclopropylpyrimidin-5-yl)-2-(4,4-difluoro-1-piperidyl)ethyl]benzamide;
(−)2,6-dichloro-N-[2-(2-cyclopropylpyrimidin-5-yl)-2-(4,4-difluoro-1-piperidyl)ethyl]benzamide;
(+)2,6-dichloro-N-[2-(2-cyclopropylpyrimidin-5-yl)-2-(4,4-difluoro-1-piperidyl)ethyl]benzamide;
(−)2-chloro-N-[2-(4,4-difluoro-1-piperidyl)-2-(2-ethylpyrimidin-5-yl)ethyl]benzamide;
(+)2-chloro-N-[2-(4,4-difluoro-1-piperidyl)-2-(2-ethylpyrimidin-5-yl)ethyl]benzamide; and
(−)2,6-dichloro-N-[2-(4,4-difluoro-1-piperidyl)-2-(2-ethylpyrimidin-5-yl)ethyl]benzamide;
or a pharmaceutically acceptable salt thereof.

24. The compound of claim 1 wherein the compound is selected from the group consisting of:
(+)2,6-dichloro-N-[2-(4,4-difluoro-1-piperidyl)-2-(2-ethylpyrimidin-5-yl)ethyl]benzamide;
(−)2-chloro-3-(difluoromethoxy)-N-[2-(4,4-difluoro-1-piperidyl)-2-(2-methylpyrimidin-5-yl)ethyl]benzamide;
(+)2-chloro-3-(difluoromethoxy)-N-[2-(4,4-difluoro-1-piperidyl)-2-(2-methylpyrimidin-5-yl)ethyl]benzamide;

(−)2,3-dichloro-N-[2-(4,4-difluoro-1-piperidyl)-2-(2-ethylpyrimidin-5-yl)ethyl]benzamide;
2,3-dichloro-N-(2-morpholino-2-pyrimidin-5-yl-ethyl) benzamide;
2,3-dichloro-N-[2-(2-methylpyrimidin-5-yl)-2-morpholino-ethyl]benzamide;
2,3-dichloro-N-[2-morpholino-2-[2-(trifluoromethyl)pyrimidin-5-yl]ethyl]benzamide;
(−)2,3-dichloro-N-[2-morpholino-2-[2-(trifluoromethyl)pyrimidin-5-yl]ethyl]benzamide;
(+)2,3-dichloro-N-[2-morpholino-2-[2-(trifluoromethyl)pyrimidin-5-yl]ethyl]benzamide;
(−)2-chloro-N-[2-morpholino-2-[2-(trifluoromethyl)pyrimidin-5-yl]ethyl]-3-(trifluoromethyl)benzamide;
(+)2-chloro-N-[2-morpholino-2-[2-(trifluoromethyl)pyrimidin-5-yl]ethyl]-3-(trifluoromethyl)benzamide; and
(−)2,3-dichloro-N-[2-[2-(difluoromethyl)pyrimidin-5-yl]-2-morpholino-ethyl]benzamide;
or a pharmaceutically acceptable salt thereof.

* * * * *